(12) United States Patent
Hoshiko et al.

(10) Patent No.: US 7,760,340 B2
(45) Date of Patent: Jul. 20, 2010

(54) SAMPLE ANALYZER

(75) Inventors: Susumu Hoshiko, Kobe (JP); Naohiko Matsuo, Kobe (JP); Katsushi Kobayashi, Kobe (JP); Norimasa Yamamoto, Kobe (JP)

(73) Assignee: Sysmex Corporation, Kobe (JP)

( * ) Notice: Subject to any disclaimer, the term of this patent is extended or adjusted under 35 U.S.C. 154(b) by 493 days.

(21) Appl. No.: 11/724,934

(22) Filed: Mar. 16, 2007

(65) Prior Publication Data
US 2007/0222973 A1    Sep. 27, 2007

(30) Foreign Application Priority Data
Mar. 16, 2006  (JP) .............................. 2006-072446
Mar. 30, 2006  (JP) .............................. 2006-092723

(51) Int. Cl.
*G01N 33/48* (2006.01)
(52) U.S. Cl. .............................. 356/39; 356/336; 422/73
(58) Field of Classification Search .................. 356/39, 356/336, 338; 600/309, 310, 320, 322, 336; 436/49, 43, 47, 48, 55, 63; 422/63–65, 73
See application file for complete search history.

(56) References Cited

U.S. PATENT DOCUMENTS

| 4,013,417 | A | * | 3/1977 | Raffaele ........................ 422/67 |
| 4,263,512 | A |   | 4/1981 | Sagusa et al. |
| 4,997,769 | A | * | 3/1991 | Lundsgaard ................ 436/66 |
| 5,646,046 | A | * | 7/1997 | Fischer et al. ................ 436/49 |
| 5,692,503 | A | * | 12/1997 | Kuenstner .................... 600/322 |
| 5,734,468 | A |   | 3/1998 | McNeal |
| 6,594,513 | B1 | * | 7/2003 | Jobsis et al. ................ 600/328 |
| 6,855,562 | B1 | * | 2/2005 | Yamao et al. ................ 436/523 |
| 7,075,628 | B2 | * | 7/2006 | Shepherd et al. ............. 356/40 |
| 7,271,912 | B2 | * | 9/2007 | Sterling et al. ............. 356/436 |

FOREIGN PATENT DOCUMENTS

| EP | 0268025 A1 | 5/1988 |
| JP | 55-30613   | 3/1980 |
| JP | 57-059151  | 4/1982 |
| JP | 06-066808  | 3/1994 |

OTHER PUBLICATIONS

Partial European Search Report dated Dec. 2, 2009 for Corresponding European Patent Application No. 07005464.8.

* cited by examiner

*Primary Examiner*—L. G Lauchman
(74) *Attorney, Agent, or Firm*—Brinks Hofer Gilson & Lione

(57) ABSTRACT

A sample analyzer includes (a) a measuring part for measuring optical information of a sample at first wavelength, second wavelength, and third wavelength, first light of the first wavelength and second light of the second wavelength being absorbed by a second substance but substantially not absorbed by a first substance, and third light of the third wavelength being absorbed by the first substance; and (b) an obtaining part for obtaining content of the first substance in the sample, and content of the second substance in the sample, influence by the second substance being excluded from the content of the first substance, based on the optical information at the first wavelength, second wavelength, and third wavelength measured by the measuring part.

23 Claims, 35 Drawing Sheets

FIG. 20

| Sample No. | Measurement item | Secondary dispencing flag | Interference substance flag ||| Wavelength change flag | High gain flag |
|---|---|---|---|---|---|---|---|
| | | | Bilirubin | Hemoglobin | Chyle | | |
| 000101 | PT | 0 | 0 | 0 | 0 | 0 | 0 |
| 000101 | AT III | 0 | 0 | 0 | 0 | 0 | 0 |
| 000102 | APTT | 0 | 0 | 0 | 0 | 0 | 0 |
| 000102 | FDP | 0 | 0 | 0 | 0 | 0 | 0 |
| ⋮ | ⋮ | ⋮ | ⋮ | ⋮ | ⋮ | ⋮ | ⋮ |

SAMPLE ANALYZER

RELATED APPLICATIONS

This application claims priority under 35 U.S.C. §119 to Japanese Patent Application No. JP2006-072446 filed Mar. 16, 2006, and Japanese Patent Application No. JP2006-092723 filed Mar. 30, 2006, the entire content of which is hereby incorporated by reference.

FIELD OF THE INVENTION

The present invention relates to a sample analyzer.

BACKGROUND OF THE INVENTION

A clinical analyzer is an example of sample analyzer conventionally used in the field of clinical laboratory examination. Evaluation of sample quality is performed by measuring interference substances (hemoglobin, bilirubin, chyle and the like) in the sample prior to examination of target substances that are the object of examination. Interference substances are present in samples together with target substances, and may adversely affect the measurement of a target substance. These interference substances might prevent accurate optical measurement of the target substance. The concentrations of these interference substances can be determined by measuring optical absorbance at several different wavelengths specific to each interference substances. If chyle is present in a sample, it is difficult to accurately measure concentration of bilirubin or hemoglobin because the absorbance baselines at the specific wavelengths of bilirubin and hemoglobin are elevated by the chyle. It is desirable that hemoglobin and bilirubin measurements are performed so as to be uninfluenced by the presence of chyle when measuring interference substances during evaluation of sample quality.

Conventional measuring methods have been proposed for eliminating the influence by chyle by estimating an optical absorbance at a predetermined wavelength and subtracting the estimated optical absorbance from the measured optical absorbance at that wavelength by using cycle absorbance represented as an exponential function of the wavelength (for example, refer to Japanese Laid-Open Patent Publication No. 6-66808). According to the measuring method disclosed in Japanese Laid-Open Patent Publication No. 6-66808, an absorbance A at a predetermined wavelength λ is estimated by substituting the absorbance obtained at the wavelength (660 nm), which hemoglobin and bilirubin do not substantially absorb and chyle does absorb, with an exponential function ($A = \alpha \cdot \lambda^\beta$ (where A represents the optical absorbance, $\alpha$ represents a constant attributed to the particle, $\beta$ represents a constant attributed to mean particle size, and $\lambda$ represents a wavelength)) representing the relationship between the wavelength and the chyle absorbance.

Since only a single absorbance is used and the absorbance is at the wavelength which hemoglobin and bilirubin do not substantially absorb and chyle does absorb in the measuring method disclosed in Japanese Laid-Open Patent Publication No. 6-66808, approximate expression is used to determine the unknowns a (constant attributed to the particle) and p (constant attributed to mean particle size) in the equation for estimating the optical absorbance A at a predetermined wavelength λ ($A = \alpha \cdot \beta$). Therefore, it is difficult to calculate an accurate estimate value (optical absorbance), which makes it difficult to obtain an accurate measurement result that does not include the influence by chyle.

In the chromogen (interference substance) measuring method disclosed in Japanese Laid-Open Patent Publication No. 6-66808, a sample blank solution is prepared by mixing a blank reaction reagent with a sample containing suspended substances (hemoglobin, bilirubin, chyle and the like). The amount of the interference substance is measured by irradiating the sample blank fluid with light of four wavelengths that include wavelengths that chyle absorbs and hemoglobin and bilirubin does not absorbs substantially. Specifically, the amount of chyle is calculated by assuming an optical absorbance expressed as an exponential function of wavelength and determining the regression curve of the wavelength-absorbance. Furthermore, the amounts of hemoglobin and bilirubin are calculated by assuming a constant relationship established between absorbance at different wavelengths, and preparing and solving simultaneous linear equations relating to absorbance at a measured wavelength.

According to the method of Japanese Laid-Open Patent Publication No. 6-66808, a sample blank fluid that can not be used in the main measurement (measurement that is the conventional goal) must be prepared for optical measurement of interference substances. Therefore, the measurement of the interference substances must be performed separately from the main measurement. Moreover, since a sample such as serum or the like must be prepared for the sample blank fluid separately from the main measurement, the sample is disadvantageously consumed before obtaining the main measurement result.

Moreover, other arts have been proposed for measuring interference substances (hemoglobin, bilirubin, chyle and the like) in samples, wherein the quality of the sample (serum and the like) is evaluated prior to performing a main measurement (for example, biochemical analysis) (for example, refer to Japanese Laid-Open Patent Publication No. 57-59151 and U.S. Pat. No. 5,734,468).

In the method for measuring chyle, icterus, and hemolysis in serum disclosed in Japanese Laid-Open Patent Publication No. 57-59151, the serum is irradiated with four wavelengths of light, and the absorbance is measured primarily using the light of shortest wavelength in the visible range (for example, 410 nm). Then, serum that has a measured absorbance greater than a set value is determined to be abnormal due to the level of chyle, icterus, or hemolysis. Secondarily, with regard to serum that has been determined to be abnormal, the degrees of chyle, icterus, and hemolysis are determined by comparing the absorbance measured using the four wavelengths of light with several types of preset standards.

Furthermore, in the analyzer disclosed in U.S. Pat. No. 5,734,468, the absorbance of a sample within a needle tube is first measured by irradiating a serum sample aspirated to the needle tube disposed in a transparent part provided in a probe using light emitted from a light-emitting diode. Then, a serum sample that has been determined to be measurable based on this absorbance is moved to the analyzer and the main measurement is performed.

However, the interference substances in a sample are measured using a sample such as serum or the like in an original concentration prior to performing the main measurement (biochemical analysis or the like) in Japanese Laid-Open Patent Publication No. 57-59151 and U.S. Pat. No. 5,734,468. Therefore, an optical measurement structure (for example, an optical sensor or probe) for measuring the sample at an original concentration must be disadvantageously provided separately from the main measurement part.

SUMMARY OF THE INVENTION

The scope of the present invention is defined solely by the appended claims, and is not affected to any degree by the statements within this summary.

The first aspect of the present invention relates to a sample analyzer comprising:

a measuring part for measuring optical information of a sample at first wavelength, second wavelength, and third wavelength, first light of the first wavelength and second light of the second wavelength being absorbed by a second substance but substantially not absorbed by a first substance, and third light of the third wavelength being absorbed by the first substance; and an obtaining means for obtaining content of the first substance in the sample, and content of the second substance in the sample, influence by the second substance being excluded from the content of the first substance, based on the optical information at the first wavelength, second wavelength, and third wavelength measured by the measuring part.

The second aspect of the present invention relates to a sample analyzer comprising:

a sample preparing part for preparing a measurement sample by mixing a reagent for measuring coagulation time with a blood sample;

a light emitting part for emitting light to the prepared measurement sample;

a light receiving part for obtaining optical information at a plurality of time points by receiving light of a plurality of wavelengths over time from the measurement sample irradiated by the light;

a first measuring means for measuring content of an interference substance in the measurement sample that interferes optical measurement of the measurement sample based on optical information obtained by the light receiving part at a time point before the measurement sample indicates coagulation reaction; and a second measuring means for measuring coagulation time of the measurement sample based on the optical information obtained by the light receiving part.

The third aspect of the present invention relates to a sample analyzer comprising:

a sample preparing part for preparing a measurement sample by mixing a reagent for measuring coagulation time with a blood sample;

a light emitting part for emitting light to the prepared measurement sample;

a light receiving part for obtaining optical information at a plurality of time points by receiving light of a plurality of wavelengths over time from the measurement sample irradiated by the light;

a specifying means for specifying an interference substance in the measurement sample that interferes optical measurement of the measurement sample, based on optical information at a time point before the measurement sample indicates coagulation reaction; and a measuring means for measuring coagulation time of the measurement sample based on the optical information obtained by the light receiving part.

BRIEF DESCRIPTION OF THE DRAWINGS

FIG. 20 shows a sample analysis table output to the display from the control device of the sample analyzer of the first embodiment in FIG. 1;

DETAILED DESCRIPTION OF THE DRAWINGS AND THE PRESENTLY PREFERRED EMBODIMENTS

First Embodiment

Figure 1:
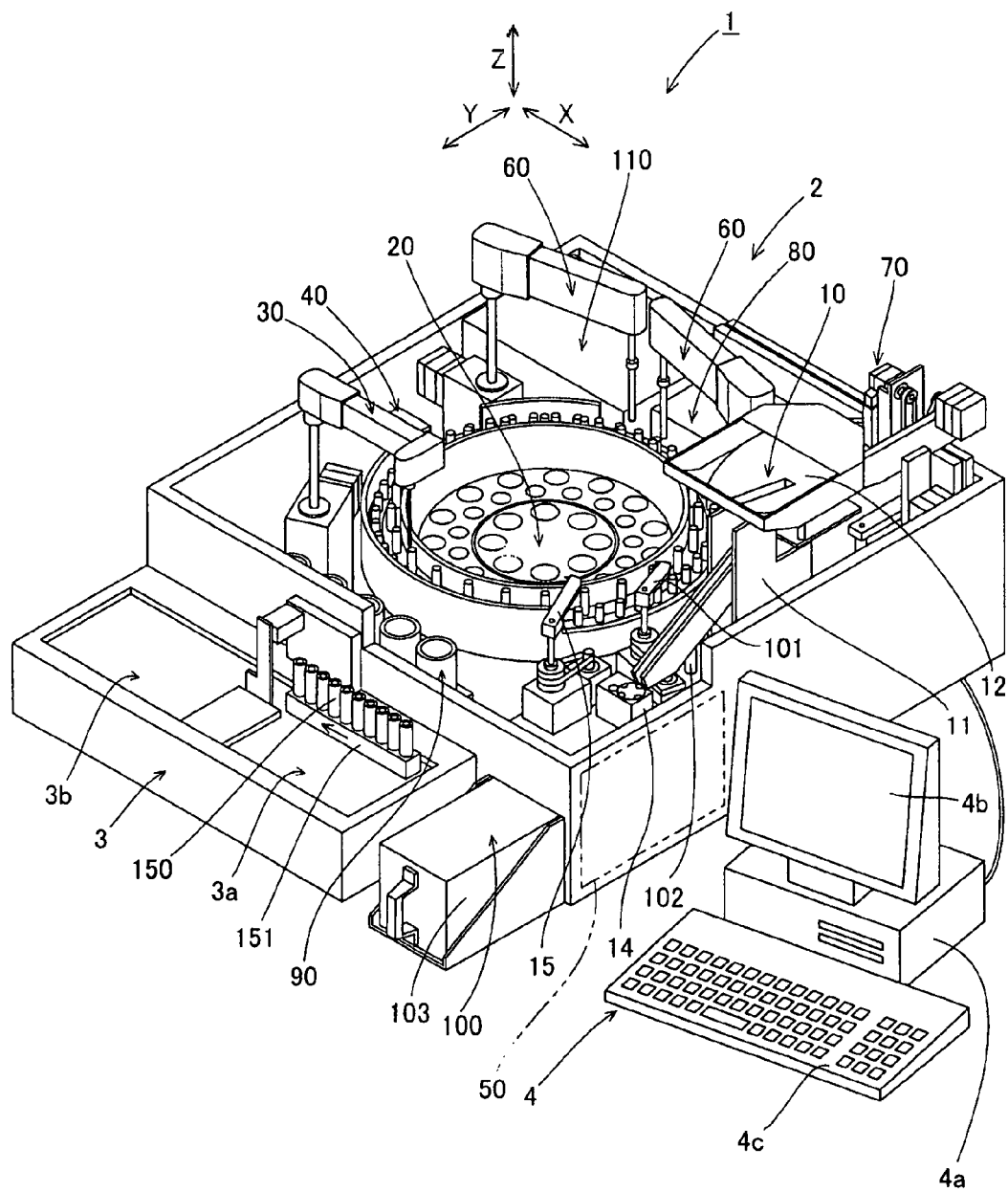
FIG. 1 is a perspective view showing the general structure of a first embodiment of the sample analyzer.
Figure 2:
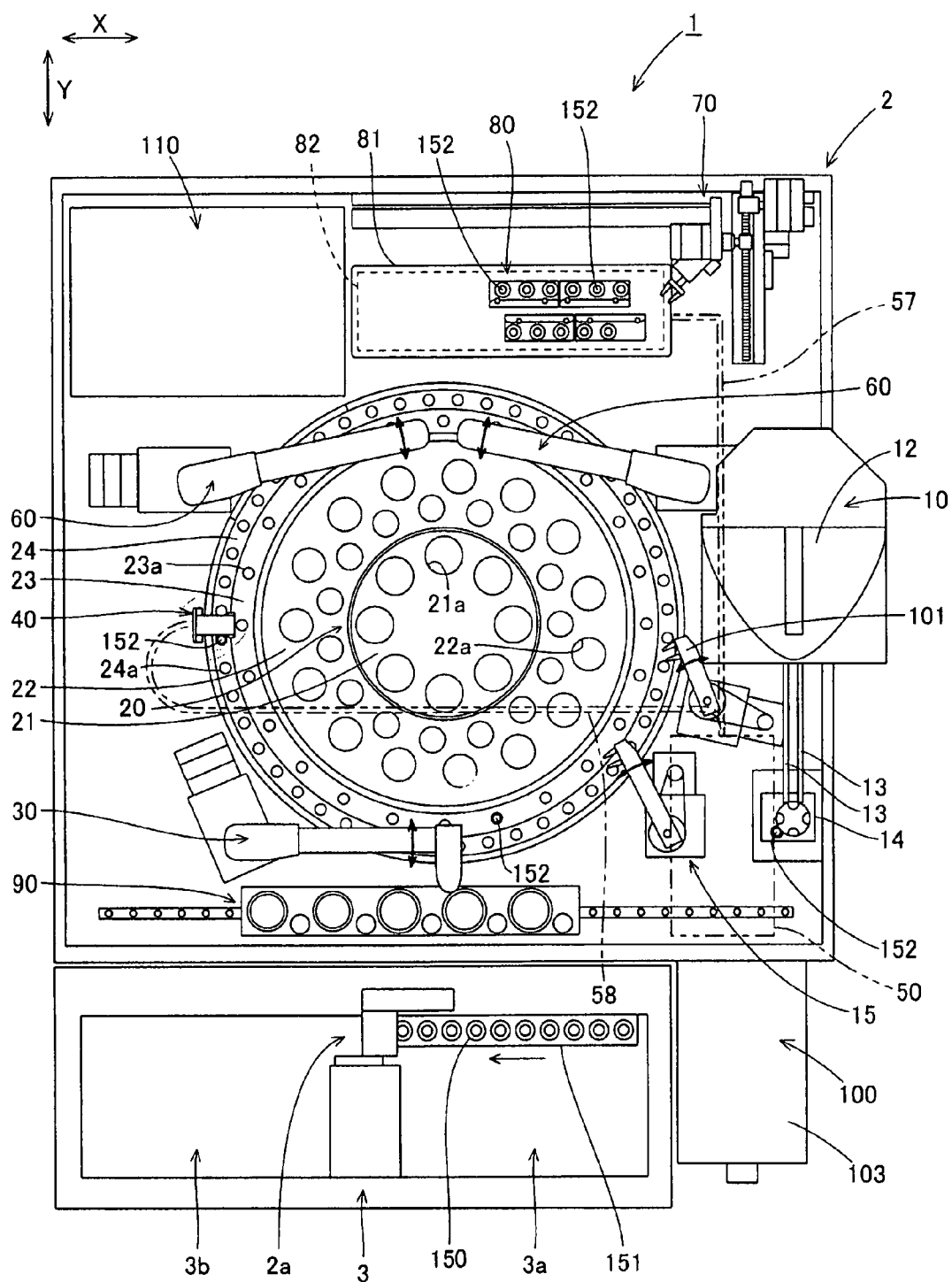
FIG. 2 is a top view showing the detection device and transport device of the sample analyzer of the first embodiment in FIG. 1.
Figure 3:
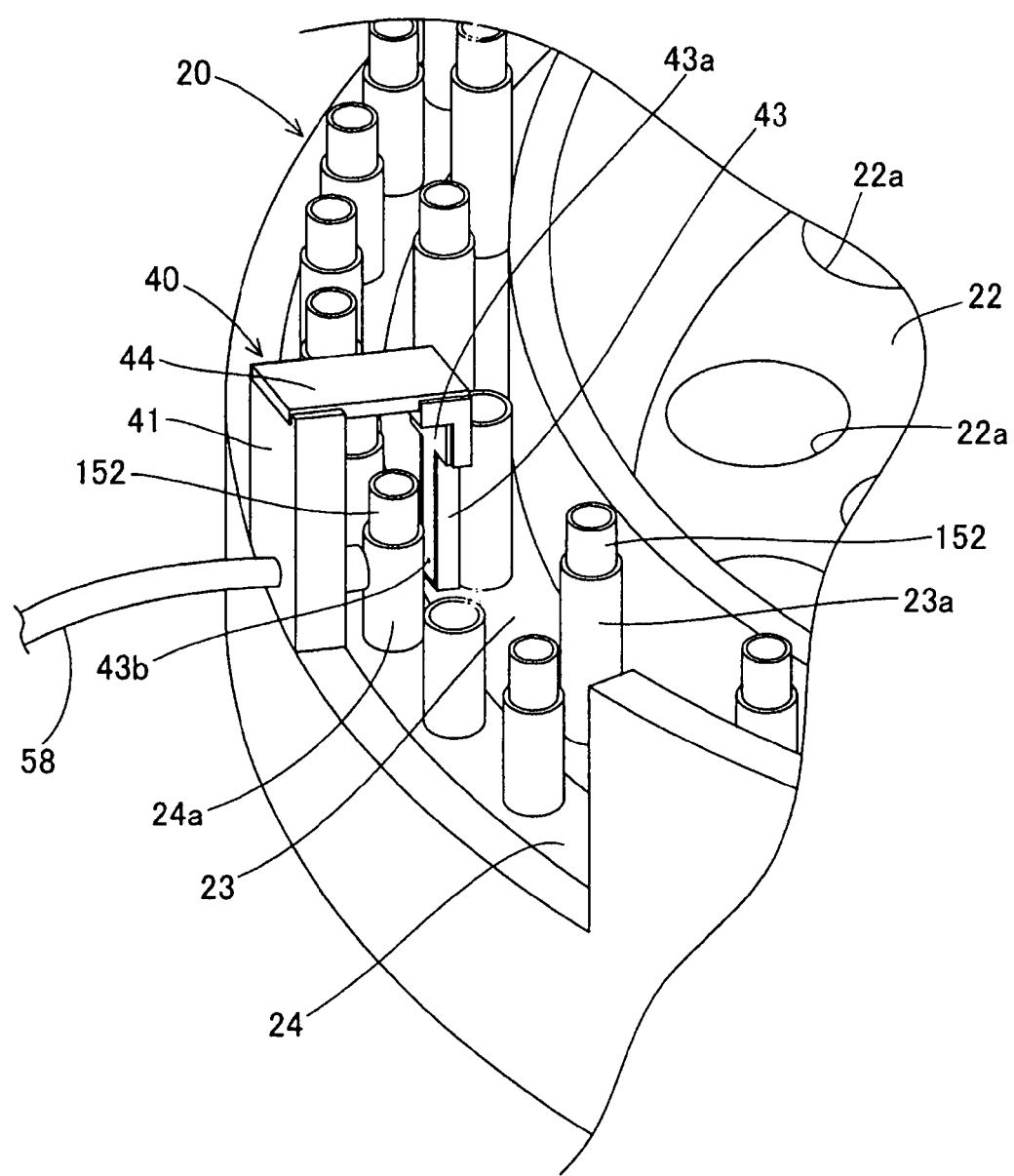
FIG. 3 is a perspective view showing a first optical information obtaining part of the sample analyzer of the first embodiment in FIG. 1.
Figure 4:
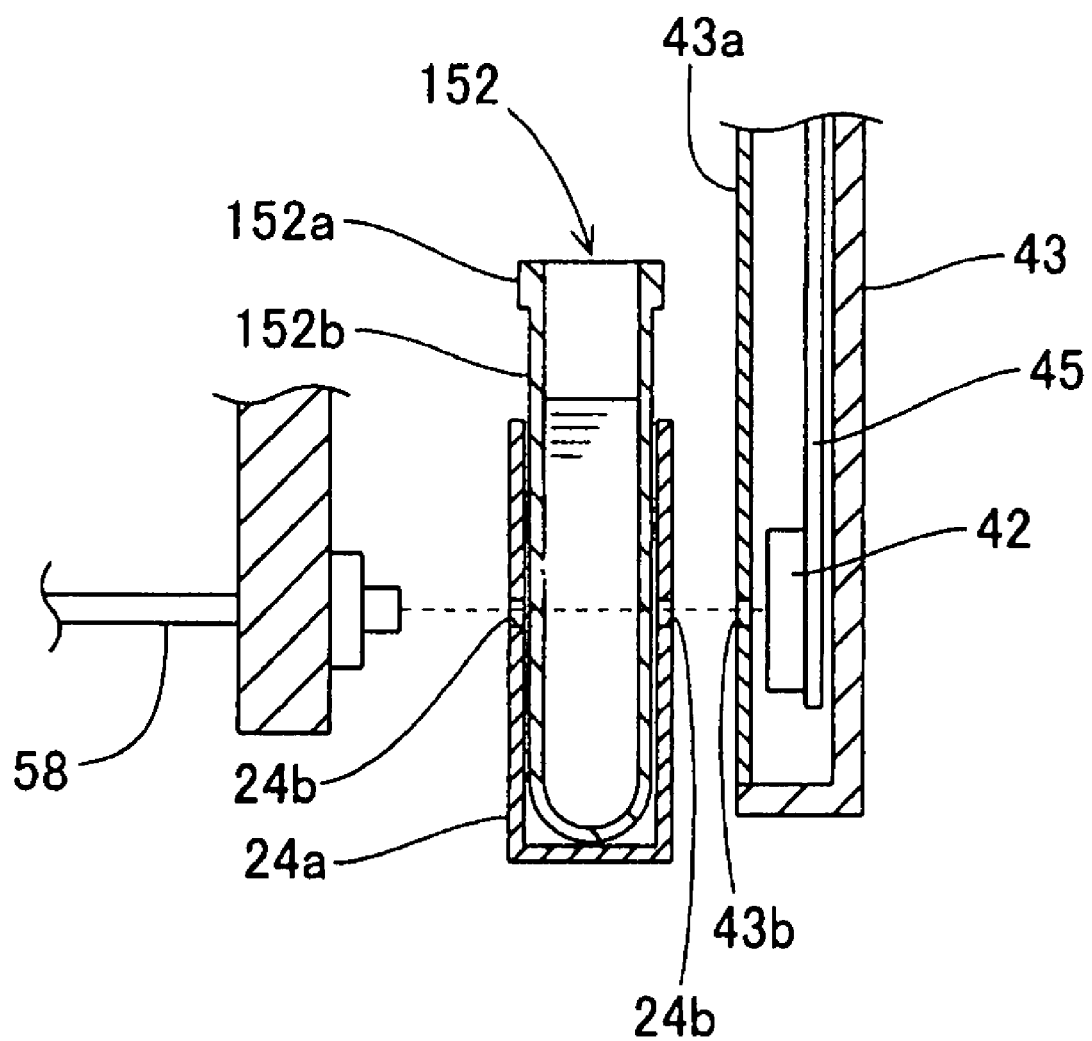
FIG. 4 is a schematic view illustrating the structure of the first optical information obtaining part of the sample analyzer of the first embodiment in FIG. 1.

FIG. 1 is a perspective view showing the general structure of a first embodiment of the sample analyzer of the present invention, and FIG. 2 is a top view of the detection device and transport device of the sample analyzer of the first embodiment in FIG. 1. FIGS. 3 and 4 are illustrations of the structure of the sample analyzer of the first embodiment in FIG. 1. The general structure of the sample analyzer of the first embodiment of the present invention is described hereinafter with reference to FIGS. 1 through 14.

The sample analyzer 1 of the first embodiment of the present invention optically measures and analyzes the amount of specific substances and the degree of their activity related to blood coagulation and fibrinolysis function using plasma as a blood sample. The sample analyzer 1 of the present embodiment measures the coagulation time of a blood sample by optically measuring the blood sample using a blood coagulation time method, synthetic substrate method, and immunoturbidity method. Measurement items include PT (prothrombin time), APTT (active partial thromboplastin time), and Fbg (fibrinogen content) and the like. Furthermore, measurement items of the synthetic substrate method include ATIII and the like, and measurement items of the immunoturbidity method include D dimer, FDP and the like.

The sample analyzer 1 is configured by a detection device 2, transport device 3 disposed on the front side of the detection device 2, and a control device 4 electrically connected to the detection device 2, as shown in FIG. 1.

The transport device 3 has the function of transporting a rack 151 holding a plurality of test tubes 150 (ten tubes in the present embodiment) that contain samples to an aspiration position 2a (refer to FIG. 2) of the detection device 2 so as to supply blood sample to the detection device. Furthermore, the transport device 3 has a rack set region 3a that accommodates the racks 151 that hold the test tubes 150 containing unprocessed samples, and a rack receiving region 3b that accommodates the racks 151 that hold test tubes 150 containing processed samples.

The detection device 2 is configured to obtain optical information relating to a supplied sample by optically measuring a sample supplied from the transport device 3. In the present embodiment, optical-measurement is performed on a blood sample dispensed into a cuvette 152 (refer to FIG. 2) of the detection device 2 from a test tube 150 loaded in the rack 151 of the transport device 3. Furthermore, the detection device 2 includes a cuvette supplier 10, rotating part 20, sample dispensing arm 30, first optical information obtaining part 40, lamp unit 50, two reagent dispensing arms 60, cuvette transporter 70, second optical information obtaining part 80, rush sample acceptor 90, cuvette disposal 100, and fluid provider 110, as shown in FIGS. 1 and 2.

The cuvette supplier 10 is configured to sequentially supply a plurality of cuvettes 152 directly inserted by a user to the rotating part 20. As shown in FIG. 2, the cuvette supplier 10 includes a hopper 12 mounted on the device body via a bracket 11 (refer to FIG. 1), two induction plates 13 provided below the hopper 12, support base 14 disposed at the bottom end of the two induction plates 13, and catcher 15 provided at a predetermined distance from the support base 14. The two induction plates 13 are disposed so as to be mutually parallel with a space therebetween so as to be smaller than the diameter of the flange 152a (refer to FIG. 4) of the cuvette 152 and larger than the diameter of the barrel 152b (refer to FIG. 4) of the cuvette 152. The cuvettes 152 supplied into the hopper 12 are configured so as to move smoothly toward the support base 14 with the flange 152a engaged at the top surface of the two induction plates 13. Furthermore, the support base 14 functions to rotate the cuvette 152 that has fallen between the induction plates 13 to a position at which the cuvette 152 can be grabbed by the catcher 15. The catcher 15 is provided to supply the cuvette 152, which has been moved by the support base 14, to the rotating part 20.

The rotating part 20 is provided to transport in a circular direction the cuvettes 152 received from the cuvette supplier 10, and reagent containers (not shown in the drawings) accommodating reagent for measuring the coagulation time of a blood sample. As shown in FIG. 2, the rotating part 20 is configured by a circular reagent table 21, annular reagent table 22 disposed on the outer side of the circular reagent table 21, annular secondary dispensing table 23 disposed on the outer side of the circular reagent table 22, and annular primary dispensing table 24 disposed on the outer side of the circular secondary dispensing table 23. The primary dispensing table 24, secondary dispensing table 23, and reagent tables 21 and 22 are configured so as to be mutually and independently rotatable in both clockwise and counter clockwise directions.

As shown in FIG. 2, the reagent tables 21 and 22 respectively include a plurality of holes 21a and 22a provided at predetermined spacing in the circumferential direction. The holes 21a and 22a of the reagent tables 21 and 22 are provided to load a plurality of reagent containers (not shown in the drawings) that hold reagent for coagulating the blood sample and measuring blood coagulation time. Furthermore, the primary dispensing table 24 and secondary dispensing table 23 respectively include a plurality of cylindrical holders 24a and 23a provided at predetermined spacing in the circumferential direction. The holders 24a and 23a are provided to hold the cuvettes 152 received from the cuvette supplier 10. A blood sample contained in a test tube 150 of the transport device 3 is dispensed to a cuvette 152 held by the holder 24a of the primary dispensing table 24 during a primary dispensing process. Furthermore, a blood sample contained in the cuvette 152 loaded in the primary dispensing table is dispensed to a cuvette 152 loaded in the holder 23a of the secondary dispensing table 23 during a secondary dispensing process. A pair of small holes 24b are formed in the holder 24a at mutually opposed positions on the sides of the holder 24a. The pair of small holes 24b are provided to allow the transmission of light emitted from a beam splitter optical fiber 58 of the lamp unit 50 which is described later.

The sample dispensing arm 30 functions to both aspirate blood sample contained in a test tube 150 transported to the aspiration position 2a via the transport device 3, and dispensing the aspirated blood sample into a cuvette 152 transported to the rotating part 20.

The first optical information obtaining part 40 is configured so as to obtain optical information from a blood sample (raw sample without added dilution liquid and reagent for measuring blood coagulation time) in order to measure the presence and concentration of interference substances (chyle, hemoglobin, and bilirubin) in the blood sample before adding the dilution liquid and reagent for measuring blood coagulation time. Specifically, the presence and concentration of interference substances is measured using four wavelengths of light (405 nm, 575 nm, 660 nm, 800 nm) among five wavelengths of light (340 nm, 405 nm, 575 nm, 660 nm, 800 nm) emitted from the lamp unit 50 which is described later.

Obtaining optical information of a blood sample by the first optical information obtaining part 40 is performed before the optical measurement of a measurement sample (main measurement) by the second optical information obtaining part 80. As shown in FIGS. 2 and 3, the first optical information obtaining part 40 obtains optical information from a blood sample within a cuvette 152 loaded in the holder 24a of the primary dispensing table 24. As shown in FIGS. 3 and 4, the first optical information obtaining part 40 includes an emission side holder 41, photoelectric conversion element 42 (refer to FIG. 4), receiving side holder 43, bracket 44, and base plate 45 for mounting the photoelectric conversion element 42.

The receiving side holder 43 is mounted on the emission side holder 41 via the bracket 44 (refer to FIG. 3), and is formed in a shape that is capable of internally accommodating the base plate 45 on which the photoelectric conversion element 42 is mounted, as shown in FIG. 4. A cover 43a, which is provided with a slit 43b at a predetermined position, is mounted on the receiving side holder 43. The light from the beam splitter optical fiber 58 (described later), which passed through the cuvette 152 held by the holder 24a of the primary dispensing table 24, is detected by the photoelectric conversion element 42 by means of the pair of small holes in the holder 24a and the slit 43b of the receiving side holder 43.

Figure 5:
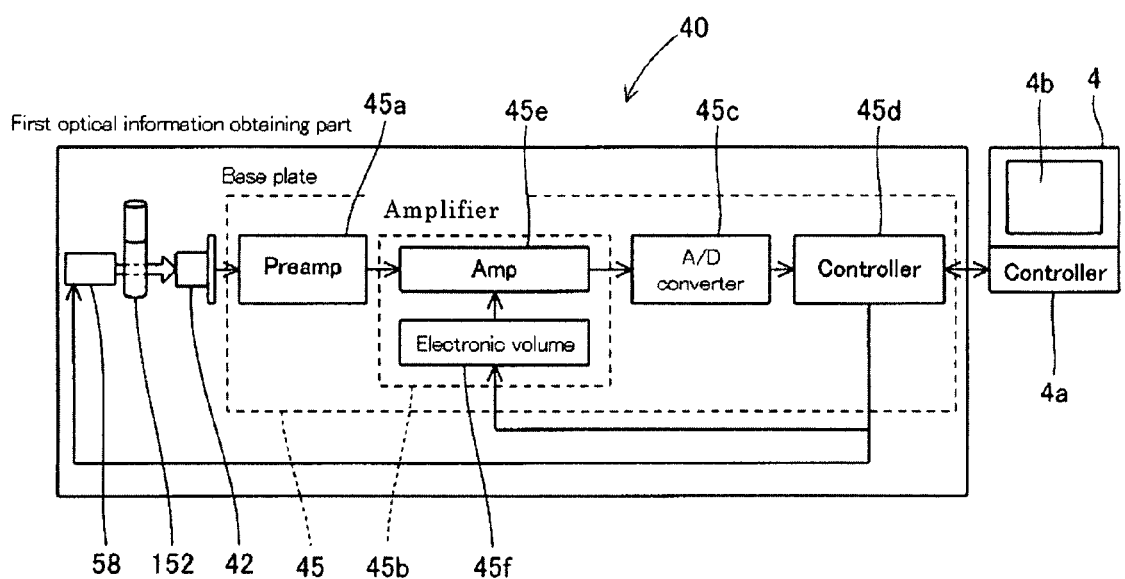
FIG. 5 is a block diagram of the first optical information obtaining part of the sample analyzer of the first embodiment on FIG. 1.

The base plate 45 functions to amplify the electrical signal corresponding to the amount of light detected by the photoelectric conversion element 42, and transmit the amplified signal to the controller 4a of the control device 4. The base plate 45 is configured by a preamp 45a, amplifier 45b, A/D converter 45c, and controller 45d, as shown in FIG. 5. The amplifier 45b has an amp 45e and electronic volume 45f. The preamp 45a and amp 45e are provided to amplify the electric signal detected by the photoelectric conversion element 42. The amp 45e of the amplifier 45b is configured so as to regulate the gain (amplification factor) of the amp 45e via a control signal from the controller 45d input to the electronic volume 45f. The A/D converter 45c is provided to convert the electric signals (analog signals) amplified by the amp 45e to digital signals.

The controller 45d is configured so as change the gain (amplification factor) of the amp 45e to conform to the periodic change in the wavelength (340 nm, 405 nm, 575 nm, 660 nm, 800 nm) of the light emitted from the beam splitter optical fiber 58 of the lamp unit 50, which is described later. Furthermore, the controller 45d is electrically connected to the controller 4a of the control device 4, and transmits digital signal data corresponding to the amount of transmission light obtained by the first optical information obtaining part 40 to the controller 4a of the control device 4.

Figure 6:
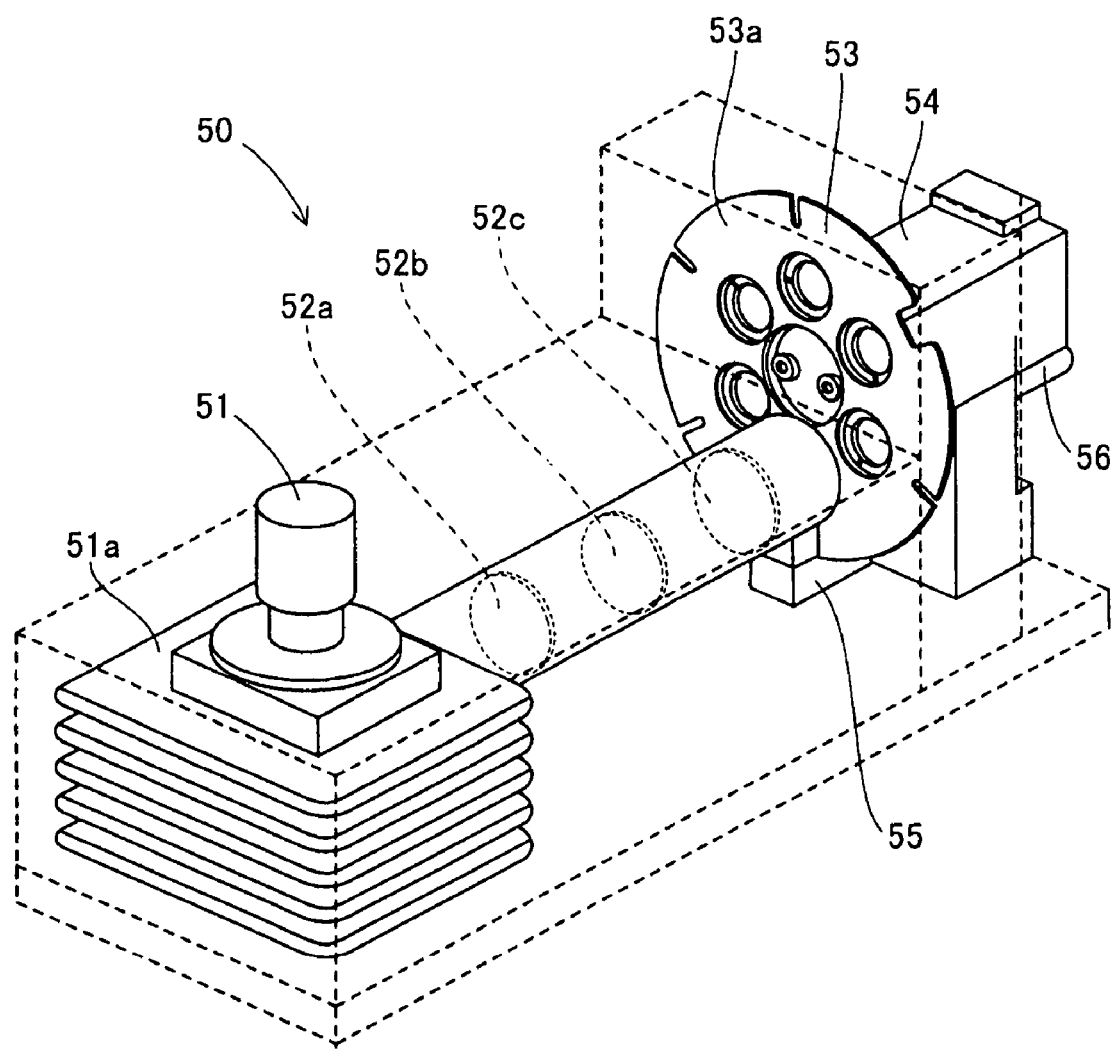
FIG. 6 is a perspective view showing a lamp unit of the sample analyzer of the first embodiment in FIG. 1.
Figure 7:
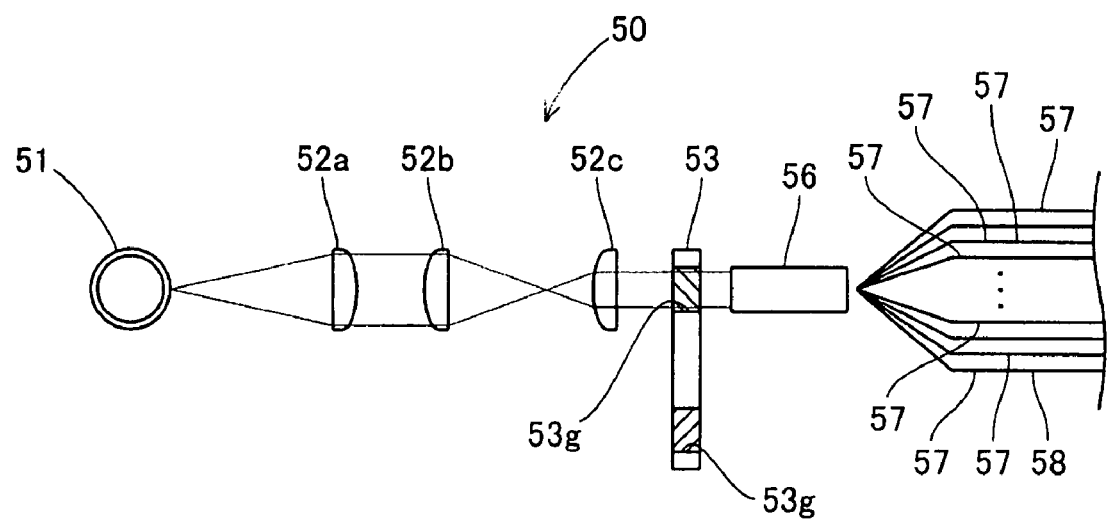
FIG. 7 is a schematic view illustrating the structure of the lamp unit of the sample analyzer of the first embodiment in FIG. 1.

The lamp unit 50 is provided for supplying light used for the optical measurement performed by the optical information obtaining part 40 and second optical information obtaining part 80, as shown in FIG. 2. That is, one lamp unit 50 is configured so as to be used jointly by the first optical information obtaining part 40 and the second optical information obtaining part 80. As shown in FIGS. 6 and 7, the lamp unit 50 is configured by a halogen lamp 51 as a light source, collective lenses 52a through 52c, disk-shaped filter part 53, motor 54, transmission light sensor 55, optical fiber coupler 56, eleven beam splitter optical fibers 57 (refer to FIG. 7), and one beam splitter optical fiber 58 (refer to FIG. 7).

As shown in FIG. 6, the halogen lamp 51 is accommodated in a lamp case 51a having a plurality of fins to dissipate the heat generated by the halogen lamp 51 via air cooling. The collective lenses 52a through 52c function to collect the light emitted from the halogen lamp 51. The collective lenses 52a through 52c are disposed on the optical path to direct the light emitted from the halogen lamp 51 to the optical fiber coupler 56. The light emitted from the halogen lamp 51 and collected by the collective lenses 52a through 52c passes through one or another of the optical fibers 53b through 53f of the filter part 53, which is described later, and directed to the optical fiber coupler 56.

Figure 8:
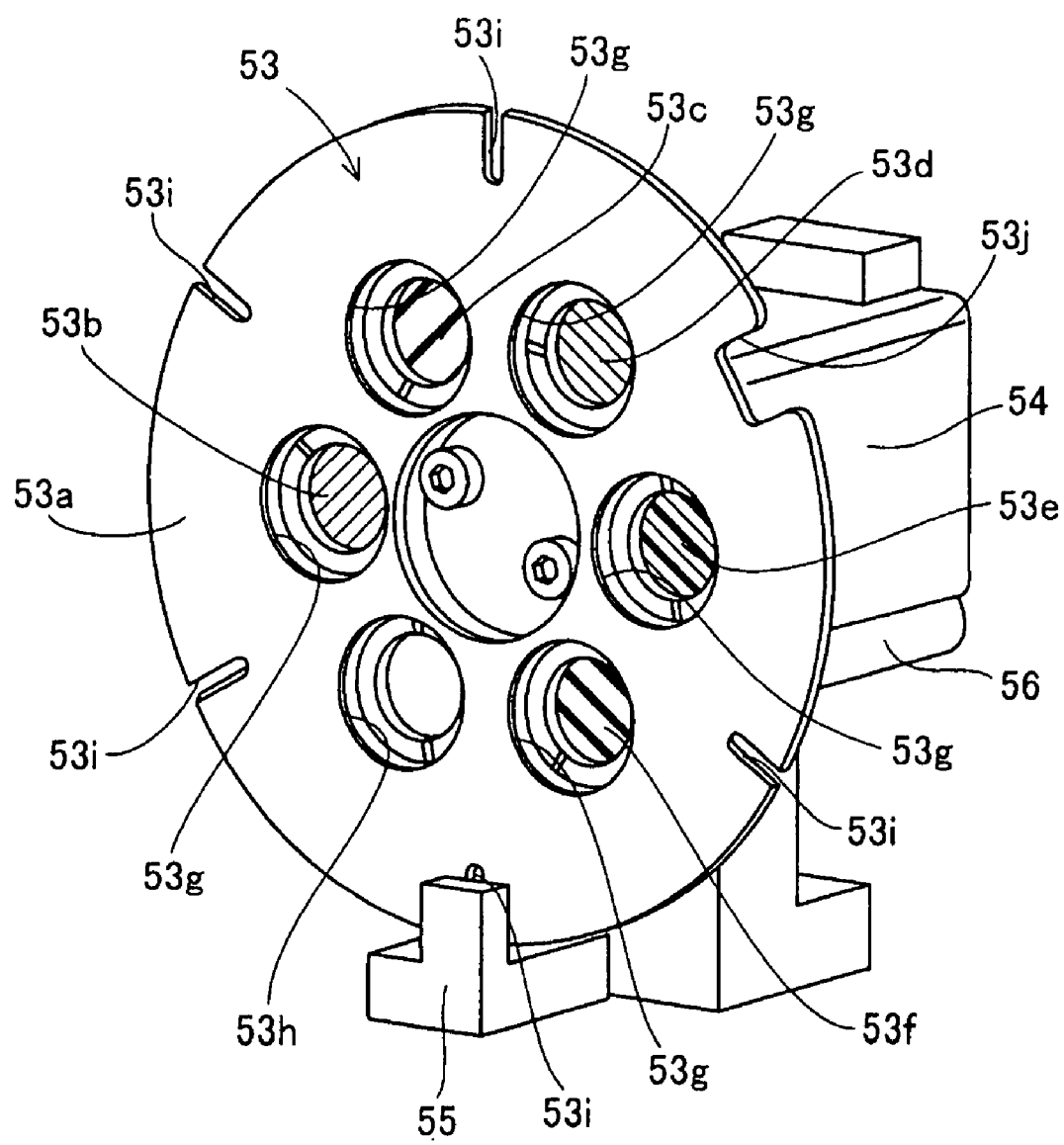
FIG. 8 is an enlarged perspective view of the filter part of the lamp unit in FIG. 6.

Furthermore, the filter part 53 of the lamp unit 50 is mounted on the motor shaft (not shown in the drawing) of the motor 54 so as to be rotatable, as shown in FIG. 8. The filter part 53 is provided with a filter plate 53a with five optical filters 53b through 53f that have respectively different light transmitting characteristics (transmission wavelengths). The filter plate 53a is provided with five holes 53g for mounting the optical filters 53b through 53f, and a hole 53h that can be blocked so as to not transmit light. The five holes 53g are respectively provided with five optical filters 53b, 53c, 53d, 53e, and 53f having respectively different light transmission characteristics (transmission wavelengths). The holes 53g and 53h are provided at predetermined angular intervals (equal spacing of 60 degrees in the present embodiment) in the direction of rotation of the filter part 53. The hole 53h is a reserve hole for installing an addition filter when necessary.

The optical filters 53b, 53c, 53d, 53e, and 53f transmit light at wavelengths of 340 nm, 405 nm, 575 nm, 660 nm, and 800 nm, respectively, and do not transmit light of different wavelength. Therefore, the light transmitted by the optical filters 53b, 53c, 53d, 53e, and 53f have wavelength characteristics of 340 nm, 405 nm, 575 nm, 660 nm, and 800 nm, respectively.

Furthermore, the filter plate 53a is provided with six slits at predetermined angular intervals (60 degree intervals in the present embodiment) in the circumferential direction. Five of the six slits are normal slits 53i, and the remaining slit is an original point slit 53j that is wider than the normal slits 53i in the direction of rotation of the filter plate 53a. The origin point slit 53j and normal slits 53i are formed at predetermined angular intervals (equal intervals of sixty degrees in the present embodiment) at intermediate angular positions between adjacent holes 53g and 53h.

Moreover, the filter part 53 is configured so as to continuously rotate when light is emitted from the lamp unit 50 to the cuvettes 152 of the of the primary dispensing table 24 and the cuvettes 152 of the cuvette loader 81, which is described later. Therefore, the five optical filters 53b through 53f having different light transmitting characteristics and the single blocked hole 53h (refer to FIG. 5) are sequentially arranged on the optical path of the light collected by the collective lenses 52a through 52c (refer to FIG. 4) in conjunction with the rotation of the filter plate 53a. Therefore, light of five different wavelengths are sequentially emitted. In the present embodiment, the filter part 53 is configured so as to rotate once per 0.1 seconds. Thus, light of five different wavelength characteristics are sequentially emitted each 0.1 seconds to the cuvette 152 of the primary dispensing table 24 and the cuvette 152 of the cuvette loader 81, which is described later. Then, five electrical signals corresponding to the five wavelengths are obtained every 0.1 seconds by the photoelectric conversion element 42 in the first optical information obtaining part 40, and five electrical signals corresponding to the five wavelengths are obtained every 0.1 seconds via the photoelectrical conversion element 82b (reference light photoelectric conversion element 82e) of the second optical information obtaining part 80.

The transmission light sensor 55 is provided to detect the passage of the origin point slit 53j and normal slits 53i in conjunction with the rotation of the filter part 53, as shown in FIG. 8. The sensor 55 detects light from the light source through the slit via the light receiving part as it passes through the origin point slit 53j and normal slits 53i, and outputs a detection signal. The detection signal output by the sensor 55 has a longer output time when light passes through the origin point slit 53j than the output signal when light passes through the normal slits 53i since the origin point slit 53j has a larger width than the normal slits 53i. Therefore, the filter part 53 can be monitored for normal rotation based on the detection signals from the sensor 55.

Figure 9:
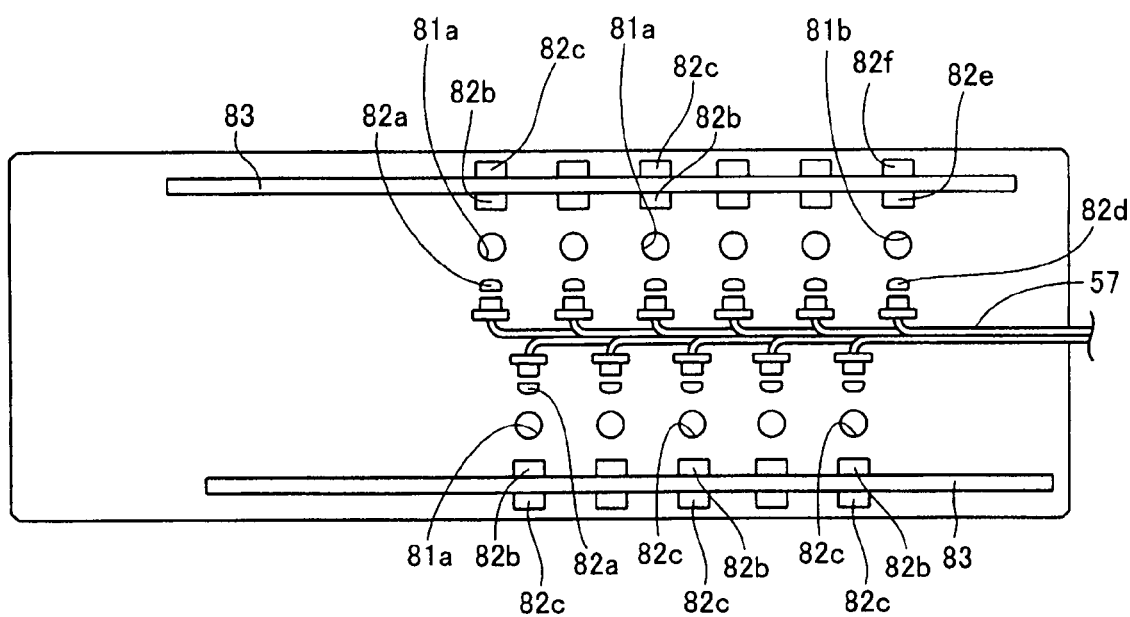
FIG. 9 is a brief illustration of the internal structure of the detection device of a second optical information obtaining part of the sample analyzer of the first embodiment in FIG. 1.

The optical fiber coupler 56 functions to direct the light that has passed through the optical filters 53b through 53f to the eleven beam splitter optical fibers 57 and the single beam splitter optical fiber 58. That is, the optical fiber coupler 56 simultaneously guides light of like quality to the eleven beam splitter optical fibers 57 and the single beam splitter optical fiber 58. Furthermore, the leading ends of the eleven beam splitter optical fibers 57 are connected to the second optical information obtaining part 80, and light from the lamp unit 50 is directed to the analysis sample within a cuvette 152 set in the second optical information obtaining part 80, as shown in FIG. 2. Specifically, the eleven beam splitter optical fibers 57 are disposed so as to supply light to ten insertion holes 81a and one reference light measurement hole 81b of the second optical information obtaining part 80 described later, as shown in FIG. 9. Moreover, unlike the eleven beam splitter optical fibers 57, the leading end of the single beam splitter optical fiber 58 is connected to the first optical information obtaining part 40, and directs the light from the lamp unit 50 to the blood sample within the cuvette 152 loaded in the holder 24a of the primary dispensing table 24, as shown in FIGS. 2 and 3. Therefore, five kinds of light having different wavelength characteristics consecutively passes through the optical filters 53b through 53f, and is supplied to the first optical information obtaining part 40 and the second optical information obtaining part 80 via the beam splitter optical fibers 57 and 58.

As shown in FIGS. 1 and 2, the reagent dispensing arm 60 is provided to mix reagent used for measuring blood coagulation time with the blood sample in the cuvette 152 by dispensing the coagulation time reagent within a reagent container (not shown in the drawings) loaded on the rotating part 20 into a cuvette 152 held in the rotating part 20. Thus, measurement sample is prepared by adding reagent used to measure coagulation time to the blood sample after optical measurement has been completed by the first optical information obtaining part 40. The cuvette transporter 70 is provided to transport the cuvette 152 between the rotating part 20 and the second optical information obtaining part 80.

As shown in FIG. 2, the optical information obtaining part 80 is configured by a cuvette loader 81, and detection unit 82 disposed below the cuvette loader 81. The cuvette loader 81 is provided with ten insertion holes 81a for inserting cuvettes 152 (refer to FIG. 2), and a single reference light measurement hole 81b for measuring a reference light and in which a cuvette is not inserted. The cuvette loader 81 has a built-in heating mechanism (not shown in the drawing) for heating a cuvette 152 loaded in the insertion holes 81a to a predetermined temperature.

The reference light measurement hole 81b is provided for monitoring the characteristics of the light emitted from the beam splitter optical fibers 57. Specifically, characteristics such as fluctuation and the like originating in the halogen lamp 51 of the lamp unit 50 are detected as electrical signals by receiving the light emitted by the beam splitting optical fibers 57 via a reference light photoelectric conversion element 82e of the direct detection unit 82. Signals corresponding to the transmission light of the measurement sample are corrected by a process of subtracting the characteristics (electrical signals) of the detected light from the signals corresponding to the transmission light of the measurement sample within the cuvette 152 inserted in the insertion hole 81a. Thus, it is possible to suppress minute differences caused by the characteristics of the light in each optical information measurement.

The detection part 82 of the second optical information obtaining part 80 is configured so as to be capable of performing optical measurements (main measurement) under a plurality of conditions on a measurement sample within a cuvette 152 inserted in the insertion hole 81a. As shown in FIGS. 7 and 8, the detection part 82 is provided with a collimator lens 82a, photoelectric conversion element 82b, and preamp 82c corresponding to each insertion hole 81a in which a cuvette 152 is inserted, and a reference light collimator lens 82d, reference light photoelectric conversion element 82e, and reference light preamp 82f corresponding to the reference light measurement hole 81b (refer to FIG. 1).

Figure 10:
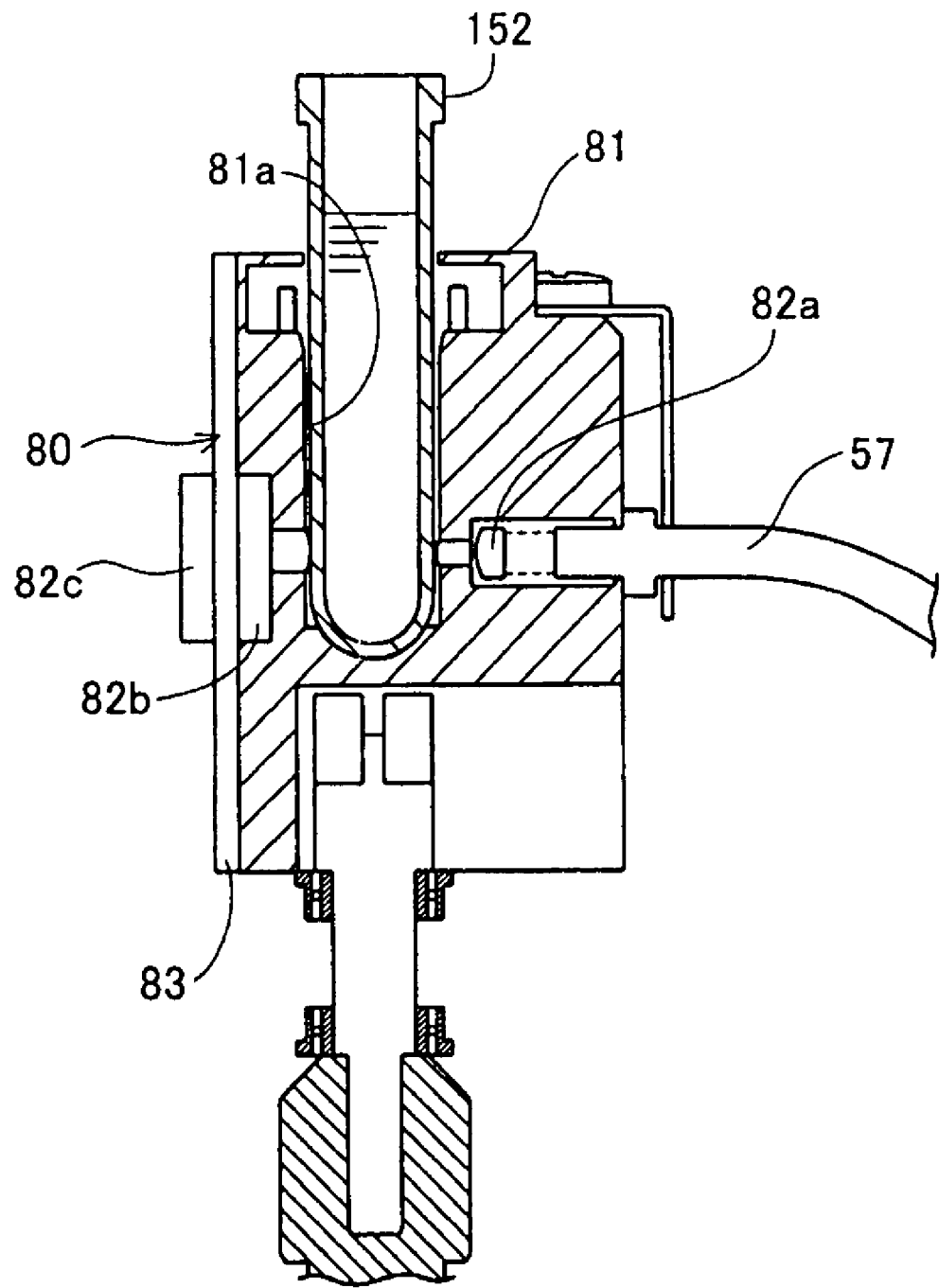
FIG. 10 is a cross section view showing the structure of the detection device of a second optical information obtaining part of the sample analyzer of the first embodiment in FIG. 1.

As shown in FIGS. 9 and 10, the collimator lens 82a is disposed between the end of the beam splitter optical fiber 57 that guides the light emitted from the lamp unit 50, and the corresponding insertion hole 81a. The collimator lens 82a is provided to render the light beams emitted from the beam splitter optical fiber 57 in parallel rays. The photoelectric conversion element 82b is mounted on the surface on the insertion hole 81a side of the base plate 83 so as to face the end of the beam splitter optical fiber 57 with the insertion hole 81a therebetween. The photoelectric conversion element 82b functions to detect the light transmitted through the measurement sample (hereafter referred to as "transmission light") when light irradiates the measurement sample within the cuvette 152 inserted in the insertion hole 81a, and outputs electric signals (analog signals) corresponding to the detected transmission light. The photoelectric conversion element 82b is disposed so as to receive five kinds of light emitted from the beam splitter optical fiber 57 of the lamp unit 50.

The preamp 82c is mounted on the opposite surface of the base plate 83 relative to the insertion hole 81a so as to amplify the electric signal (analog signal) output from the photoelectric conversion element 82b.

Figure 11:
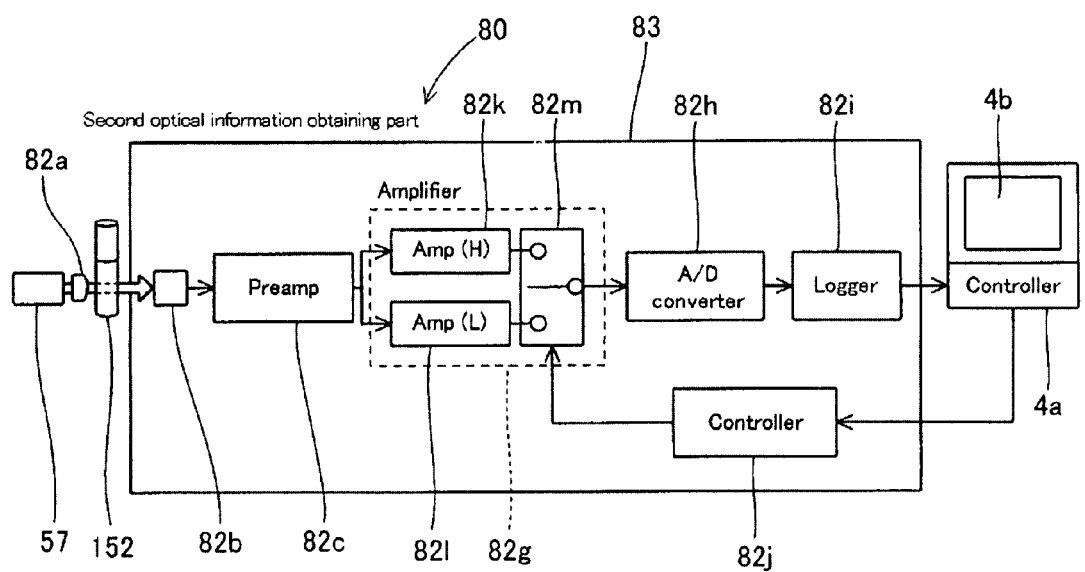
FIG. 11 is a block diagram of the second optical information obtaining part of the sample analyzer of the first embodiment in FIG. 1.

As shown in FIG. 11, the base plate 83 is provided with the photoelectric conversion elements 82b (reference light photoelectric conversion element 82e), preamps 82c (reference light preamp 82f), as well as amplifier part 82g, A/D converter 82h, logger 82i, and controller 82j. The amplifier part 82g includes amp (L) 82k with a predetermined gain (amplification factor), amp (H) 82l with a gain (amplification factor)

higher than the amp (L) 82k, and switch 82m. In the present embodiment, an electric signal from the preamp 82c is input to both the amp (L) 82k and amp (H) 82l. The amp (L) 82k and amp (H) 82l are provided to further amplify the electric signals from the preamps 82c. The switch 82m is provided to selectively either output the electric signals from the amp (L) 82k to the A/D converter 82h, or output the electric signal from the amp (H) 82l to the A/D converter 82h. The switch 82m is configured so as to perform a switching operation via the input of control signals from the controller 82j.

The A/D converter 82h is provided to convert the electric signals (analog signals) from the amplifier part 82g to digital signals. The logger 82i functions to temporarily save the digital signal data from the A/D converter 82h. The logger 82i is electrically connected to the controller 4a of the control device 4, and sends the digital signal data obtained in the second optical information obtaining part 80 to the controller 4a of the control device 4.

As shown in FIGS. 1 and 2, the rush sample acceptor 90 is provided to perform a sample analysis process on blood sample requiring immediate processing. The rush sample acceptor 90 is capable of performing an interrupt on behalf of a rush sample when there is an on-going sample analysis process being performed on a blood sample supplied from the transport device 3. The cuvette disposal 100 is provided to dispose of cuvettes from the rotating part 20. As shown in FIG. 2, the cuvette disposal 100 is configured by a cuvette waste part 101, disposal hole 102 provided at predetermined spacing from the cuvette waste part 101 (refer to FIG. 1), and waste box 103 provided below the disposal hole 102. The cuvette waste part 101 is provided to move a cuvette 152 from the rotating part 20 to the waste box 103 via the disposal hole 102 (refer to FIG. 1). A fluid provider 110 is provided to supply a fluid such as cleaning liquid to a nozzle provided on each dispensing arm during the shutdown process of the sample analyzer 1.

The control device 4 (refer to FIG. 1) is configured by a personal computer (PC), and includes a controller 4a that includes a CPU, ROM, RAM and the like, a display 4b, and a keyboard 4c. The display 4b is provided to display information relating to interference substances (hemoglobin, chyle (lipids), and bilirubin) present in the blood sample, and analysis results (coagulation time) obtained by analyzing the digital signal data received from the second optical information obtaining part 80.

Figure 12:
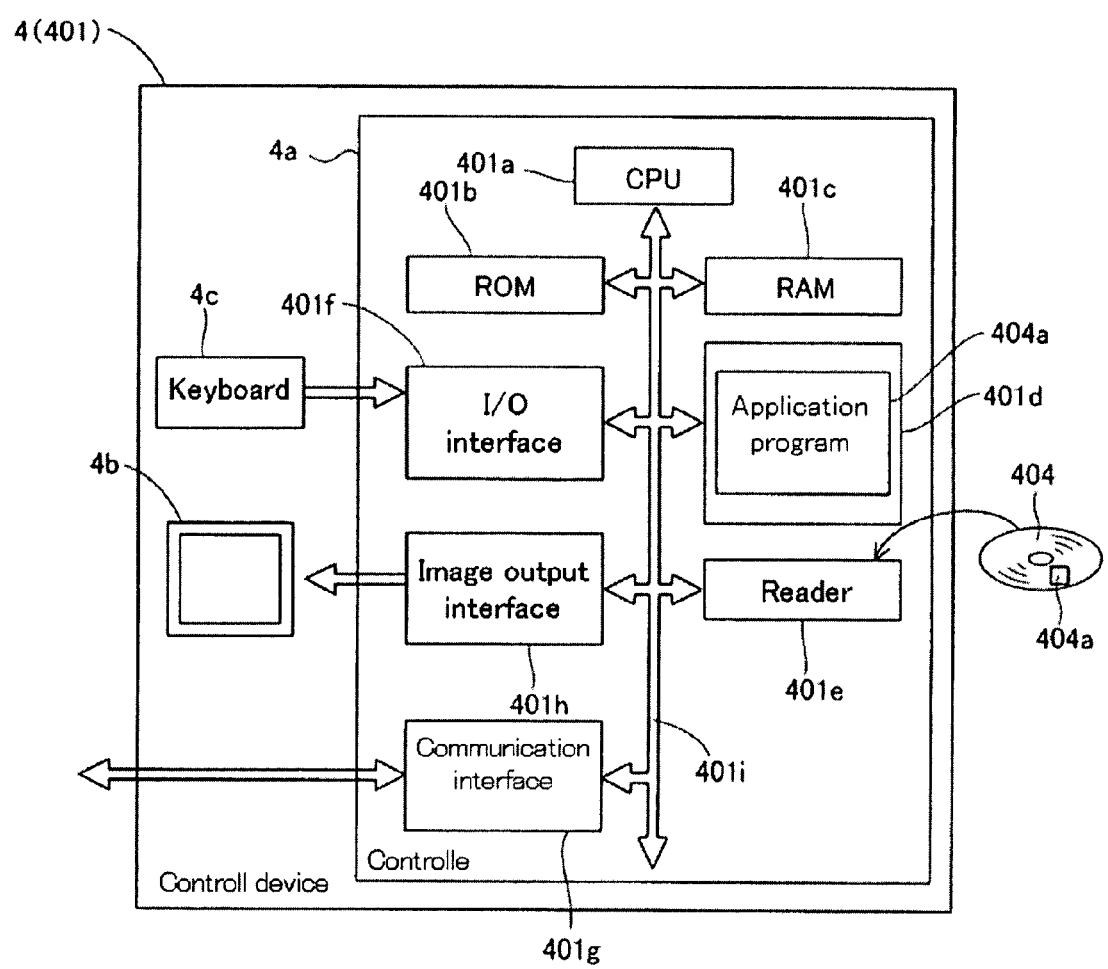
FIG. 12 is a block diagram of the controller of the sample analyzer of the first embodiment in FIG. 1.

The structure of the control device 4 is described below. As shown in FIG. 12, the controller 4a is mainly configured by a controller 4a, display 4b, and keyboard 4. The controller 4a is mainly configured by a CPU 401a, ROM 401b, RAM 401c, hard disk 401d, reading device 401e, I/O interface 401f, communication interface 401g, and image output interface 401h. The CPU 401a, ROM 401b, RAM 401c, hard disk 401d, reading device 401e, I/O interface 401f, communication interface 401g, image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401a when these computer programs are being executed.

The hard drive 401d contains various installed computer programs to be executed by the CPU 401a such as an operating system and application programs and the like, and data used in the execution of these computer programs. Also installed on the hard disk 401d is the application program 404a used for blood coagulation time measurement the present embodiment.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a used for blood coagulation time measurement; the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over an electric communication line by means of the electric communication line (wire line or wireless). For example, the application program 404a may be stored on the hard disk of a server computer connected to the internet, such that the computer 401a can access the server computer and download the application program 404a, and then install the application program 404a on the hard disk 401d.

Also installed on the hard disk 401d is an operating system providing a graphical user interface, such as, for example, Windows® of Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user can input data in the computer 401 using the keyboard 4c.

The communication interface 401g is, for example, and Ethernet® interface. The computer 401 can send and receive data to and from the detection device 2 using a predetermined communication protocol via the communication interface 401g.

The image output interface 401h is connected to the display 4b configured by an LCD, CRT or the like, such that image signals corresponding to the image data received from the CPU 401 can be output to the display 4b. The display 4b displays an image (screen) in accordance with the input image signals.

The application program 404a for blood coagulation time measurement installed on the hard disk 401d of the control device 4a measures the coagulation time of measurement samples using the amount of transmission light (digital signal data) of the measurement sample received from the second optical information obtaining part 80 of the detection device 2. The blood coagulation time is the time from the moment the blood coagulation measurement reagent is added to a blood sample in a cuvette 152 until the measurement sample (with the added reagent for measuring coagulation time) loses flowability (coagulation time). The coagulation reaction in which the measurement sample loses flowability is a reaction that changes fibrinogen within the sample to fibrin via the added coagulation reagent. In the sample analyzer 1 of the present embodiment, the coagulation reaction dependent on the amount of fibrinogen within the blood sample is confirmed by the amount of change of the transmission light of the measurement sample (the difference between the amount of transmission light before the reaction and the amount of transmission light after the reaction).

Figure 13:
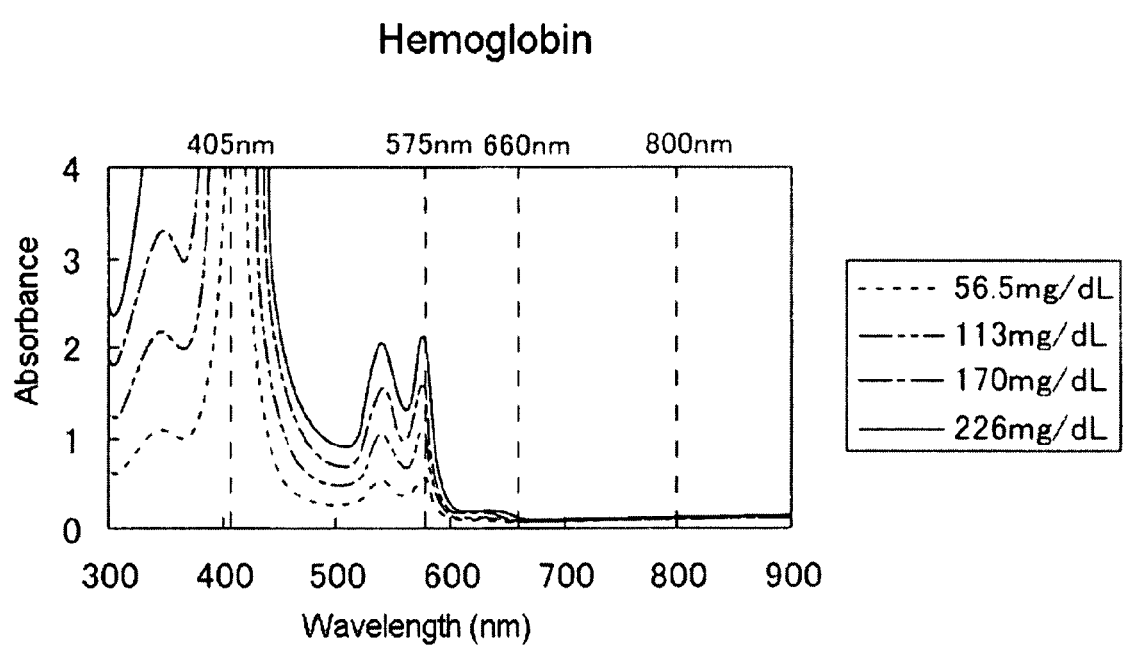
FIG. 13 is a graph of the absorption spectrum of hemoglobin.
Figure 14:
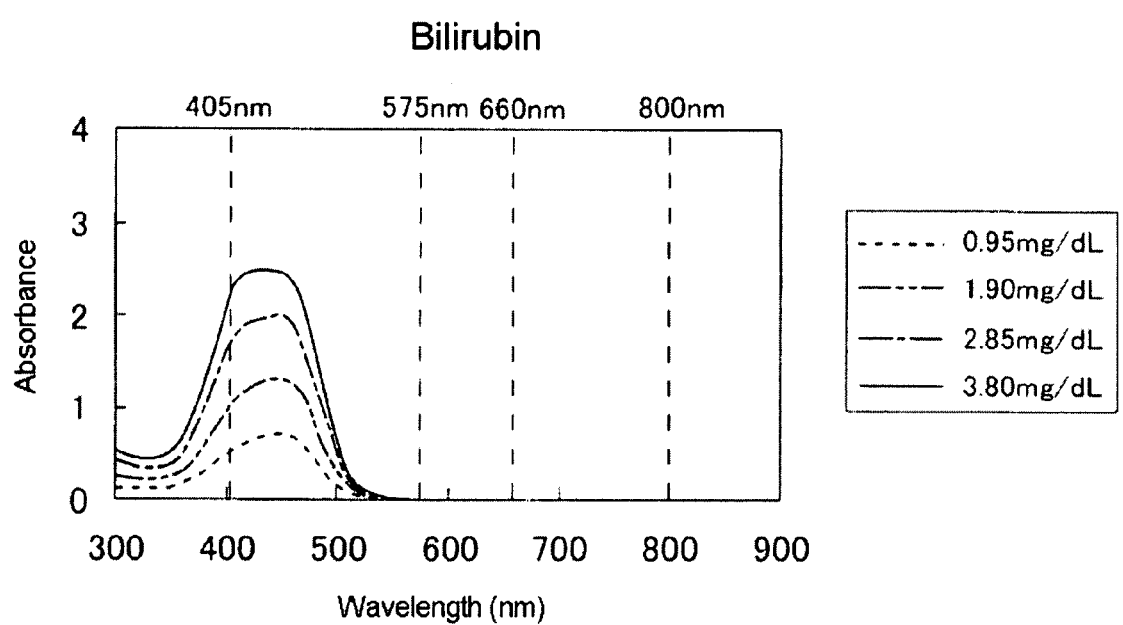
FIG. 14 is a graph of the absorption spectrum of bilirubin.
Figure 15:
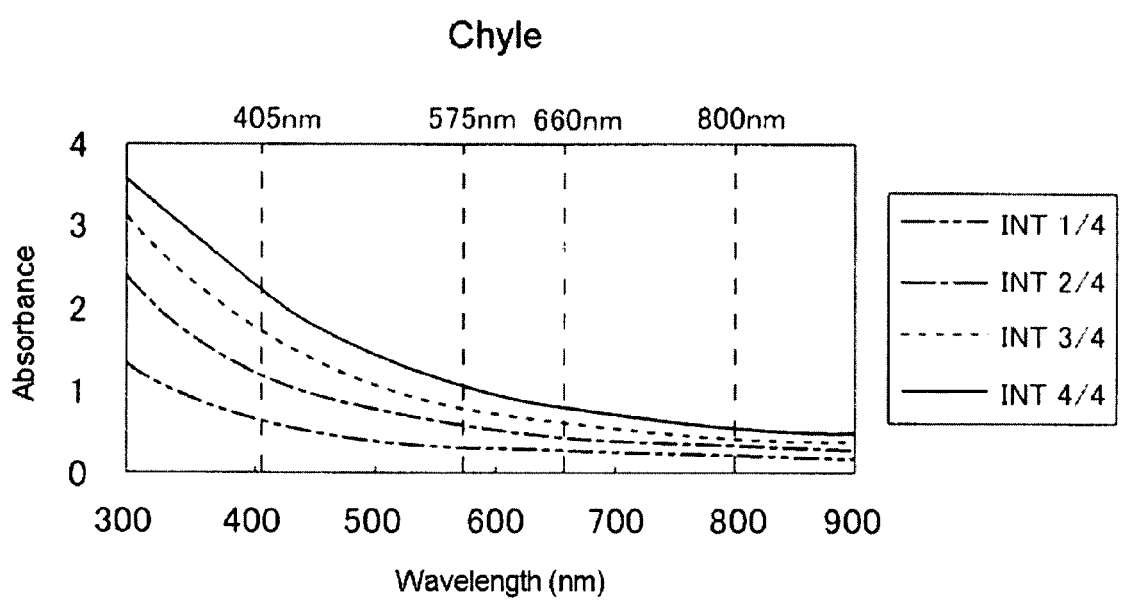
FIG. 15 is a graph of the absorption spectrum of chyle.
Figure 16:
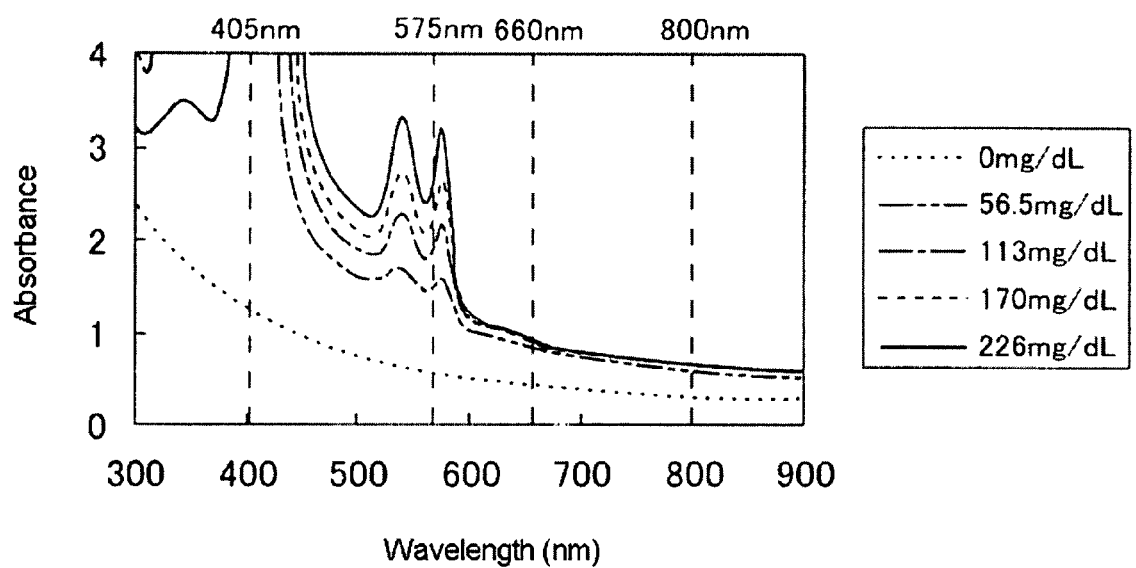
FIG. 16 is a graph of the absorption spectrum when hemoglobin and chyle are added.
Figure 17:
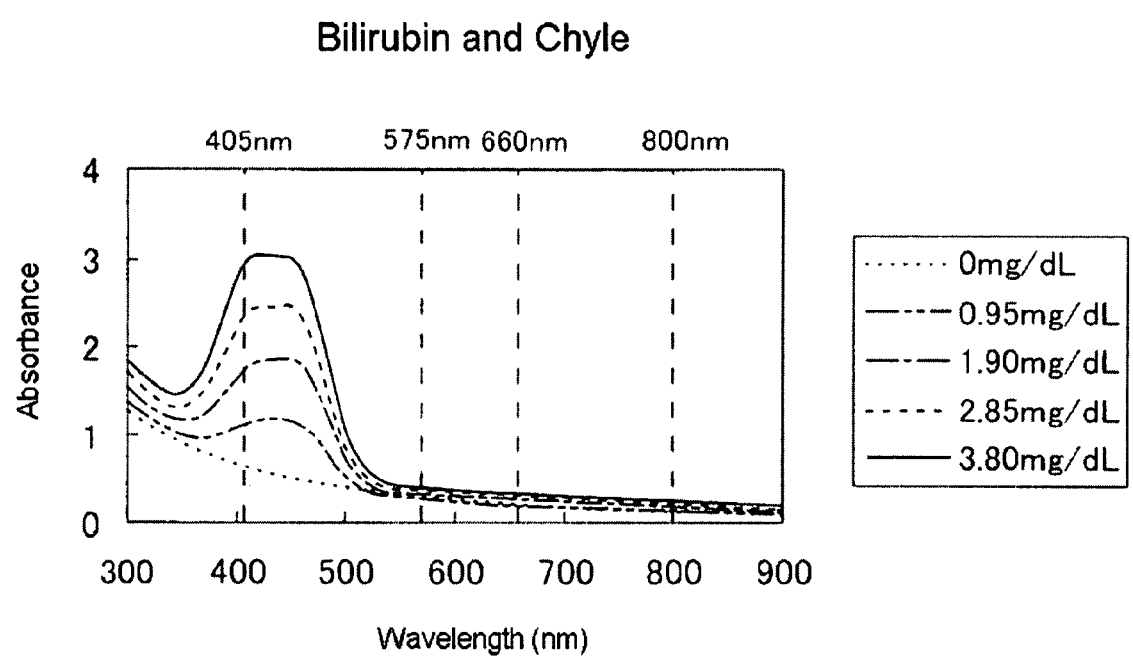
FIG. 17 is a graph of the absorption spectrum when bilirubin and chyle are added.

The light at wavelengths of 405 nm, 575 nm, 660 nm, and 800 nm emitted from the optical fiber 58 and directed to the first optical information obtaining part 40 are described in detail below with reference to FIGS. 13 through 18. The light at a wavelength of 800 nm and light at a wavelength of 660 nm are absorbed by chyle but are essentially not absorbed by hemoglobin and bilirubin, as shown in FIGS. 13 through 15. Light at a wavelength of 575 nm is absorbed by hemoglobin and chyle but essentially not absorbed by bilirubin. Light at a wavelength of 405 nm is absorbed by hemoglobin, bilirubin, and chyle. It can be understood from FIG. 15 that chyle absorbs light from the low wavelength range of 405 nm to the high wavelength range of 800 nm. Therefore, it is understood that the baseline of the hemoglobin absorbance spectrum is elevated by the amount of chyle absorbance (light absorbed by chyle) when chyle is added to hemoglobin, as shown in FIG. 16, compared to the hemoglobin absorbance spectrum shown in FIG. 13. Moreover, it is also understood that the baseline of the bilirubin absorption spectrum is elevated by the amount of chyle absorbance when chyle is added to bilirubin, as shown in FIG. 17, compared to the bilirubin absorbance spectrum shown in FIG. 14.

Figure 18:
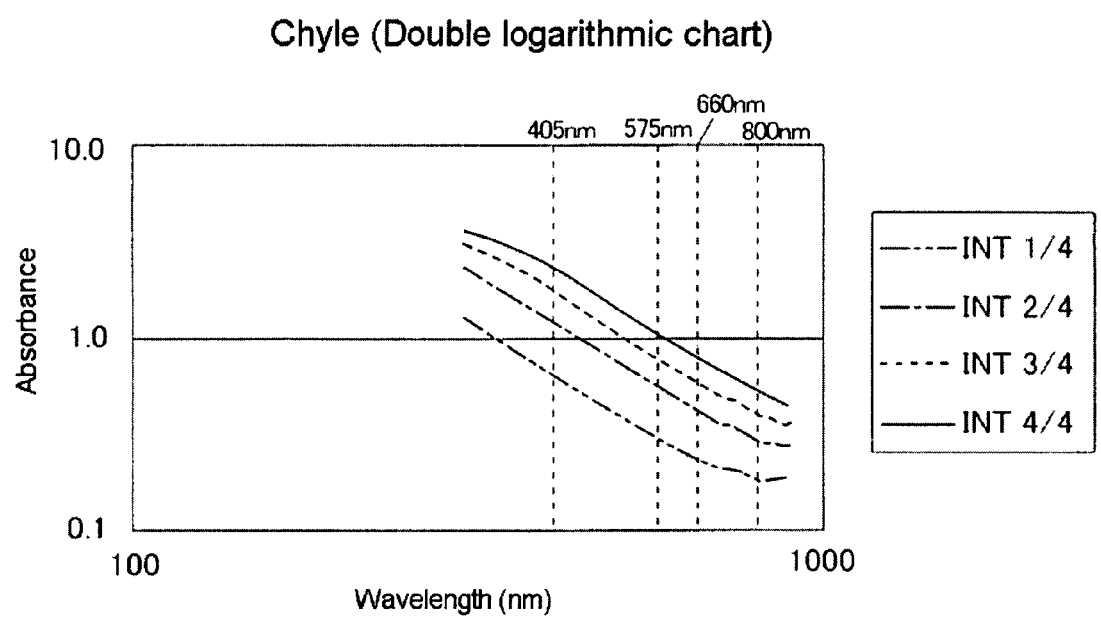
FIG. 18 is a graph of the chyle absorption spectrum plotted on a double logarithmic chart.

As shown in FIG. 18, the chyle absorbance spectrum is known to be a substantially linear expression when the chyle absorbance spectrum shown in FIG. 15 is plotted as a double logarithmic chart. That is, the linear expression can be represented by equation (1) below using constants a and b.

$$\log 10Y = a \log 10X + b \tag{1}$$

(where Y represents absorbance, and X represents wavelength.)

Since the sample (plasma) being measured by the sample analyzer of the present embodiment contains interference substances (chyle, hemoglobin, and bilirubin), light absorbed by the sample measured using a wavelength of 405 nm is conducive to chyle absorbance, hemoglobin absorbance, and bilirubin absorbance. Furthermore, absorbance by a sample measured at a wavelength of 575 nm is conducive to chyle absorbance and hemoglobin absorbance and not conducive to bilirubin absorbance. Absorbance by a sample measured at wavelengths of 660 nm and 800 nm are conducive only to chyle absorbance and not conducive to hemoglobin absorbance and bilirubin absorbance. Therefore, it is possible to determine the extent, if any, of the influence the chyle content in a sample has on a measurement by analyzing the absorbance of the sample measured using light at a wavelength of 660 nm and/or 800 nm. Moreover, it is possible to determine the extent, if any, of the influence the hemoglobin content in a sample has on a measurement by eliminating the chyle influence (absorbance) from the absorbance of the sample measured using light at a wavelength of 575 nm. Thus, it is possible to determine the extent of the influence the bilirubin content in a sample has on a measurement by eliminating the chyle influence (absorbance) and hemoglobin influence (absorbance) of the sample from the absorbance of the sample measured using light at a wavelength of 405 nm.

Figure 19:
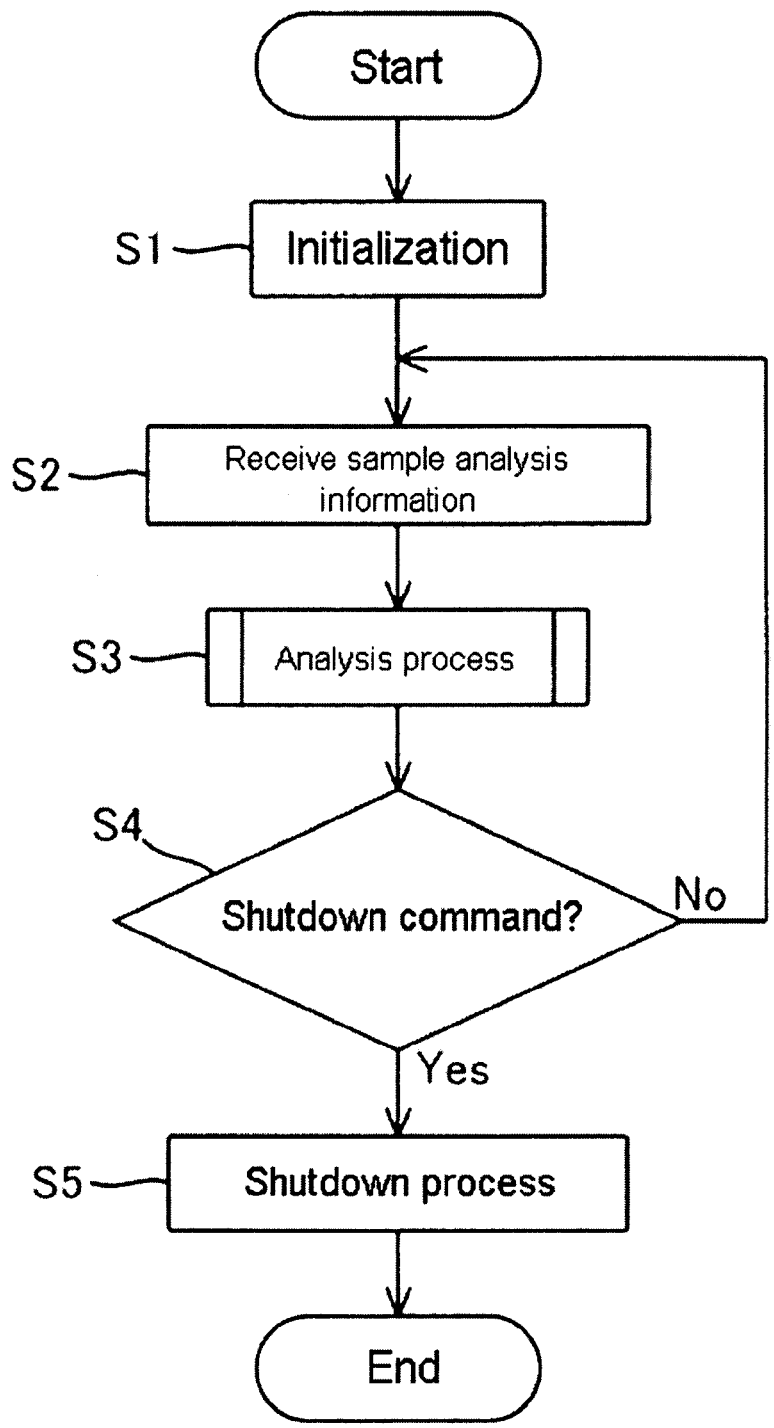
FIG. 19 is a flow chart showing the control flow of the controller of the control device of the sample analyzer of the first embodiment in FIG. 1.

FIG. 19 is a flow chart showing the control flow of the controller of the control device in the sample analyzer of the first embodiment shown in FIG. 1. FIG. 20 shows a sample analysis table output to the display of the control device of the sample analyzer of the first embodiment shown in FIG. 1. The sample analysis process performed by the sample analyzer 1 of the first embodiment of the present invention is described below with reference to FIG. 1 and FIGS. 19 and 20.

First, the sample analyzer 1 is started and initialized when a user turns ON the respective power sources of the control device 4 and detection device 2 of the sample analyzer 1 shown in FIG. 1. During initialization, the detection device 2 is initialized and the software of the control device 4 is initialized by operations that return the devices for transporting the cuvettes 152 and each dispensing arm to their starting positions (step S1). Then a user inputs sample analysis information. That is, a user uses the keyboard 4c of the control device 4 to enter the sample number and information in the columns of the measurement items in the sample analysis table (refer to FIG. 20) output to the display 4b of the control device 4. The controller 4a receives the input sample information (step S2), and the input sample information is saved in the controller 4a.

The sample analysis information can not only be entered using the keyboard 4c, the user also can adhere a barcode label beforehand to the test tube 150 containing the sample such that the controller 4a may acquire the sample analysis information by reading the barcode using a barcode reader or the like. In this case, to read the data on the barcode label, the controller 4a accesses a host computer for managing sample analysis information and the like to obtain sample analysis information corresponding to the data read from the barcode label. Thus, the controller 4a may obtain the sample analysis information without the user inputting the information.

The sample analysis table shown in FIG. 20 is described below. A number ("000101") for identifying individual samples is entered in the sample number column. A code ("PT" and "ATIII") representing measurement items to be performed on the sample are entered in the measurement item column associated with the sample number. The measurement items "PT" (prothrombin time) and "APTT" {active partial thromboplastin time} are measured using a coagulation time method. The measurement item "ATIII" (anti thrombin III) is measured using a synthetic substrate method. The measurement item "FDP" (fibrin degradation product) is measured using an immunoturbidity method (hereinafter, optical measurements performed using a coagulation time method, synthetic substrate method, or immunoturbidity method are referred to simply as "main measurement").

An item for secondary dispensing flag, an item for interference substance flag that includes three sub items of bilirubin, hemoglobin, and chyle, an item for wavelength change flag, and item for high gain flag are also provided in the sample analysis table. Although each of these items is set to OFF ([0] is displayed in the table) during initialization in step S1, these items can be set to ON ([1] is displayed in the table) in accordance with analysis results of optical information from the first optical information obtaining part 40. FIG. 20 shows each of these items with the status set at OFF. The ON status of the secondary dispensing flag indicates the secondary dispensing of the sample. The ON status of the interference substance flags for hemoglobin, bilirubin, and chyle indicate a high probability that the sample will be influenced by hemoglobin, bilirubin, or chyle. The ON status of the wavelength change flag indicates the analysis of optical information obtained using light of a different wavelength (800 nm) than the light of the normal wavelength (660 nm). The ON status of the high gain flag indicates analysis of optical information obtained at a higher gain (amplification factor) than the normal gain (amplification factor) of the amp 45e.

The user inputs an analysis process start command after the sample number and measurement items have been input, and with the reagent container (not shown in the drawing) containing the reagent necessary for the preparation of the measurement sample, and the test tubes 150 containing the samples disposed at predetermined positions. Thus, the analysis process is started in step S3. After the predetermined sample analysis process has been completed, a determination is made in step S4 as to whether or not a shutdown command has been input to the sample analyzer 1. When it is determined in step S4 that a shutdown command has not been input to the sample analyzer 1, the routine returns to step S2 and the user inputs other sample analysis information. When it is determined in step S4 that a command to shutdown the sample analyzer 1 has been input, the shutdown process is performed in step S5. Thus, after cleaning has been performed by the nozzle provided on each dispensing arm shown in FIG. 1, the power sources of the detection device 2 and the control device 4 of the sample analyzer 1 are automatically turned OFF and the sample analysis process of the sample analyzer 1 is completed.

Figure 21:
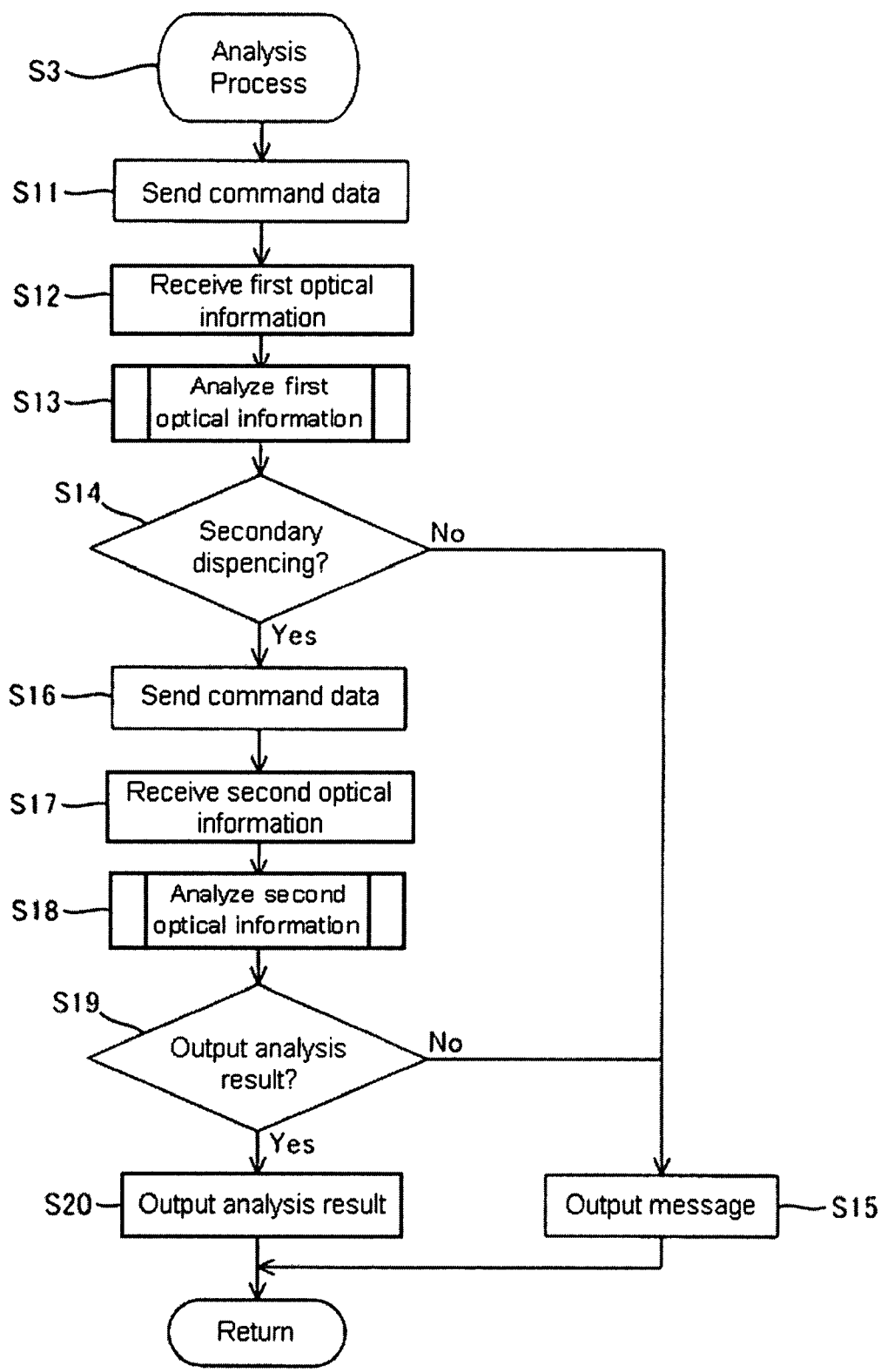
FIG. 21 is a flow chart showing the sequence of the sample analysis operation of the sample analyzer of the first embodiment in FIG. 1.

FIG. 21 is a flow chart showing details (subroutines) of the analysis process performed by the controller 4a of the first embodiment shown in step S3 of FIG. 19. The analysis process performed by the controller 4a in step S3 of FIG. 19 is described in detail below. Data specifying the measurement of the first optical information are transmitted to the detection device 2 to specify the measurement when the user inputs the start of the analysis process (step S11). Thus, when measurement of the first optical information has been specified, the transport device 3 shown in FIG. 2 first transports the rack 151 on which the test tube 150 containing the sample is loaded. Thus, the rack 151 is transported from the rack set region 3a to a position corresponding to the aspirating position 2a of the detection device 2. Then, a predetermined amount of the sample is aspirated from the test tube 150 via the nozzle 35 of the sample dispensing arm 30 (refer to FIG. 1). Then, the sample dispensing arm 30 is actuated and the nozzle of the sample dispensing arm 30 is moved above the cuvette 152 held in the primary dispensing table 24 of the rotating part 20. Next, the primary dispensing process is performed by discharging the sample from the nozzle of the sample dispensing arm 30 into the cuvette 152 on the primary dispensing table 24.

Thereafter, the primary dispensing table 24 is rotated and the cuvette 152 into which the sample was dispensed is transported to a position at which sample measurement can be performed by the first optical information obtaining part 40. Thus, optical information is obtained from the sample by optically measuring the sample via the first optical information obtaining part 40. Specifically, light of different wavelengths (340 nm, 405 nm, 575 nm, 660 nm, 800 nm), which have passed through the sample within the cuvette 152 maintained in the holder 24a (refer to FIG. 4) of the primary dispensing table 24, are sequentially detected by the photoelectric conversion element 42. Then, the electrical signals converted by the photoelectric conversion element 42 are amplified by the preamp 45a (refer to FIG. 5) and the amplifier 45e, and finally converted to digital signals by the A/D converter 45c. Thereafter, the controller 45d inputs the digital signals to the controller 4a of the control device 4, and the controller 4a receives the first optical information (step S12). In step S13, the first optical information of the sample is analyzed by the controller 4a of the control device 4.

In step S14, the controller 4a of the control device 4 (refer to FIG. 1) determines whether or not the sample in the cuvette 152 maintained in the holder 24a of the primary dispensing table 24 is an object for secondary dispensing based on the analysis result in step S13. When it has been determined that the sample in the cuvette 152 maintained in the holder 24a of the primary dispensing table 24 is not an object for secondary dispensing in step S14, a message with the following content "High reliability analysis unlikely due to severe influence by interference substance (at least one substance selected from among bilirubin, hemoglobin, and chyle (including difficulty arising from specific interference substance)) among the sample content" is output to the display 4b of the control device 4 (refer to FIG. 1). However, when it has been determined that the sample in the cuvette 152 maintained in the holder 24a of the primary dispensing table 24 is an object for secondary dispensing in step S14, the data specifying the second optical information measurement (main measurement) are transmitted to the detection device 2 in step S16 to specify the measurement. A predetermined amount of sample is aspirated from the cuvette 152 maintained by the holder 24a of the primary dispensing table 24 via the nozzle of the sample dispensing arm 30. Thereafter, the secondary dispensing process is performed by discharging a predetermined amount of sample from the nozzle of the sample dispensing arm 30 into a plurality cuvette 152 of the secondary dispensing table 23.

Then, the reagent dispensing arm 60 is actuated and reagent in the reagent container (not shown in the drawing) loaded in the reagent tables 21 and 22 are added to the sample in the cuvette 152 on the secondary dispensing table 23. Thus, a measurement sample is prepared. The cuvette transporter 70 then moves the cuvette 152 on the secondary dispensing table 23 containing the measurement sample to the insertion hole 81a of the cuvette loader 81 of the second optical information obtaining part 80.

A plurality (ten kinds) of optical information are obtained from the measurement sample by optically measuring the measurement sample within the cuvette 152 under a plurality of conditions via the detection unit 82 of the second optical information obtaining part 80. Specifically, the cuvette 152 inserted in the insertion hole 81a of the cuvette loader 81 is first heated to a predetermined temperature by a heating device (not shown in the drawing). Thereafter, light from the optical fiber 57 of the lamp unit 50 (refer to FIG. 7) is emitted to the cuvette 152 on the cuvette loader 81. Light of five different wavelengths (340 nm, 405 nm, 575 nm, 660 nm, 800 nm) are periodically emitted from the optical fiber 57 in conjunction with the rotation of the filter part 53 (refer to FIG. 8). The light of each wavelength emitted from the optical fiber 57 that has passed through the cuvette 152 and the measurement sample in the cuvette 152 are sequentially detected by the photoelectric conversion element 82b. Electrical signals corresponding to the light of five different wavelengths converted by the photoelectric conversion element 82b are sequentially input to the amplifier 82g after they have been amplified by the preamp 82c.

In the amplifier 82g, the electrical signals corresponding to the light of five different wavelengths received from the preamp 82c are input to both the amp (H) 82k that has a high gain factor and the amp (L) 82l that has a normal gain factor. After the electrical signals amplified by the amp (H) 82k have been output to the A/D converter 82h, the electrical signals amplified by the amp (L) 82l are output to the A/D converter 82h by the controller 82j controlling the switch 82m. The switch 82m is repeatedly switched in conjunction with the timing of the rotation of the filter part 53 of the lamp unit 50. Thus, in the amplifier 82g, the electrical signals corresponding to light of five different wavelengths are amplified by two different amplification factors, such that a total of ten different electrical signals are repeatedly input to the A/D converter 82h. These ten electric signals are converted to digital signals by the A/D converter 82h and the digital signals are temporarily stored in the logger 82i, and subsequently these digital signals are sequentially transmitted to the controller 4a of the control device 4. The controller 4a receives the second optical information (step S17).

In step S18, optical information determined to be appropriate for the analysis are analyzed by the controller 4a of the control device 4 from among a plurality (ten kinds) of optical information corresponding to the measurement sample from the second optical information obtaining part 80 based on the analysis results of the optical information (digital signal data) from the first optical information part 40 which was obtained beforehand. In step S19, the controller 4a of the control device 4 determines whether or not the measurement sample analysis results can be output in step S19. When it has been determined in step S19 that the measurement sample analysis results analyzed in step S18 can not be output, a message with a content indicating "high reliability analysis is unlikely" is output in step S15 to the display 4b of the control device 4 (refer to FIG. 1). The determination to jump from step S19 to step S15 is provided in the present embodiment when the analysis results of electrical signal data for light at the 800 nm wavelength in the measurement items using the coagulation time method can not be output. When step S19 determines that the measurement sample analysis results of step S18 can be output, the measurement sample analysis results are output to the display 4b of the control device 4 in step S20.

In step S14, when it has been determined that the reliable analysis results were not obtained at the initially set wavelength based on analysis results of the first optical information, it may also be determined to perform the measurement at a wavelength other than the initially set wavelength. After the measurement and analysis has been performed on the second optical information (main measurement) when measured at a different wavelength, a determination is made as to whether or not the analysis results can be output. The analysis results are output to the display 4b (step S20) when the analysis results can be output, and when they can not, a message with a content indicating "high reliability analysis is unlikely" is output to the display 4b of the control device 4 (step S15).

FIGS. 22 through 25 are flow charts illustrating details (subroutines) of the analysis process of the optical information from the first optical information obtaining part 40 in the first embodiment shown in step S13 of FIG. 21. The method of the analysis process for the first optical information in step S113 of FIG. 21 is described in details below with reference top FIGS. 22 through 25.

Figure 22:
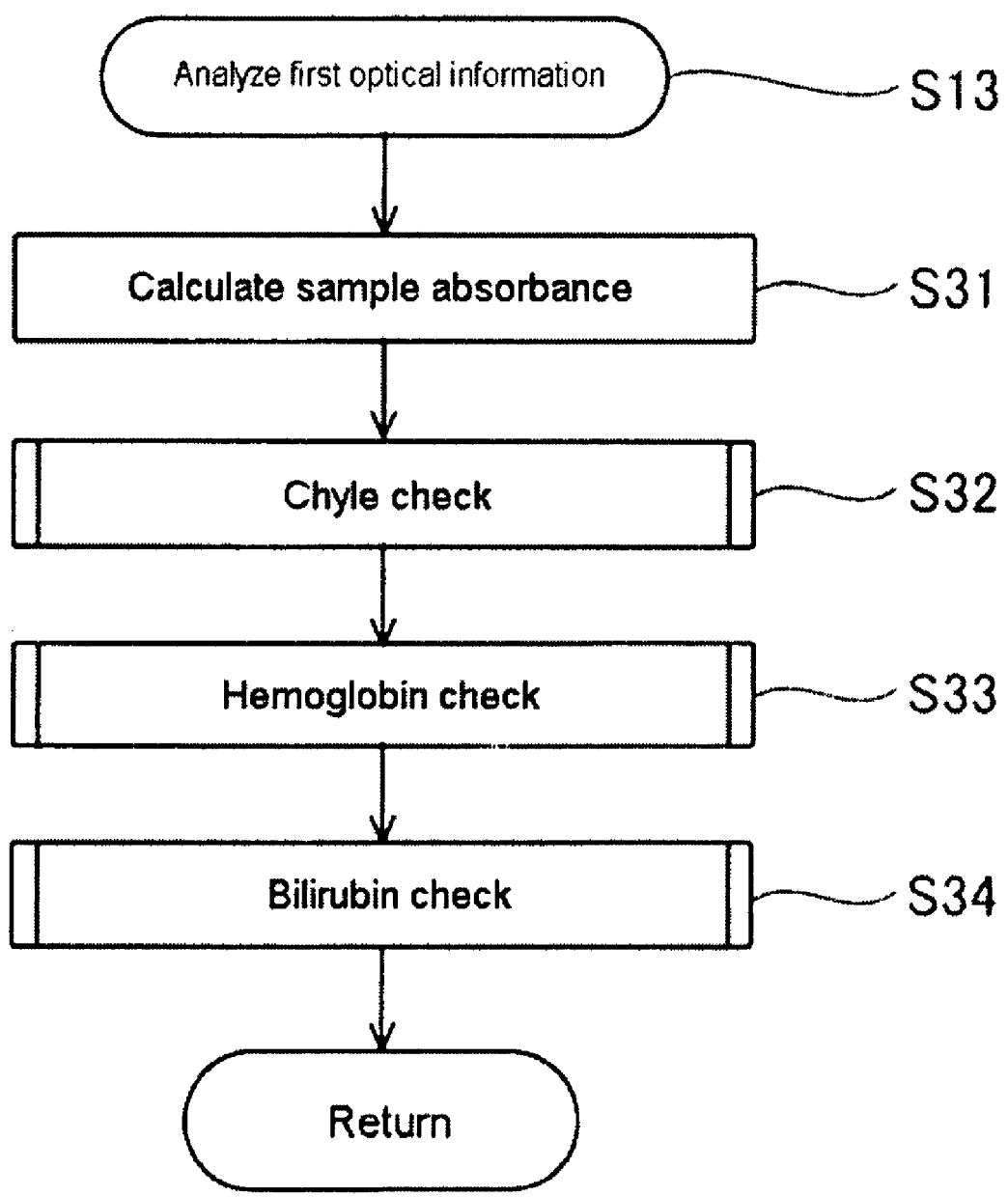
FIG. 22 is a flow chart showing the analysis sequence of the first optical information obtaining part of the sample analyzer of the first embodiment in FIG. 1.

In the present embodiment, the absorbance by the sample at each wavelength 405 nm, 575 nm, 660 nm, and 800 nm is calculated in step S31 of FIG. 22 when the sample optical information (light transmittance) obtained by the first optical information obtaining part 40 is input to the controller 4a of the control device 4. The absorbance A is a value determined by equation (2) below using the light transmittance T (%) of the sample.

$$A = -\log 10(T/100) \quad (2)$$

Figure 23:
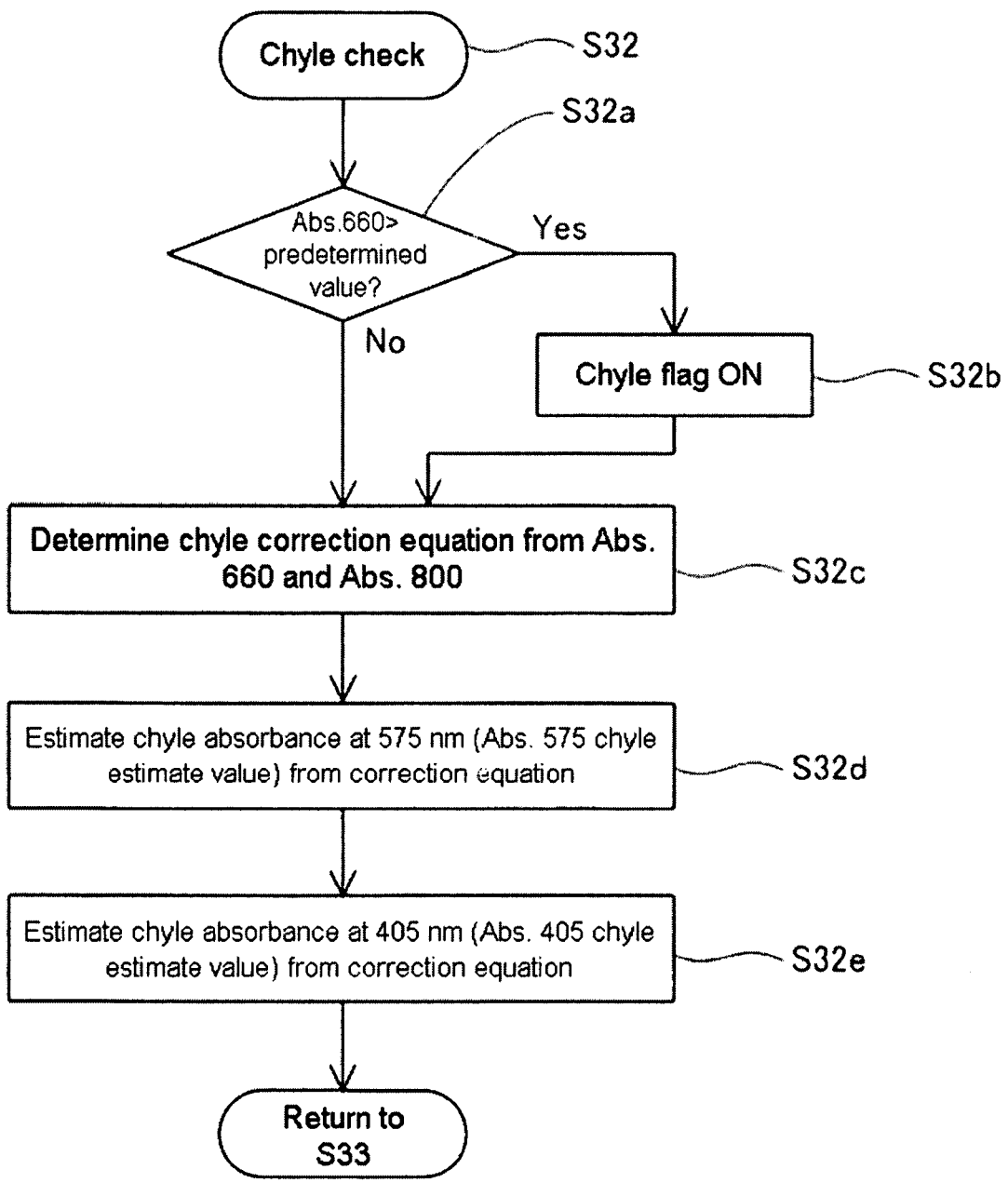
FIG. 23 is a flow chart showing the interference substance (chyle) check subroutine in FIG. 22.

A chyle check is performed in step S32. Specifically, a determination is made in step S32a as to whether or not the sample absorbance of 660 nm wavelength light (Abs. 660) is greater than a threshold value, as shown in FIG. 23. When it is determined in step S32a that the sample absorbance of 660 nm wavelength light (Abs. 660) is greater than a threshold value, it is determined in step S32b that chyle is present in the sample, and the chyle flag on the sample analysis table (refer to FIG. 20) is reset from OFF ([0] in the table) to ON ([1] in the table). In contrast, when it is determined in step S32a that the sample absorbance of 660 nm wavelength light (Abs. 660) is less than a threshold value that the sample chyle content will not influence the measurement, and the chyle flag on the sample analysis table remains OFF ([0] in the table). Although the sample chyle content is measured using light at a wavelength of 660 nm in the present embodiment, the sample chyle content may also be measured using 800 nm light.

In step S32c of the present embodiment, the chyle is corrected using the sample absorbance at the 660 nm wavelength (Abs. 660) and the sample absorbance at the 800 nm wavelength (Abs. 800). Specifically, the wavelength (X=660) and absorbance (Y=Abs. 660) are substituted in equation (1) to derive equation 1(b), and the wavelength (X=800) and absorbance (Y=Abs. 800) are substituted in equation (1) to derive equation (1b) below.

$$\log 10 \text{Abs. } 600 = a \log 10 660 + b \quad (1a)$$

$$\log 10 \text{Abs. } 800 = a \log 10 800 + b \quad (1b)$$

Then the constants a and b are calculated for equations (1a) and (1b) to derive the chyle correction equation (3) to obtain the chyle absorbance y at a predetermined wavelength x.

$$\log 10y = a \log 10x + b \quad (3)$$

In step S32d, a chyle absorbance estimation value (Abs. 575 chyle estimation value) is calculated relative to light at 575 nm wavelength from the chyle correction equation (3) determined in step S32c. That is, a chyle absorbance estimation value (Abs. 575 chyle estimation value) is calculated relative to light at 575 nm wavelength by substituting the wavelength (x=575 nm) in the correction equation (3).

In step S32e, similar to step S32d, a chyle absorbance estimation value (Abs. 405 chyle estimation value) is calculated relative to light at 405 nm wavelength from the chyle correction equation (3) determined in step S32d. That is, a chyle absorbance estimation value (Abs. 405 chyle estimation value) is calculated relative to light at 405 nm wavelength by substituting the wavelength (x=405 nm) in the correction equation (3).

Figure 24:
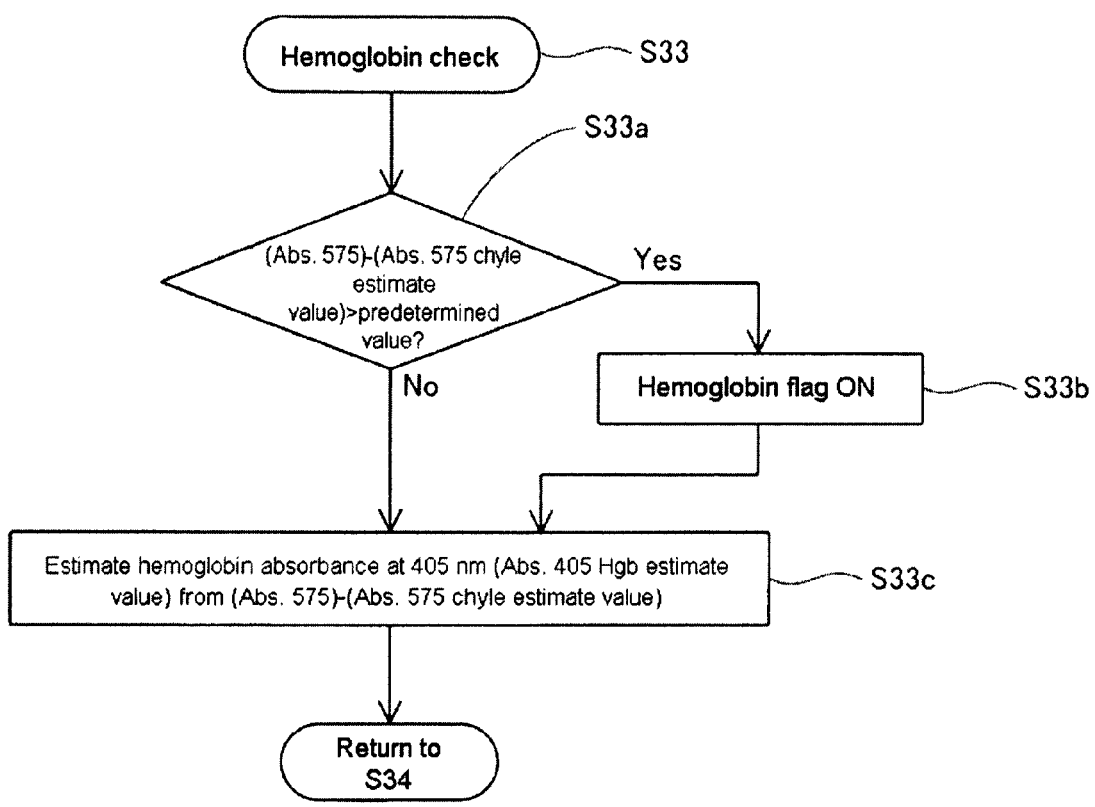
FIG. 24 is a flow chart showing the interference substance (hemoglobin) check subroutine in FIG. 22.

A hemoglobin check is performed in step S33 shown in FIG. 22. Specifically, in step S33a, the sample absorbance (Abs. 575 nm) relative to 575 nm light is corrected to estimate the hemoglobin absorbance relative to light at a wavelength of 575 nm by subtracting the chyle absorbance estimation value (Abs. 575 chyle absorbance estimation value) relative to 575 nm wavelength light calculated in step S32d (refer to FIG. 23) from the sample absorbance (Abs. 575) relative to 575 nm wavelength light, as shown in FIG. 24. Then a determination is made as to whether or not the estimated hemoglobin absorbance ((Abs. 575)–(Abs. 575 chyle estimation value)) relative to the 575 nm wavelength light is greater than a predetermined threshold value. When the ((Abs. 575)–(Abs. 575 chyle estimation value)) is determined to be greater than the predetermined threshold value in step S33a, then it is determined that hemoglobin is present in the sample in step S33b, and the hemoglobin flag is reset from OFF ([0] in the table) to ON ([1] in the table) in the sample analysis table (refer to FIG. 20). In contrast, when the ((Abs. 575)–(Abs. 575 chyle estimation value)) is determined to be less than the predetermined threshold value in step S33a, it is determined that the sample hemoglobin content will not influence the main measurement, and the hemoglobin flag remains OFF (set at [0] in the table) in the sample analysis table.

In step S33c, a hemoglobin absorbance estimation value (Abs. 405 Hgb estimation value) is calculated relative to light at 405 nm wavelength from the (Abs. 575)–(Abs. 575 chyle estimation value) calculated in step S33a. Specifically, as shown in equation (4) below, the (Abs. 405 Hgb estimation value) is calculated by multiplying (Abs. 575)–(Abs. 575 chyle estimation value calculated in step S33a by the constant multiplier H (6.5~7.5 (preferably 6.8)).

(Abs. 405 Hgb estimation value)=$H \times$ {(Abs. 575)– (Abs. 575 chyle estimation value)}     (4)

Figure 25:
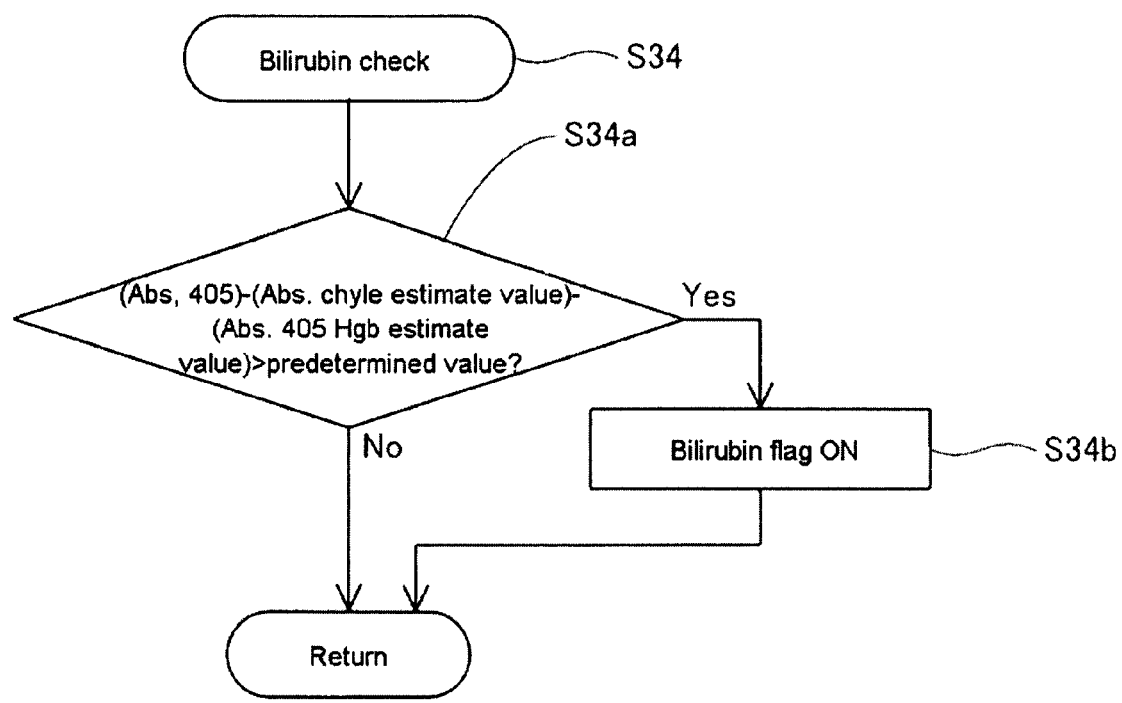
FIG. 25 is a flow chart showing the interference substance (bilirubin) check subroutine in FIG. 22.

A bilirubin check is performed in step S34 shown in FIG. 22. Specifically, in step S34a, the sample absorbance (Abs. 405 nm) relative to 405 nm light is corrected to estimate the bilirubin absorbance relative to light at a wavelength of 405 nm by subtracting the chyle absorbance estimation value (Abs. 405 chyle absorbance estimation value) relative to 405 nm wavelength light calculated in step S32e (refer to FIG. 23), and hemoglobin absorbance estimation value (Abs. 405 Hgb estimation value) relative to 405 nm wavelength light calculated in step S33c (refer to FIG. 24) from the sample absorbance (Abs. 405) relative to 405 nm wavelength light, as shown in FIG. 25. Then a determination is made as to whether or not the estimated bilirubin absorbance ((Abs. 405)–(Abs. 405 chyle estimation value)–(Abs 405 Hgb estimation value)) relative to the 405 nm wavelength light is greater than a predetermined threshold value. When the ((Abs. 405)–(Abs. 405 chyle estimation value)–(Abs. 405 Hgb estimation value)) is determined to be greater than the predetermined threshold value in step S34a, then it is determined that bilirubin is present in the sample to adversely influence the main measurement in step S34b, and the bilirubin flag is reset from OFF ([0] in the table) to ON ([1] in the table) in the sample analysis table (refer to FIG. 20). In contrast, ((Abs. 405)–(Abs. 405 chyle estimation value)–(Abs. 405 Hgb estimation value)) is determined to be less than the predetermined threshold value in step S34a, it is determined that the sample bilirubin content will not influence the main measurement, and the bilirubin flag remains OFF (set at [0] in the table) in the sample analysis table. Thus, the process of analyzing the optical information obtained by the first optical information obtaining part 40 is completed.

In the present embodiment, the chyle absorbance (Abs. 660 and Abs. 800) can be obtained at two wavelengths (600 nm and 800 nm) which are absorbed by chyle alone by calculating the sample absorbance at wavelengths of light that include 660 nm and 800 nm (405 nm, 575 nm, 660 nm, and 800 nm) that are absorbed by chyle and essentially are not absorbed by hemoglobin in step S31 as described above. Thus, a correction equation (30 can be obtained to estimate the influence by chyle on the absorbance at a predetermined wavelength based on the chyle absorbance (Abs. 660 and Abs. 800) at two wavelengths (660 nm and 800 nm) in step S32c. Therefore, the chyle absorbance estimation value (Abs. chyle estimation value) can be calculated at the 575 nm wavelength based on the correction equation (3). That is, an accurate chyle absorbance at 575 nm can be estimated compared to when chyle absorbance is estimated at a predetermined wavelength (575 nm) using a correction equation determined from a single wavelength. As a result, an accurate hemoglobin content can be estimated in step S33a. This can be suspended when the it has been determined that the hemoglobin content in the sample will adversely influence the main measurement since the main measurement will be impaired by this measurement item. Accordingly, wasteful consumption of the reagent used in the main measurement can be avoided. In this case, since a sample that has a large hemoglobin content is considered to be a sample in which the red blood cells hemolyzed during refinement of the plasma from whole blood, another blood sample can be collected and remeasured.

In the present embodiment, a correction equation (3) can be obtain for estimating the influence by chyle on absorbance at a specific wavelength in step S32c by calculating the sample absorbance at each wavelength (405 nm, 575 nm, 660 nm, 800 nm) including the 405 nm wavelength which is absorbed by bilirubin in step S31. Therefore, the chyle absorbance estimation value (Abs. 405 chyle estimation value) can be calculated at the 405 nm wavelength based on the correction equation (3). That is, an accurate chyle absorbance at 405 nm can be estimated compared to when chyle absorbance is estimated at a predetermined wavelength (405 nm) using a correction equation determined from a single wavelength. This can be suspended when the it has been determined that the chyle content in the sample will adversely influence the main measurement since the main measurement will be impaired by this measurement item. Accordingly, wasteful consumption of the reagent used in the main measurement can be avoided. Moreover, the chyle contained in the sample can be filtered, then the sample can be remeasured.

In the present embodiment, in step S34a accurate absorbance can be obtained at the 405 nm wavelength from which accurate estimations of the influence by chyle (Abs. 405 chyle estimation value) and the influence by hemoglobin (Abs. 405 Hgb estimation value have been eliminated by subtracting the chyle absorbance estimation value (Abs. 405 chyle estimation value) at the 405 nm wavelength calculated in step S32e and the hemoglobin absorbance estimation value (Abs. 405 Hgb estimation value) at the 405 nm wavelength calculated in step S33c from the sample absorbance (Abs. 405) at the 405 nm wavelength. As a result, the bilirubin content can be accurately estimated in step S34a. This can be suspended when the it has been determined that the bilirubin content in the sample will adversely influence the main measurement since the main measurement will be impaired for this measurement item. Accordingly, wasteful consumption of the reagent used in the main measurement can be avoided. Furthermore, this sample can be remeasured by another analyzer.

The present embodiment has been described by way of the example of selecting and analyzing a second optical information determined to the suitable for analysis from ten kinds of obtained second optical information based on the analysis by the first optical information obtaining part (interference substance check) and obtaining all ten kinds of optical information (digital signal data) from a second optical information obtaining part that includes a lamp unit that emits light having five different wavelengths, and amplifiers for amplifying electric signals by two different amplification factors. However, the present embodiment is not limited to this example inasmuch as the second optical information may be obtained under a selected condition by selecting one among ten kinds of measurement conditions (obtaining conditions) based on the analysis by the first optical information obtaining part.

Second Embodiment

A second embodiment of the sample analyzer is described below. The structure of the sample analyzer of the second embodiment is identical to the structure of the sample analyzer of the first embodiment. Therefore, like parts are designated by like reference numbers, and further description is omitted.

In the second embodiment the second optical information obtaining part 80 is provided to heat a measurement sample prepared by adding a coagulation time measuring reagent to a blood sample, and obtain optical information at various wavelengths over time by receiving light from the measurement sample that has been irradiated by light at a plurality of wavelengths emitted from a lamp unit 50. Specifically, the second optical information obtaining part 80 obtains transmission light over time using three types of light (405 nm, 660 nm, 800 nm) from among five types of light (340 nm, 405 nm, 575 nm, 660 nm, 800 nm) emitted from the lamp unit 50. The 660 nm wavelength light emitted from the beam splitter optical fiber 57 is the main wavelength used when measuring Fbg (fibrinogen content), PT (prothrombin time), and APTT (active partial thromboplastin time). The 800 nm wavelength light is the sub wavelength used to measure Fbg, PT, and APTT. The wavelength used to measure ATIII using the synthetic substrate method is 405 nm, and the wavelength used to measure FDP and D dimer using the immunoturbidity method is 800 nm. Platelet coagulation is measured at 575 nm. Thus, the sample analyzer 1 of the present embodiment obtains light of a plurality of wavelengths that has been emitted from one light source, the halogen lamp 51, and has passed through the optical filters 53b through 53f, and measures various measurement items using this light.

In the second optical information obtaining part 80 of the first embodiment, the main wavelength was set so as to be smaller than the sub wavelength using the fact that coagulation time can be notably captured best using low wavelength light rather than high wavelength light. Specifically, 660 nm was set as the main wavelength so as to be lower than the 800 nm was set as the sub wavelength for measuring Fbg (fibrinogen content), PT (prothrombin time), and APTT (active partial thromboplastin time).

Figure 26:
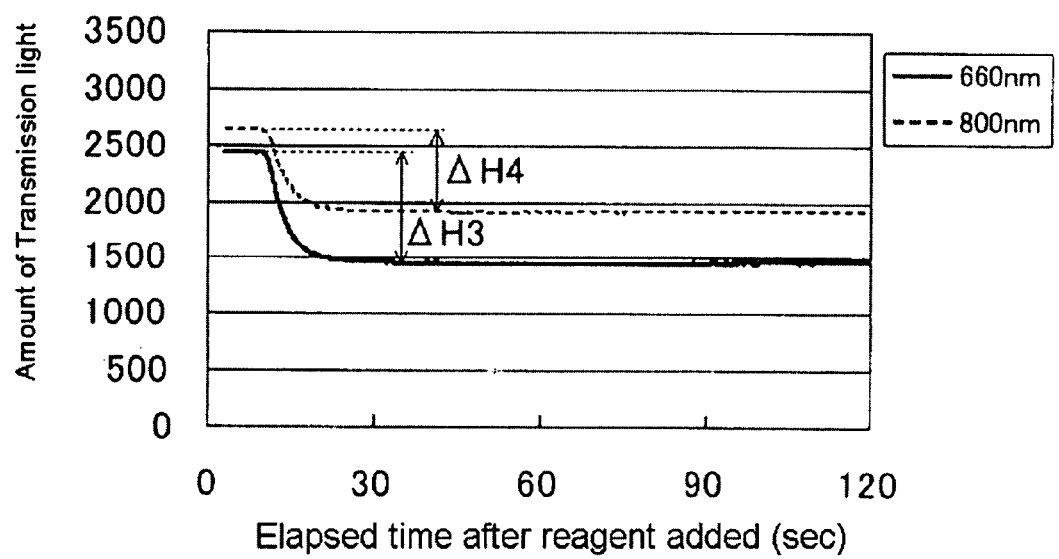
FIG. 26 shows measurement results of a blood sample containing interference substances measured by the second optical information obtaining part of a second embodiment of the sample analyzer.

In the second embodiment, the control device 4 functions to measure the presence and concentration of interference substances (chyle, hemoglobin, bilirubin) in a blood sample using transmission light detected in a period before the measurement sample indicates a coagulation reaction (shaded area (hatched area) in FIG. 26) from among light transmission light data (digital signal data) over time of the measurement sample transmitted from the second optical information obtaining part 80. Specifically, the control device 4 selects transmission light data (digital signal data) measured between 3.0 and 4.0 seconds after the addition of a coagulation time measuring reagent from among the received time course transmission light (digital signal data), and calculates an average value of a plurality of selected transmission light amounts. Therefore, in the present embodiment, the filter part 53 (refer to FIG. 8) of the lamp unit 50 is configured so as to complete one rotation per 0.1 seconds, and the application program 404a calculates the average value of ten transmission light amounts obtained between 3.0 and 4.0 seconds.

In the second embodiment, the control device 4 functions to measure the presence and concentration of interference substances (chyle, hemoglobin, bilirubin) in a blood sample using time course transmission light data (digital signal data) of a blood sample received from the first optical information obtaining part 40.

Figure 27:
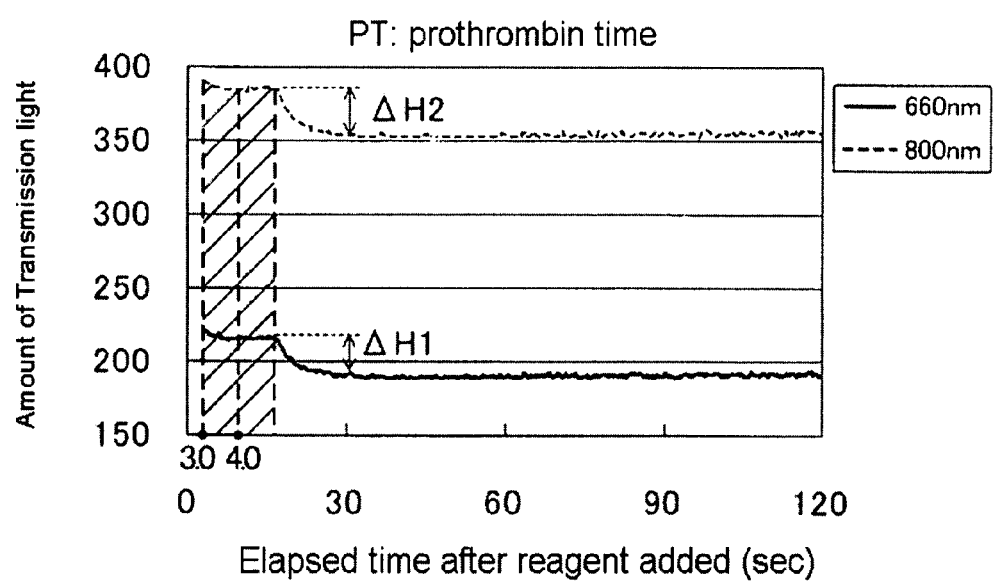
FIG. 27 shows measurement results of a normal blood sample measured by the second optical information obtaining part of the sample analyzer of the second embodiment.

The coagulation reaction (coagulation time) of a measurement sample prepared by adding coagulation time measuring reagent to a blood sample is described in detail below with reference to FIGS. 26 and 27.

When the sample analyzer 1 has measured a blood sample that contains interference substance (chyle), the measurement result measured at the main wavelength (660 nm) on the low wavelength side is less affected by the interference substance (chyle), and the amount of transmission light is approximately 190 to 220. When the main wavelength is used, the interference substance (chyle) affects and tends to reduce the amount of change $\Delta H1$ (the difference between the amount of transmission light before the reaction and the amount of transmission light after the reaction) of the transmission light indicating a blood coagulation reaction. In contrast, the measurement results measured at the sub wavelength (800 nm) on the high wavelength side are unlikely to be affected by the interference substance (chyle) as described later, and the amount of transmission light measured at the main wavelength (approximately 190 to 220) increases to approximately 350 to 390. When the sub wavelength is used, the interference substance is unlikely to affect the amount of change $\Delta H2$ ($>\Delta H1$) of the transmission light indicating a blood coagulation reaction, and there is little change. Therefore, when measuring a blood sample containing interference substance (chyle), measurement at the main wavelength on the low wavelength side captures the largest coagulation reaction.

When a normal blood sample that does not contain interference substance is measured, however, the amount of change $\Delta H3$ (=approximately 980 (=amount of transmission light before reaction (about 2440)–the amount of transmission light after the reaction (about 1460)) in the transmission light measured at the main wavelength (660 nm) on the low wavelength side is greater than the amount of change $\Delta H4$ (=approximately 720 (=amount of transmission light before the reaction (about 2630)–the amount of transmission light after the reaction (about 1910)) in the transmission light measured at the sub wavelength on the high wavelength side. Therefore, when measuring a normal blood sample, measurement at the lower main wavelength captures a larger coagulation reaction than does measurement at the higher sub wavelength.

As previously mentioned, since the wavelength of greatest absorption is different for each interference substance (chyle, hemoglobin, bilirubin), it is possible to select the wavelength to use for analysis and decide to terminate the main measurement in accordance with the type of interference substance in the blood sample and the results of qualitative determinations which are described later. Furthermore, whether or not there is an interference substance influence can be qualitatively determined for each measurement wavelength without making a qualitative determination for each interference substance. In this case, wavelengths at which it is determined there is essentially no interference substance influence is used in the analysis, wavelengths at which it is determined there is an interference substance influence are not used in analysis.

When the blood sample (plasma) being measured by the sample analyzer of the present embodiment contains interference substances (chyle, hemoglobin, and bilirubin), light absorbed by the blood sample measured using a wavelength of 405 nm is conducive to chyle absorbance, hemoglobin absorbance, and bilirubin absorbance. Furthermore, absorbance by a blood sample measured using light at a wavelength of 575 nm is conducive to chyle absorbance, and hemoglobin absorbance, and not conducive to bilirubin absorbance. Absorbance by a blood sample measured using light at wavelengths of 660 nm and 800 nm are conducive only to chyle absorbance and not conducive to hemoglobin absorbance and bilirubin absorbance. Therefore, it is possible to determine the extent, if any, of the influence the chyle content in a blood sample has on a measurement by analyzing the absorbance of the blood sample measured using light at a wavelength of 660 nm and/or 800 nm. Moreover, it is possible to determine the extent, if any, of the influence the hemoglobin content in a blood sample has on a measurement by eliminating the chyle influence (absorbance) from the absorbance of the blood sample measured using light at a wavelength of 575 nm. Thus, it is possible to determine the extent, if any, of the influence the bilirubin content in a sample has on a measurement by eliminating the chyle influence (absorbance) and hemoglobin influence (absorbance) of the sample from the absorbance of the sample measured using light at a wavelength of 405 nm.

Figure 28:
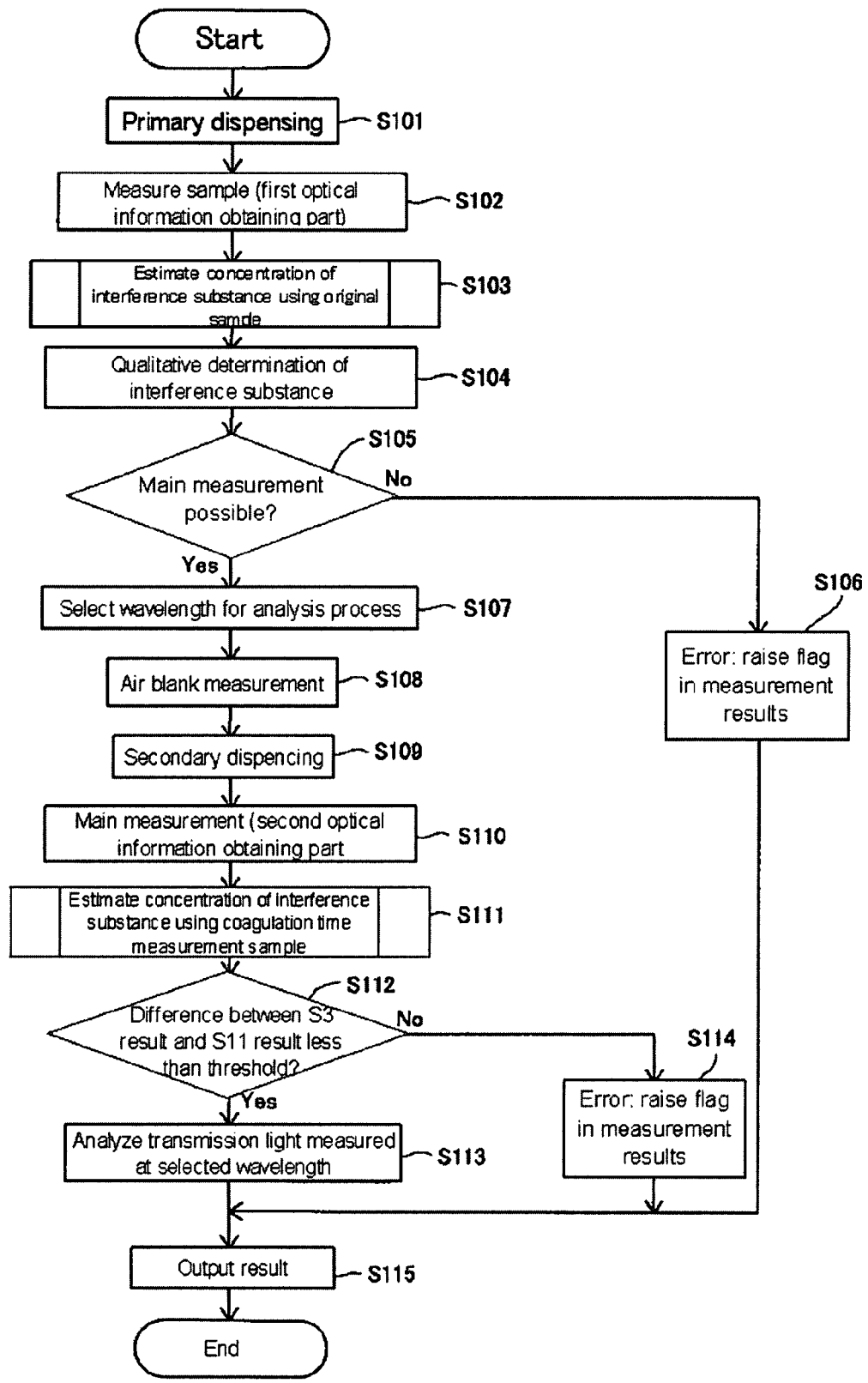
FIG. 28 is a flow chart showing the analysis sequence of the sample analyzer of the second embodiment.

FIG. 28 is a flow chart showing the sequence of the sample analysis operation performed by the sample analyzer of the second embodiment shown in FIG. 1. The blood sample measuring operation performed by the sample analyzer 1 is described in detail below.

First, a user starts the sample analyzer 1 by turning ON the power sources of the detection device 2 and control device 4 of the sample analyzer 1 shown in FIGS. 1 and 2, thus initializing the settings of the sample analyzer 1. During initialization, the detection device 2 is initialized and the registers of the controller 4a of the control device 4 are initialized by operations that return the devices for transporting the cuvettes 152 and each dispensing arm to their starting positions. Then, a user inputs sample analysis information. That is, a user uses the keyboard 4c of the control device 4 to enter the sample number and information in the columns of the measurement items in the sample analysis table (refer to FIG. 20) output to the display 4b of the control device 4. The controller 4a receives the input sample analysis information, and the input sample analysis information is saved in the controller 4a.

The sample analysis information can not only be entered using the keyboard 4c, the user also can adhere a barcode label beforehand to the test tube 150 containing the sample such that the controller 4a may acquire the sample analysis information by reading the barcode using a barcode reader or the like. In this case, to read the data on the barcode label, the controller 4a accesses a host computer for managing sample analysis information and the like to obtain sample analysis information corresponding to the data read from the barcode label. Thus, the controller 4a may obtain the sample analysis information without the user inputting the information.

The user inputs an analysis process start command after the sample number and measurement items have been input, and with the reagent container (not shown in the drawing) containing the reagent necessary for the preparation of the measurement sample, and the test tubes 150 containing the samples disposed at predetermined positions. Then, data representing a command to start the measurement are sent to the detection device 2 by the user inputting the command to start the analysis process, and the rack 151 accommodating the test tubes 150 containing the samples is transported by the transport mechanism 4 shown in FIG. 2. Thus, the rack 151 is transported from the rack set region 3a to a position corresponding to the aspirating position 2a of the detection device 2. In step S101, a predetermined amount of the blood sample is aspirated from the test tube 150 via the sample dispensing arm 30 (refer to FIG. 2). The sample dispensing arm 30 is then moved above the cuvette 152 held on the primary dispensing table 24 of the rotating part 20. Thereafter, the blood sample is allocated into the cuvettes 152 by discharging the blood sample from the sample dispensing arm 30 into the cuvettes 152 on the primary dispensing table 24.

Then the primary dispensing table 24 is rotated, and the cuvette containing the dispensed blood sample is transported to a position at which the first optical information obtaining part 40 can perform the measurement. Thus, in step S102, a plurality (five kinds) of transmission light are obtained from the blood sample by optically measuring under a plurality of conditions the blood sample (undiluted sample before the addition of blood coagulation time measuring reagent and the like) within the cuvette 152 via the first optical information obtaining part 40. Specifically, light of five different wavelengths (340 nm, 405 nm, 575 nm, 660 nm, 800 nm) are emitted from the beam splitter optical fiber 58 of the lamp unit 50 to the cuvette 152 in the holder 24a (refer to FIG. 4) of the primary dispensing table 24. The transmission light emitted from the beam splitter optical fiber 58, which has passed through the cuvette 152 and the blood sample within the cuvette 152, is sequentially detected by the photoelectric conversion element 42. The electrical signals of the transmission light detected by the photoelectric conversion element 42 are amplified by the preamp 45a (refer to FIG. 5) and the amplifier 45e, and converted to digital signals by the A/D converter 45c. Thereafter, the controller 45d sends the digital signals that correspond to the transmission light to the controller 4a of the control device 4. Thus, the acquisition of the transmission light (digital signal data) of a blood sample by the first optical information obtaining part 40 is completed. Then, the absorbance at each wavelength is calculated from the received transmission light data by the controller 4a of the control device 4.

In step S103, the CPU 401a of the control device 4 (refer to FIG. 12) estimates the presence and concentration of interference substances (chyle, hemoglobin, bilirubin) in the blood sample (original sample) using the transmission light data (digital signal data) received from the first optical information obtaining part 40, and thereafter executes qualitative determinations regarding the interference substances in step S104. The qualitative determination whether each interference substance is a strong positive (content is high in the sample), weak positive (predetermined amount in the sample), or negative (essentially none in the sample). The processes of steps S103 and S104 are described in detail below. The CPU 104a calculates the absorbance of the blood sample, and calculates the presence and concentration of the interference substances (chyle, hemoglobin, bilirubin) in the blood sample using the received digital signal data. Specifically, the CPU 401a calculates the absorbance of the blood sample and calculates the presence and concentration of interference substances (chyle, hemoglobin, bilirubin) using the transmission light data obtained using the four kinds of light (405 nm, 575, nm, 660 nm, 800 nm) emitted from the lamp unit 50. Then the CPU 401a qualitatively determines the interference substances based on the calculated presence and concentrations of the interference substances in the blood sample. The qualitative determination include evaluations of negative [−] indicating there is essentially no interference substance in the sample, weak positive [+] indicating a predetermined amount of interference substance is present in the sample, and strong positive [++] indicating a high interference substance content in the sample. In step S115 described later, the result of the qualitative determination is displayed on the display 4b of the control device 4 together with the analysis results, such as coagulation time, obtained in step S113.

In step S105, the CPU 401a determines whether or not a main measurement is possible based on the qualitative determination result of step S104. The process of step S105 is described in detail below. As shown in FIGS. 13 through 15, the wavelengths affects by each interference substance are different. That is, hemoglobin absorbs light at wavelengths of 405 nm and 575 nm, and essentially does not absorb light at wavelengths of 660 nm and 800 nm. Therefore, it is understood that hemoglobin essentially exerts no influence on analysis using light of 660 nm and 800 nm wavelengths, and does affect analysis using light of 405 nm and 575 nm wavelengths. Similarly, bilirubin essentially exerts no influence on analysis using light of 575 nm, 660 nm, and 800 nm wavelengths, and does affect analysis using light of 405 nm wavelength. Chyle affects analysis at all wavelengths (405 nm, 575 nm, 660 nm, 800 nm). Thus, when the sample has a high hemoglobin content (strong positive) in the results of the qualitative determination of interference substances, blood coagulation time can not be analyzed normally using measurement items of the 405 nm and 575 nm wavelengths. When the sample has a high hemoglobin content (strong positive), blood coagulation time can not be analyzed normally using measurement items of the 405 nm wavelength. When the sample has a high chyle content (strong positive), blood coagulation time can not be analyzed normally since all wavelengths are strongly affects. Therefore, it is determined that the main measurement can not be performed when hemoglobin is strongly positive in the qualitative determination results and the measurement wavelength is 405 nm or 575 nm, when bilirubin is strongly positive and the measurement wavelength is 405 nm, and when chyle is strongly positive. When it has been determined that the main measurement can not be performed in step S105, a measurement error is produced and a flag is raised in the measurement results in step S1106. Subsequently, in step S115 described later, the message "measurement error" is displayed with an error code on the display 4b of the control device 4. Thus, the user is made aware of the content of the error by referring to the error code displayed on the display 4b, and the error code recorded in an operating manual or the like.

When it is determined that the main measurement can be performed in step S105, then the CPU 401a selects a wavelength to be used for analysis in step S107. As mentioned above, the main wavelength (660 nm) is selected when chyle is negative in the qualitative determination result, and the sub wavelength (800 nm) is selected when chyle is a weak positive. The wavelength change flag remains OFF when the main wavelength is selected, and the wavelength change flag is set to ON when the sub wavelength is selected.

In step S108, light emitted from the beam splitter optical fiber 57 is received by the photoelectric conversion element 82b (refer to FIG. 9) opposite the pertinent insertion hole 81a in which the cuvette 152 containing the measurement sample is inserted. Thus, it is possible to detect, as electrical signals, the light characteristics such as the inherent fluctuation and the like of the beam splitter optical fiber 57 corresponding to the expected insertion hole 81a accommodating the predetermined cuvette 152. As a result, the signals corresponding to the transmission light of the measurement sample can be corrected by subtracting the electrical signals detected at the insertion hole 81a that does not accommodate a cuvette 152 from the electrical signals obtained from the measurement sample within the cuvette 152 inserted in the insertion hole 81a. In this way it is possible to suppress micro differences in the obtained electrical signals due to the position at which the cuvette 152 is inserted. In the present embodiment, the inherent electrical signals of the beam splitter optical fiber 57 are detected during the three second after the addition of the coagulation time measuring reagent from the dispensing arm 60 into the blood sample until the cuvette 152 is inserted.

In step S109, a predetermined amount of the blood sample is aspirated from the cuvette 152 in the holder 24a of the first dispensing table 24 via the sample dispensing arm 30. Next, the secondary dispensing process is performed by discharging a predetermined amount of the blood sample from the sample dispensing arm 30 into a plurality of cuvettes 152. Then, the reagent dispensing arm 60 is actuated and coagulation time measuring reagent for coagulating the blood, which is accommodated in a reagent container (not shown in the drawing) loaded on the reagent tables 21 and 22, is added to the blood sample in the cuvettes 152 of the secondary dispensing table 23. Thus, measuring samples are prepared. In step S110, the cuvettes 152 containing the measurement samples on the secondary dispensing table 23 are moved to the insertion hole 81a of the cuvette loader 81 of the second optical information obtaining part 80. After the cuvette 152 containing the measurement sample has been inserted in the insertion hole 81a of the cuvette loaded 81, a plurality (ten kinds) of transmission light are obtained from the measurement sample by the detection unit 82 of the second optical information obtaining part 80 optically measuring (main measurement) the measurement sample in the cuvette 152 under a plurality of conditions. Specifically, the cuvette 152 inserted in the insertion hole 81a of the cuvette loader 81 is first heated to a predetermined temperature by a heating device (not shown in the drawing). Thereafter, light is emitted from the beam splitter optical fiber 57 of the lamp unit 50 and irradiates the cuvette 152 on the cuvette loader 81, as shown in FIG. 10. Light of five different wavelengths (340 nm, 405 nm, 575 nm, 660 nm, 800 nm) emitted from the beam splitter optical fiber 57 periodically illuminates via the rotation of the filter part 53 (refer to FIG. 8). The light of each wavelength emitted from the beam splitter optical fiber 57 that has passed through the cuvette 152 and the measurement sample within the cuvette 152 is sequentially detected by the photoelectric conversion element 82b. Then, the electric signals, which represent the amount of transmission light corresponding to the light of five different wavelengths that have been converted by the photoelectric conversion element 82b, are amplified by the preamp 82c and sequentially input to the amplifier 82g.

In the amplifier part 82g, the electric signals, which represent the amount of transmission light corresponding to the light of five different wavelengths output from the preamp 82c (refer to FIG. 11), are input to the high amplification factor amp (H) 82l and normal amplification factor amp (L) 82k. The controller 82j controls the switch 82m such that the electric signals that have been amplified by the amp (H) 82l are output to the A/D converter 82h, and thereafter the electric signals that have been amplified by the amp (L) 82k are output to the A/D converter 82h. The switch 82m repeatedly switches in accordance with the timing of the rotation of the filter part 53 (refer to FIG. 8) in the lamp unit 50. Thus, the electrical signals representing the transmission light corresponding to the light at five different wavelengths are respectively amplified by two different amplification factors in the amplifier part 82g, and a total of ten electric signals are repeatedly output to the A/D converter 82h. These ten electric signals are converted to digital signals by the A/D converter 82h and the digital signals are temporarily stored in the logger 82i, and subsequently these digital signals are sequentially transmitted to the controller 4a of the control device 4.

The electrical signals corresponding to the transmission light are detected by the photoelectric conversion element 82b during the period after the cuvette 152 containing the measurement sample has been inserted into the insertion hole 81a (3 seconds after the coagulation time measuring reagent was added until the coagulation reaction is completed, and sent to the controller 4a of the control device 4. Thus, the CPU 401a of the control device 4 calculates the amount of change in the transmission light for each wavelength (=amount of transmission light before the reaction less the amount of transmission light after the reaction) using the received time course transmission light data.

After the second optical information obtaining part 80 has obtained the transmission light data (main measurement), the CPU 401a estimates the presence and concentration of interference substances (chyle, hemoglobin, bilirubin) in the measurement sample in step S111 using the lag phase (4 seconds elapsing after the addition of the coagulation time measuring reagent) transmission light data. The coagulation reaction starts blood coagulation by changing the fibrinogen in the plasma to fibrin through many internal and external reaction systems. That is, blood coagulation does not soon start even though blood coagulation reagent is mixed with the plasma, rather a coagulation reaction normally occurs after approximately seven seconds in external systems (PT measurement reagent), and normally after about 14 seconds in internal systems (APTT measurement reagent). Therefore, the optical information before a coagulation reaction is indicated (referred to as "lag phase") is information before an optical change occurs due to the coagulation reaction, and can be said to be optical information that is identical to the information when the sample is in a diluted condition. Hence, the presence and concentration of interference substances can be estimated from the sample diluted with coagulation time measuring reagent.

In step S112, the CPU 401a determines whether or not the difference between the interference substance estimation results estimated by the CPU 401a in step S103 using the blood sample (original sample) and the interference substance estimation results estimated in step S111 using the measurement sample is less than a predetermined threshold value. That is, discrepancies in the two estimation results obtained from the same blood sample are monitored in step S112.

When the difference between the two estimation results is less than the predetermined threshold value in step S112, the CPU 401a analyzes blood coagulation time using the measurement sample transmission light data measured at the wavelength selected in step S107 among the main wavelength and sub wavelength from among the plurality of transmission light data measured by the second optical information obtaining part 80 in step S113. For example, in the case of measuring [PT] in the blood sample, when wavelength change flag is OFF, [PT] is measured using the light of the main wavelength 660 nm. Thereafter, the CPU 401a outputs the blood coagulation time and analysis results including various flags in step S115.

When the CPU 401a of the control device 4 determines that the difference in the two estimation results exceeds the threshold value in step S112, a measurement error is determined and a flag is raised in the measurement results in step S114. Thereafter, the message "measurement error" and an error code are displayed in the display 4b of the control device 4 in step S115. Thus, the user is made aware of the content of the error by referring to the error code displayed on the display 4b, and the error code recorded in an operating manual or the like. In this way the blood sample analysis operation performed by the sample analyzer 1 is completed.

Figure 29:
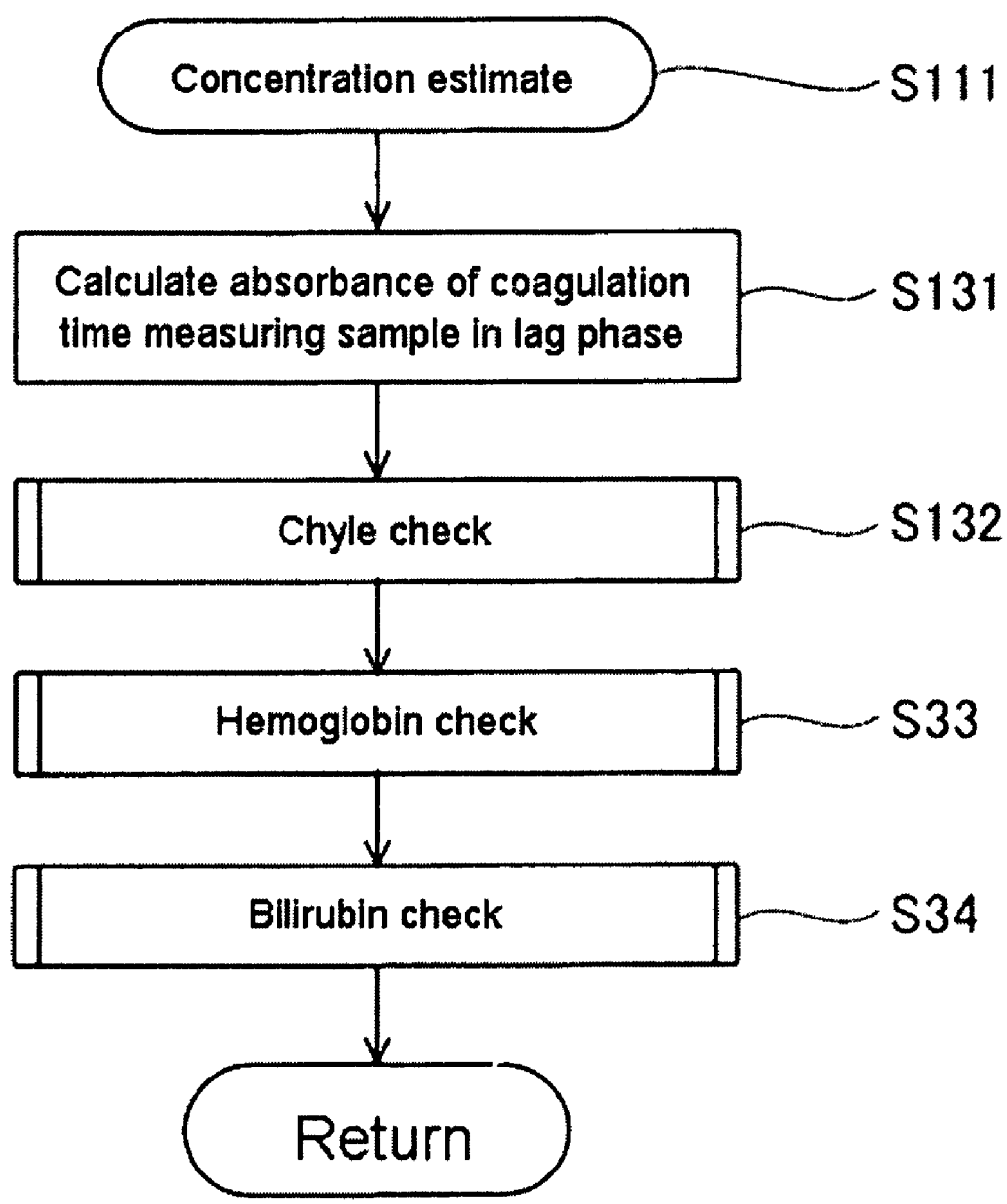
FIG. 29 is a flow chart showing details (subroutines) of the interference substance concentration estimating process performed by the control device of the sample analyzer of the second embodiment.
Figure 30:
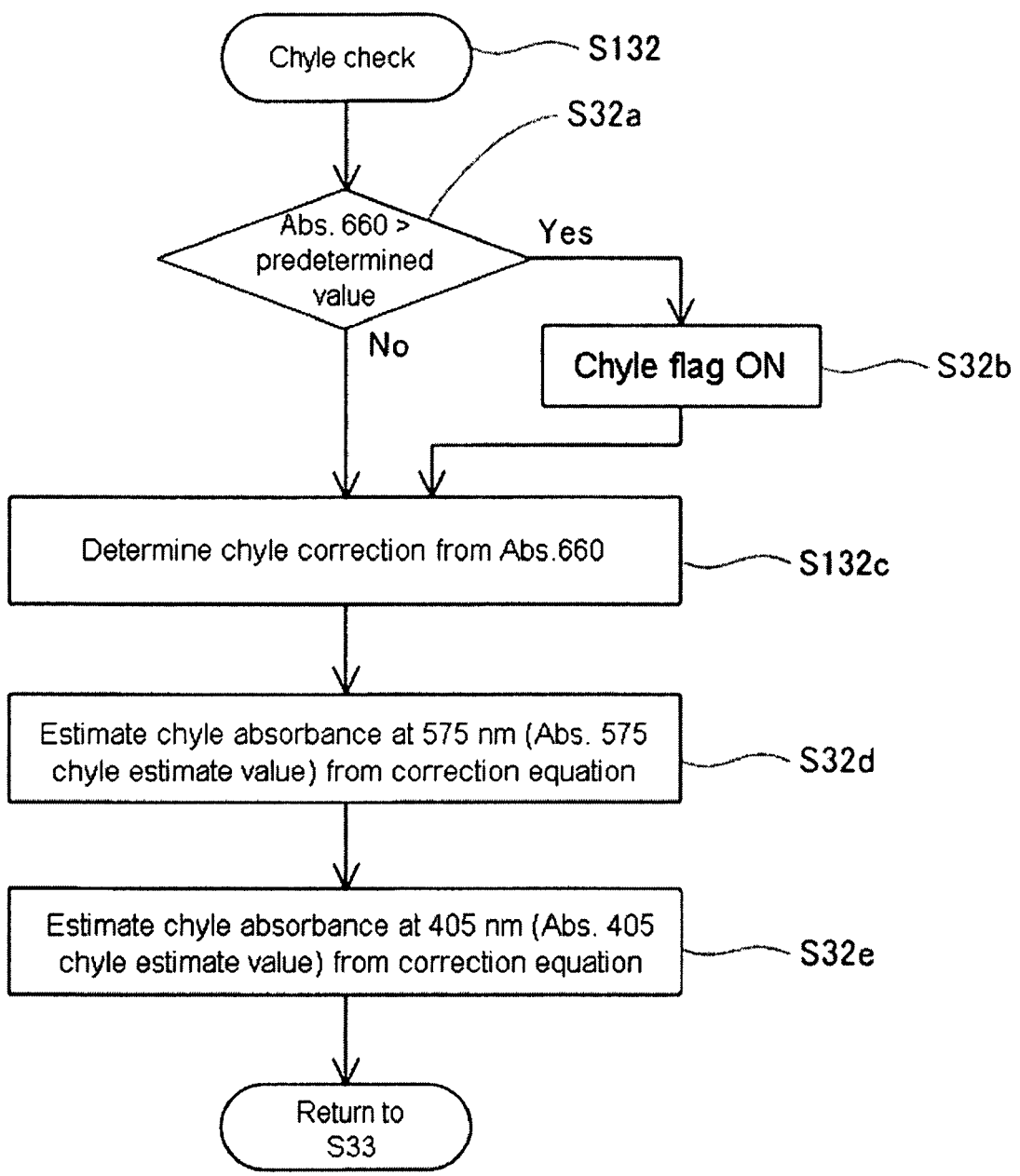
FIG. 30 is a flow chart showing the interference substance (chyle) check subroutine in FIG. 23.

FIGS. 29 and 30 are flow charts showing details (subroutines) of the interference substance concentration estimating process of step S111 of FIG. 28. The interference substance concentration estimating process of step S111 of FIG. 28 is described in detail below.

In step S131 if FIG. 29, the measurement sample absorbance during the lag phase is calculated for light of each wavelength (405 nm, 575 nm, 660 nm, 800 nm) via the measurement sample transmission light data during the lag phase obtained by the second optical information obtaining part 80. Specifically, the CPU 401a calculates the absorbance using the average value of a total of ten transmission light data during the period after the cuvette 152 containing the measurement sample has been inserted into the insertion hole 81a (3 seconds after the coagulation time measuring reagent was added) to a point before the coagulation reaction starts (4.0 seconds from the addition of the coagulation time measuring reagent). The absorbance A is a value determined by equation (5) below using the light transmittance T (%) of the measuring sample.

$$A = -\log 10(T/100) \tag{5}$$

A chyle check is performed in step S132. The chyle check process in the present embodiment is identical to the chyle check process 32 of the first embodiment except for elimination of the process for determining the chyle correction equation. As shown in FIG. 30, the chyle correction equation is determined using the measurement sample absorbance (Abs. 660) of the 660 nm wavelength light in step S132c of the second embodiment. Specifically, the following chyle absorbance standard equation (6) is determined beforehand.

$$Y = 10b0 - Xa0 \tag{6}$$

The standard equation is a relation equation between the standard chyle absorbance Y and wavelength λ. That is, a0 and b0 are determined as the unknowns a and b in equation (1) above, and the equation is changed (with Y on the left side) to become a absorbance equation. The difference between the absorbance at 660 nm of the standard equation (obtained absorbance replaces the wavelength 660 in the standard equation) and the measured absorbance (Abs. 660) {(Abs. 660)−(Abs. 660 standard)} is added to the right side of the standard equation. Thus, the following chyle correction equation (7) is obtained.

$$Y = 10b0 - Xa0 + \{(\text{Abs. }660) - (\text{Abs. }660\text{ standard})\} \tag{7}$$

Processes other than the chyle check process of step S132 in the second embodiment are identical to the chyle check process of step S32 of the first embodiment, and further description is omitted.

Next, the hemoglobin check is performed in step S33, and the bilirubin check is performed in step S34. The hemoglobin check process and bilirubin check process in the second embodiment are identical to the hemoglobin check process of step S33 and the bilirubin check process of step S34 of the first embodiment and, therefore, further description is omitted. Thus, the interference substance concentration estimate using the measurement sample is completed.

The interference substance concentration estimate using the blood sample (original sample) in step S103 of FIG. 28 is identical to the interference substance concentration estimate using the measurement sample described above with the exception that the data used are the transmission light data obtained by the first optical information obtaining part 40 and, therefore, further description is omitted.

Third Embodiment

The structure of the sample analyzer of the third embodiment is not provided with the first optical information obtaining part 40 of the sample analyzers of the first and second embodiments. Accordingly, the interference substance concentration estimate and qualitative determination of interference substances are not based on obtaining optical information by the first optical information obtaining part 40 in priority to obtaining optical information obtained by the second optical information part 80, and the interference substance concentration estimate and qualitative determination of interference substances are based only on optical information of the lag phase obtained by the second optical information obtaining part 80. Like parts in common with the sample analyzer of the second embodiment are identified by like reference numbers, and further description is omitted.

Figure 31:
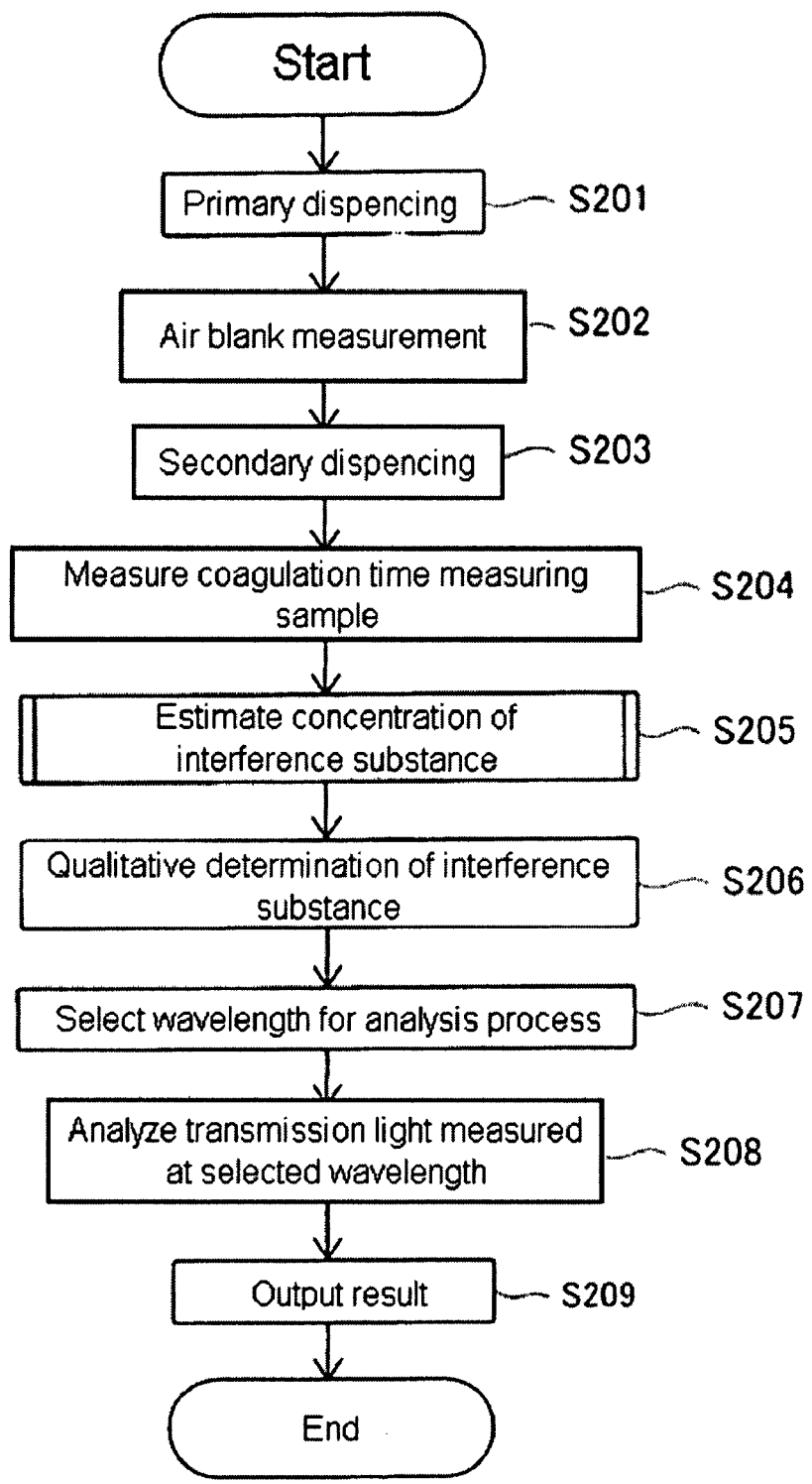
FIG. 31 is a flow chart showing the analysis sequence of the sample analyzer of a third embodiment.

FIG. 31 is a flow chart showing the sample analysis sequence of the sample analyzer of a third embodiment. First, a user starts the sample analyzer 1 by turning ON the power sources of the detection device 2 and control device 4 of the sample analyzer 1 shown in FIGS. 1 and 2, thus initializing the settings of the sample analyzer 1. Subsequently, the user inputs sample analysis information and an analysis process start command. After the command has been input to start the analysis process, the blood sample is allocate in step S201 shown in FIG. 31. The initialization of the sample analyzer 1, sample analysis information input, and primary dispensing process of step S201 are identical to the process of step S101 (refer to FIG. 32) of the second embodiment and, therefore, further description is omitted.

After the primary dispensing process of step S201, the a measurement process is performed on an air blank in step S202, and subsequently the secondary dispensing process is performed in step S203. In step S204, the measurement sample is optically measured under a plurality of conditions, and transmission light data are obtained by the second optical information obtaining part 80. The processes of steps S202, S203, and S204 are identical to the processes in steps S108, S109, and S110 of the second embodiment and, therefore, further description is omitted.

In step S205, the CPU 401a estimates the presence and concentration of interference substances (chyle, hemoglobin, bilirubin) in the measurement sample using the transmission light data of the lag phase (4.0 seconds elapsing after the blood coagulation time measuring reagent is added). Then the CPU 401a makes qualitative determinations of the interference substances based on the estimated concentrations of the interference substances in step S206. Subsequently, in step S207, the CPU 401a selects the wavelength to be used for analysis. In step S208, the CPU 401a analyzes the blood coagulation time using the measurement sample transmission light data measured at the wavelength selected in step S207 among the main wavelength and the sub wavelength from among the plurality of transmission light data measured by the second optical information obtaining part 80. Thereafter, the CPU 401a outputs the blood coagulation time and analysis results including various flags in step S209, and the process ends. The processes of steps S206, S207, S208, and S209 are identical to the processes of steps S104, S107, S113, and S115 of the second embodiment and, therefore, further description is omitted.

The concentration estimate made using the measurement sample in step S205 is described below. Since the measurement sample prepared by adding coagulation time measuring reagent to a blood sample is the object of measurement, not only is the influence by the concentration of the interference substances observable in the transmission light data, the influence caused by the turbidity of the coagulation time measuring reagent is also included in the obtained transmission light data. Therefore, it is desirable that the process consider the turbidity of the measuring reagent in the concentration estimate using the measurement sample in contrast to the concentration estimate process of step S110 of the second embodiment. The concentration estimate using the measurement sample of the present embodiment considers the turbidity of the measuring reagent.

Figure 32:
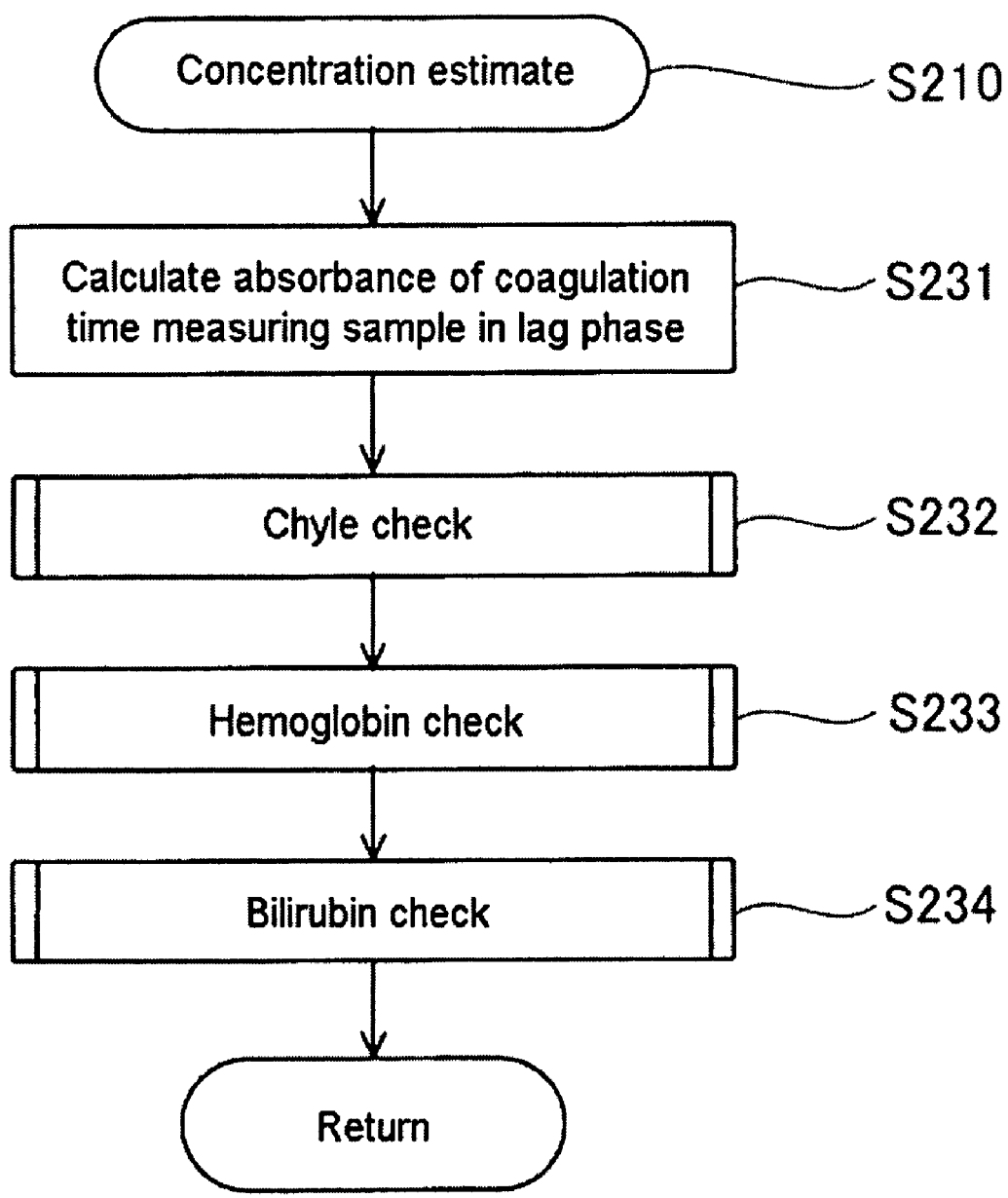
FIG. 32 is a flow chart showing details (subroutines) of the interference substance concentration estimating process performed by the control device of the sample analyzer of the third embodiment.
Figure 35:
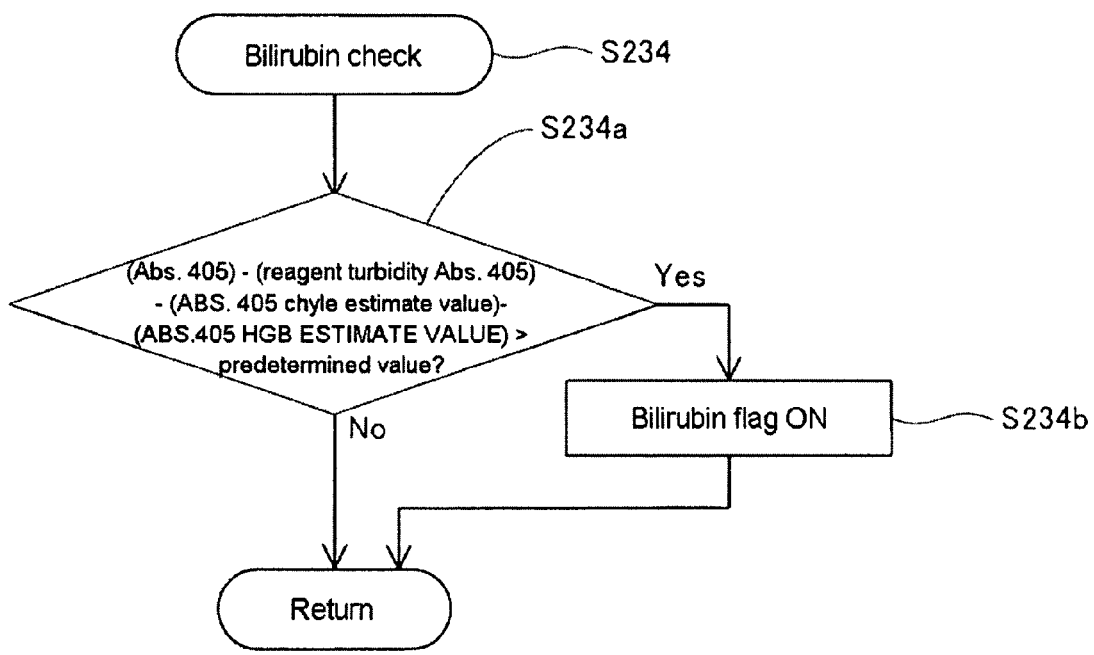
FIG. 35 is a flow chart showing the interference substance (bilirubin) check subroutine in FIG. 28.

FIGS. 32 and 35 are flow charts showing details (subroutines) of the interference substance concentration estimating process of step S205 of FIG. 31. First, the absorbance of the measurement sample relative to each wavelength (405 nm, 575 nm, 660 nm, 800 nm) is calculated in step S231 of FIG. 32. Specifically, the CPU 401a calculates the absorbance using the average value of a total of ten transmission light data obtained during the period after the cuvette 152 containing the measurement sample has been inserted into the insertion hole 81a (3 seconds after the coagulation time measuring reagent was added) to a point before the coagulation reaction starts (4.0 seconds from the addition of the coagulation time measuring reagent).

A chyle check is performed in step S232. Specifically, in step S232a the absorbance of the measurement sample at the 660 nm wavelength (Abs. 660) is corrected by subtracting the reagent induced absorbance (Abs. 660) caused by the coagulation time measuring reagent from the measurement sample absorbance (Abs. 660) relative to the 660 nm wavelength in step S232a. Thus, it is possible to obtain a corrected absorbance from which the turbidity of the coagulation time measuring reagent has been eliminated ((Abs. 660–reagent turbidity Abs. 660)). In the third embodiment, the reagent inherent turbidity at 660 nm caused by the coagulation time measuring reagent (reagent turbidity Abs. 660) as well as the absorbance at 800 nm (reagent turbidity Abs. 800), absorbance at 575 nm (reagent turbidity (Abs. 575), and absorbance at 405 nm (reagent turbidity Abs. 405) are fixed values set for each type of reagent, and determined beforehand with the coagulation time measuring reagent mixed with water. Then a determination is made as to whether or not the corrected absorbance ((Abs. 660)–(reagent turbidity Abs. 660)) is greater than a predetermined value. When it is determined that the corrected absorbance ((Abs. 660)–(reagent turbidity Abs. 660)) is greater than the predetermined value in step S232a, it is determined in step S232b that chyle is present in the measurement sample, and the chyle flag in the sample analysis table (refer to FIG. 22) is changed from OFF ([0] in the table) to ON ([1] in the table). Conversely, when it is determined that the corrected absorbance ((Abs. 660)–(reagent turbidity Abs. 660)) is less than the predetermined value in step S232a, it is determined in step S232b that the chyle content in the measurement sample will not influence the measurement, and the chyle flag in the sample analysis table (refer to FIG. 22) remains OFF ([0] in the table). Although the sample chyle content is measured using light at a wavelength of 660 nm in the present embodiment, the sample chyle content may also be measured using 800 nm light.

In the third embodiment, a corrected absorbance from which the turbidity of the coagulation time measuring reagent at 800 nm has been eliminated ((Abs. 800)–(reagent turbidity Abs. 800)) is obtained in step S232c similar to the case of light at 660 nm wavelength in step S232a. A chyle correction equation is determined using the corrected absorbance at 660 nm ((Abs. 660)–(reagent turbidity 660)) and the corrected absorbance at 800 nm ((Abs. 800)–(reagent turbidity 800)). Specifically, equation (8a) below is derived by substituting the wavelength (X=660) and corrected absorbance (Y=(Abs. 660)–(reagent turbidity Abs. 660)) in equation (1), and equation (8b) below is derived by substituting the wavelength (X=800) and corrected absorbance (Y=(Abs. 800)–(reagent turbidity Abs. 800)) in equation (1).

$$\log 10\{(\text{Abs. 660})-(\text{reagent turbidity Abs. 660})\}=a \log 10 660 + b \quad (8a)$$

$$\log 10\{(\text{Abs. 800})-(\text{reagent turbidity Abs. 800})\}=a \log 10 800 + b \quad (8b)$$

Then the constants a and b are calculated for equations (8a) and (8b) to derive the chyle correction equation (9) fro deriving the chyle absorbance y at a predetermined wavelength x.

$$\log 10 y = a \log 10 x + b \quad (9)$$

In step S232d, the chyle absorbance estimate value relative to the 575 nm wavelength (Abs. 575 chyle estimate value) is calculated from the chyle correction equation (9) determined in step S232*c*. That is, the chyle absorbance estimate value (Abs. 575 chyle estimate value) relative to the 575 nm wavelength is calculated by substituting the wavelength (x=575) in the correction equation (9).

In step S232*e*, the chyle absorbance estimate value relative to the 405 nm wavelength (Abs. 405 chyle estimate value) is calculated from the chyle correction equation (9) similar to step S232*d*. That is, the chyle absorbance estimate value relative to the 405 nm wavelength (Abs. 405 chyle estimate value) is calculated by substituting the wavelength (x=405) in the correction equation (9).

Figure 33:
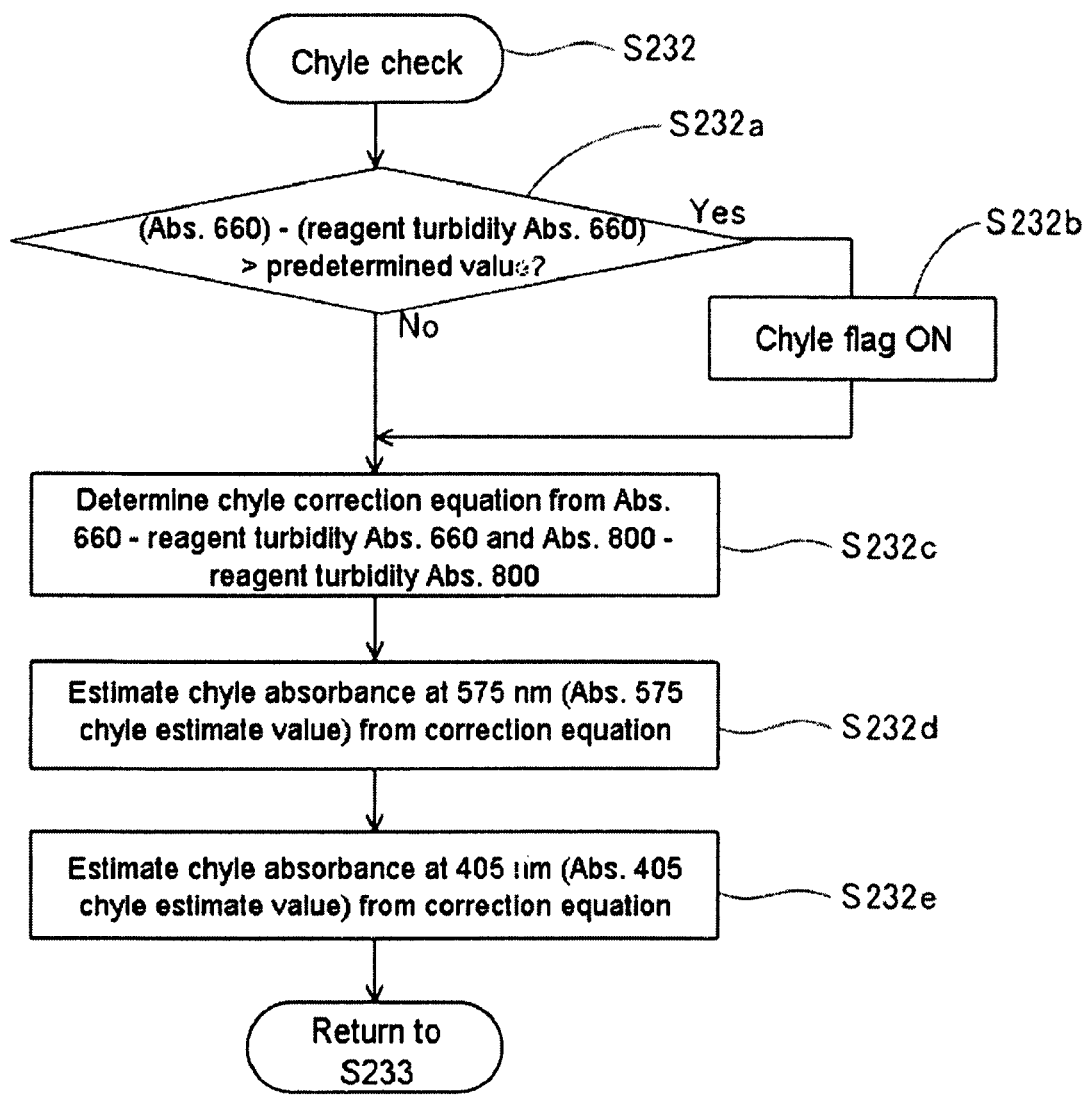
FIG. 33 is a flow chart showing the interference substance (chyle) check subroutine in FIG. 28.
Figure 34:
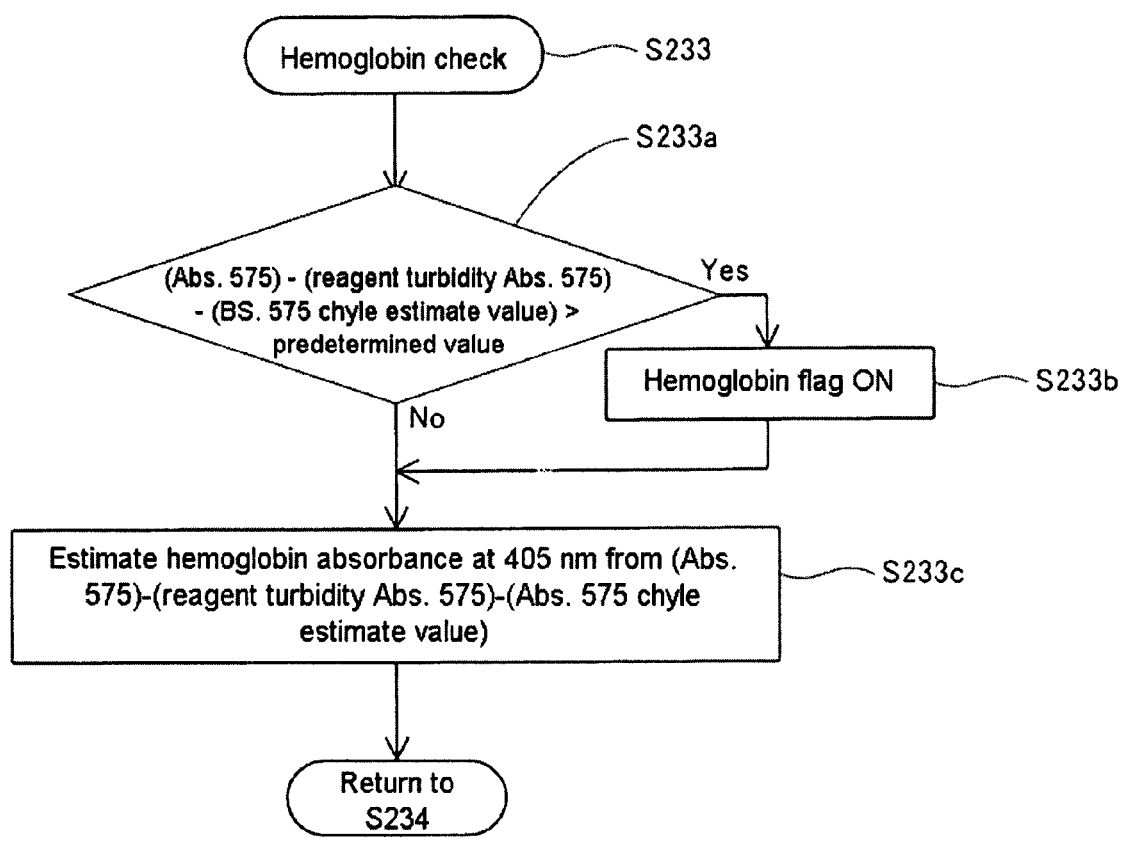
FIG. 34 is a flow chart showing the interference substance (hemoglobin) check subroutine in FIG. 28.

Next, a hemoglobin check is performed in step S233 shown in FIG. 32. Specifically, in step S233*a*, the corrected absorbance is obtained from which the turbidity of the coagulation time measuring reagent has been eliminated at the 575 nm wavelength ((Abs. 575)−(reagent turbidity Abs. 575)) similar to the 660 nm wavelength light in step S232*a*, as shown in FIG. 34. Then, the hemoglobin absorbance relative to the 575 nm wavelength light is estimated by correcting the 575 nm corrected absorbance ((Abs. 575)−(reagent turbidity Abs. 575)) by subtracting the chyle absorbance estimate value ((Abs. 575 chyle estimate value)) at the 575 nm wavelength calculated in step S232*d* (refer to FIG. 33) from the 575 nm wavelength corrected absorbance ((Abs. 575)−(reagent turbidity Abs. 575)). Then a determination is made as to whether or not the estimated hemoglobin absorbance at the 575 nm wavelength (((Abs. 575)−(reagent turbidity Abs. 575))−(Abs. 575 chyle estimate value)) is greater than a predetermined value. When it is determined that (((Abs. 575)−(reagent turbidity Abs. 575))−(Abs. 575 chyle estimate value)) is greater than the predetermined value in step S233*a*, it is determined in step S233*b* that hemoglobin is present in the measurement sample, and the hemoglobin flag in the sample analysis table (refer to FIG. 22) is changed from OFF ([0] in the table) to ON ([1] in the table). Conversely, when it is determined that (((Abs. 575)−(reagent turbidity Abs. 575))−(Abs. 575 chyle estimate value)) is less than the predetermined value in step S233*a*, it is determined in step S233*b* that the hemoglobin content in the measurement sample will not influence the measurement, and the hemoglobin flag in the sample analysis table (refer to FIG. 22) remains OFF ([0] in the table).

In step S233*c*, the hemoglobin absorbance estimate value (Abs. 405 Hgb estimate value) relative to 405 nm wavelength light is calculated from the (((Abs. 575)−(reagent turbidity Abs. 575))−(Abs. 575 chyle estimate value)) calculated in step S233*a*. Specifically, the (Abs. Hgb estimate value) is calculated by multiplying the (6.5~7.5 (preferably 6.8))−(((Abs. 575)−(reagent turbidity Abs. 575))−(Abs. 575 chyle estimate value)) calculated in step S233*a* by multiplying (((Abs. 575)−(reagent turbidity Abs. 575))−(Abs. chyle estimate value)) calculated in step S233*a* by the constant multiplier H (6.5~7.5 (preferably 6.8)).

(Abs. 405 Hgb estimate value)=$H \times \{((Abs. 575)-(reagent\ turbidity\ Abs.\ 575)-(Abs.\ 575\ chyle\ estimate\ value))\}$ (10)

Next, a bilirubin check is performed in step S234 shown in FIG. 32. Specifically, in step S234*a*, the corrected absorbance is obtained from which the turbidity of the coagulation time measuring reagent has been eliminated at the 405 nm wavelength ((Abs. 405)−(reagent turbidity Abs. 405)) similar to the 660 nm wavelength light in step S232*a*, as shown in FIG. 35. Then, the hemoglobin absorbance relative to the 405 nm wavelength light is estimated by correcting the 405 nm corrected absorbance ((Abs. 405)−(reagent turbidity Abs. 405)) by subtracting the hemoglobin absorbance estimate value ((Abs. 405 Hgb estimate value)) at the 405 nm wavelength calculated in step S233*c* (refer to FIG. 34) from the 405 nm wavelength corrected absorbance ((Abs. 405)−(reagent turbidity Abs. 405)). Then a determination is made as to whether or not the estimated hemoglobin absorbance at the 405 nm wavelength (((Abs. 405)−(reagent turbidity Abs. 405))−(Abs. 405 chyle estimate value) is greater than a predetermined value. When it is determined that (((Abs. 405)−(reagent turbidity Abs. 405))−(Abs. 405 chyle estimate value)) is greater than the predetermined value in step S234*a*, it is determined in step S234*b* that the hemoglobin content in the measurement sample will adversely affect the measurement, and the hemoglobin flag in the sample analysis table (refer to FIG. 22) is changed from OFF ([0] in the table) to ON ([1] in the table). Conversely, when it is determined that (((Abs. 405)−(reagent turbidity Abs. 405))−(Abs. 405 chyle estimate value)) is less than the predetermined value in step S234*a*, it is determined in step S234*b* that the hemoglobin content in the measurement sample will not influence the measurement, and the hemoglobin flag in the sample analysis table (refer to FIG. 22) remains OFF ([0] in the table). Thus, the concentration estimate using the measurement sample is completed.

In the second and third embodiments, a plurality of transmission light data over time for use in the coagulation time measurement (main measurement), and transmission light data before a coagulation reaction is indicated (time from the addition of the coagulation reagent to 30.0 to 4.0 seconds thereafter) for use in estimating the presence and concentration of interference substances in a measurement sample are both obtained by providing the second optical information obtaining part 80. Thus, the control device 4 not only measures the coagulation time using the change in the transmission light data over time, the control device 4 can also measure the presence and concentration of interference substances using the transmission light data before a coagulation reaction is indicated (hatched region in FIG. 13).

In the second and third embodiments, the change in a plurality of transmission light for use in measuring coagulation time (main measurement), and transmission light before a coagulation reaction is indicated for use in estimating the presence and concentration of interference substance can be obtained from a single measurement sample prepared by adding coagulation time measuring reagent to a blood sample. The coagulation reaction starts blood coagulation by changing the fibrinogen in the plasma to fibrin through many internal and external reaction systems. That is, blood coagulation does not soon start even though blood coagulation reagent is mixed with the plasma, rather a coagulation reaction normally starts after approximately seven seconds in external systems (PT measurement reagent), and normally after about 14 seconds in internal systems (APTT measurement reagent). In the present embodiment, the optical information before a coagulation reaction is indicated (referred to as "lag phase") is information that is identical to the information when the sample is in a diluted condition. According to the configuration described above, consumption of blood sample can be suppressed since a sample used for the main measurement and a sample for estimating the presence and concentration of interference substance need not be prepared separately.

In the second and third embodiments, transmission light data can be obtained from a measurement sample diluted with coagulation time measuring reagent by providing a second optical information obtaining part 80 for receiving light over time from a measurement sample prepared by adding coagulation reagent to a blood sample, and obtaining the change in transmission light over time. Thus, the measurable range from which transmission light data is obtainable can be increased since the second optical information obtaining part 80 can obtain transmission light data from a diluted measurement sample even when it is difficult to detect transmission light data due to the high concentration of the blood sample.

In the third embodiment, chyle influence on absorbance can be estimated at other wavelengths (second wavelength, third wavelength) based on absorbance at two wavelengths that are absorbed by chyle and essentially not absorbed by bilirubin and hemoglobin configuring the control device 4 so as to estimate the influence by chyle on optical information at wavelengths of 575 nm and 405 nm based on the absorbance at 660 nm and 800 nm. Thus, estimating chyle influence on absorbance at other wavelengths based on absorbance at two types of wavelengths produces an accurate estimate of chyle influence compared to estimating chyle influence on absorbance at other wavelengths based on absorbance at a single wavelength. As a result, the influence by interference substances (chyle, hemoglobin, bilirubin) can be accurately estimated since the influence by bilirubin and hemoglobin can be estimated using the accurately estimated chyle influence.

In the second embodiment, measurement can be stopped by determining that highly reliable coagulation time measurement is unlikely when there is a high concentration of interference substance in the blood sample measured by the first optical information obtaining part 40 by providing the first optical information obtaining part 40 for obtaining transmission light from a blood sample before the coagulation reagent has been added, in addition to the second optical information obtaining part 80 for performing the main measurement. As a result, consumption of the coagulation reagent can be suppressed since the addition of the coagulation reagent to the blood sample can be stopped when a measurement is terminated. In this case, the measuring efficiency of the device is improved since the main measurement is not carried out by the second optical information obtaining part 80 on a blood sample for which a highly reliable measurement result (coagulation time) is unlikely to be obtained.

In the second embodiment, concentration estimates can be made using a measurement sample in addition to the concentration estimates using the original sample (blood sample) by providing the second optical information obtaining part 80 for performing a main measurement, and a first optical information obtaining part 40 for obtaining transmission light by receiving light from a blood sample to which coagulation reagent is to be added. Thus, an accurate estimate result can be confirmed by comparing the concentration estimate obtained using the original sample (blood sample) and the concentration estimate obtained using the measurement sample. As a result, it is possible to obtain a more accurate measurement result of the presence and concentration of interference substances. Device errors caused by coagulation reagent dispensing error and the like can be monitored when there is a discrepancy between the compared estimate results.

In the third embodiment, the sample analyzer becomes less complex and more compact since a separate main measurement device (second optical information obtaining part 80) and separate dedicated device (first optical information obtaining part 40) for measuring interference substances are unnecessary when the second optical information obtaining part 80 is provided along without the first optical information obtaining part 40. Moreover, the operation of the sample analyzer becomes less complex since the optical measurement of the blood sample is unnecessary.

The above embodiments are offered as examples and should not to be considered limiting in any way. The scope of the present invention is specified by the scope of the claims and not in the description of the embodiments, and the scope of the claims includes all equivalent meanings and modifications that fall within the scope of the claims.

Although a low wavelength is set as the main wavelength and the a high wavelength is set as the sub wavelength in the second and third embodiments, the present invention is not limited to this arrangement inasmuch as a high wavelength may be set as the main wavelength and a low wavelength may be set as the sub wavelength. Thus, is a low wavelength sub wavelength is selected, a coagulation reaction can be realized in a low fibrinogen blood sample even when the fibrinogen content in the blood sample is low.

Although the detection device and control device are provided separately in the first through third embodiments, the present invention is not limited to this configuration inasmuch as the function of the control device also may be provided in the detection device.

Although optical measurement of a measurement sample (main measurement) is performed using coagulation time in the first through third embodiments, the present invention is not limited to this configuration inasmuch as optical measurement of a measurement sample also may be performed using a method other than coagulation time, such as a synthetic substrate method and immunoturbidity method.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A sample analyzer comprising:
    a first measuring part configured for measuring first optical information of a sample at first light of first wavelength, second optical information of a sample at second light of second wavelength, and third optical information of a sample at third light of third wavelength, wherein the first light of the first wavelength and the second light of the second wavelength are absorbed by a first substance but substantially not absorbed by a second substance, and the third light of the third wavelength is absorbed by the second substance;
    a preparing part configured for preparing a measurement sample by mixing a reagent with a part of the sample;
    a second measuring part configured for optically measuring the measurement sample prepared by the preparing part, wherein the first substance of an excessive content interferes with the measurement by the second measuring part and the second substance of an excessive content interferes with the measurement by the second measuring part; and
    a controller configured for executing operations comprising:
        determining whether one of content of the first substance and content of the second substance, from which the influence by the first substance is excluded, in the sample is excess or not based on the first, second, and third optical information measured by the first measuring part;
        analyzing the measurement sample based on the result of measurement by the second measuring part; and
        outputting an analysis result with a flag when one of content of the first and second substances is excess.

2. The sample analyzer according to claim 1, wherein the operations further comprise:

estimating the influence by the first substance on the third optical information based on the first and second optical information; and correcting the third optical information based on the estimated influence by the first substance on the third optical information;

wherein the determining is carried out based on the first and second optical information and the corrected third optical information.

3. The sample analyzer according to claim 2, wherein the determining is carried out by:

determining whether the content of the first substance is excess or not based on at least one of the first and second optical information; and determining whether the content of the second substance is excess or not based on the corrected third optical information; and wherein the outputting comprises:

outputting the analysis result with a first substance flag when content of the first substance is excess; and outputting the analysis result with a second substance flag when content of the second substance is excess.

4. The sample analyzer according to claim 1, wherein the first light, the second light, and the third light are substantially not absorbed by a third substance, wherein the third substance of an excessive content interferes with the measuring by the second measuring part;

wherein the first measuring part is configured so as to further measure fourth optical information of the sample at fourth light of fourth wavelength, wherein the fourth light of the fourth wavelength is absorbed by the third substance; and wherein the operations further comprise determining whether content of the third substance, from which influence by the first and second substances is excluded, is excess or not based on the first, second, third, and fourth optical information measured by the first measuring part.

5. The sample analyzer according to claim 4, wherein the operations further comprise:

estimating the influence by the first substance on the third optical information based on the first and second optical information;

correcting the third optical information based on the estimated influence by the first substance on the third optical information;

estimating the influence by the first substance on the fourth optical information based on the first and second optical information;

estimating the influence by the second substance on the fourth optical information based on the corrected third optical information; and correcting the fourth optical information at the based on the influence by the first substance at the fourth optical information and the influence by the second substance on the fourth optical information; and wherein the determining is carried out based on corrected fourth optical information.

6. The sample analyzer according to claim 5, wherein the operations further comprise:

obtaining first information relating to presence of the first substance in the sample based on at least one of first optical information and the second optical information;

obtaining second information relating to presence of the second substance in the sample based on the corrected third optical information;

obtaining third information relating to presence of the third substance in the sample based on the corrected fourth optical information; and outputting at least one of the first, second, and third information.

7. The sample analyzer according to claim 1, wherein the first measuring part comprises:

a light source that emits the first light of the first wavelength, the second light of the second wavelength, and the third light of the third wavelength; and a light receiver that receives the first light, the second light, and the third light.

8. The sample analyzer according to claim 2, wherein the estimating is carried out by estimating optical information corresponding to the first substance at the third wavelength based on the first optical information and the second optical information; and the correcting carried out by correcting the third optical information by eliminating optical information corresponding to the first substance at the third wavelength from the third optical information.

9. The sample analyzer according to claim 8, wherein the optical information is absorbance; and the estimating of the influence by the first substance on the third optical information is carried out by estimating absorbance corresponding to the first substance at the third wavelength from a relation derived from the absorbance at the first wavelength and absorbance at the second wavelength.

10. The sample analyzer according to claim 5, wherein the first estimating of the influence by the first substance on the third optical information is carried out by estimating optical information corresponding to the first substance at the third wavelength based on the first and second optical information;

the correcting of the third optical information is carried out by correcting the third optical information by eliminating optical information corresponding to the first substance at the third wavelength from the third optical information the estimating of the influence by the first substance on the fourth optical information is carried out by estimating optical information corresponding to the first substance at the fourth wavelength based on first optical information and second optical information;

the third estimating of the influence by the second substance on the fourth optical information is carried out by estimating optical information corresponding to the second substance at the fourth wavelength based on the corrected third optical information; and the correcting of the fourth optical information is carried out by correcting fourth optical information by eliminating optical information corresponding to the first substance at the fourth wavelength, and optical information corresponding to the second substance at the fourth wavelength from the fourth optical information.

11. The sample analyzer according to claim 1, wherein the first wavelength and second wavelength are equal to or greater than 590 nm and equal to or less than 900 nm.

12. The sample analyzer according to claim 1, wherein the third wavelength is equal to or greater than 500 nm and less than 590 nm.

13. The sample analyzer according to claim 4, wherein the fourth wavelength is equal to or greater than 300 nm and less than 500 nm.

14. A sample analyzer comprising:

a first light emitting part configured for emitting light to a blood sample;

a first light receiving part configured for obtaining optical information at a plurality of time points by receiving light of a plurality of wavelengths from the blood sample irradiated by the light;

a sample preparing part configured for preparing a measurement sample by mixing a reagent for measuring coagulation time with a part of the blood sample;

a second light emitting part configured for emitting light to the measurement sample;

a second light receiving part configured for obtaining optical information by receiving light of a plurality of wavelengths over time from the measurement sample; and a controller configured for executing operations comprising:

measuring, based on the optical information obtained by the first light receiving part, content of an interference substance which interferes with the optical information obtained by the second light receiving part; and measuring coagulation time of the measurement sample based on the optical information obtained by the second light receiving part.

15. The sample analyzer according to claim 14, wherein the measuring content of the interference substance is carried out by measuring contents of a plurality of interference substances based respectively on the optical information at a plurality of wavelengths obtained by the first light receiving part.

16. The sample analyzer according to claim 14, wherein the first light receiving part is configured so as to obtain first optical information of a sample at light of a first wavelength, second optical information of a sample at light of a second wavelength, and third optical information of a sample at light of a third wavelength;

the measuring content of the interference substance is carried out by measuring at least one of bilirubin, hemoglobin, and chyle in the blood sample based on the first, second, and third optical information obtained by the first light receiving part.

17. The sample analyzer according to claim 16, wherein:

first light of the first wavelength is absorbed by chyle, and is substantially not absorbed by bilirubin and hemoglobin;

second light of the second wavelength is absorbed by chyle and hemoglobin, and is substantially not absorbed by bilirubin;

third light of the third wavelength is absorbed by chyle, hemoglobin and bilirubin;

the measuring content of the interference substance comprises:

estimating influence by chyle on the second and third optical information based on the first optical information; and estimating influence by hemoglobin on the third optical information based on the second optical information and the influence by chyle on the second optical information;

obtaining contents of bilirubin, hemoglobin, and chyle in the blood sample based on:

the first, second, and third optical information;

the influence by chyle on the second and third optical information; and the influence by hemoglobin on the third optical information.

18. The sample analyzer according to claim 17, wherein the first light receiving part is configured so as to obtain fourth optical information at fourth light of a fourth wavelength, wherein fourth light of the fourth wavelength being is absorbed by chyle but is substantially not absorbed by bilirubin and hemoglobin; and estimating of the influence by chyle on the second and third optical information is carried out based on the first and fourth optical information.

19. The sample analyzer according to claim 14, wherein the first light receiving part is configured so as to obtain first optical information of a sample at first light of a first wavelength, second optical information of a sample at second light of a second wavelength, and third optical information at third light of a third wavelength, wherein the first light of the first wavelength is absorbed by chyle but is substantially not absorbed by bilirubin and hemoglobin, the second light of the second wavelength is absorbed by chyle and hemoglobin but is substantially not absorbed by bilirubin, and the third light of the third wavelength is absorbed by bilirubin, hemoglobin, and chyle; and measuring content of the interference substance comprises:

obtaining influence by chyle on the first, second, and third optical information based on first optical information;

obtaining influence by hemoglobin on second optical information and third optical information based on second optical information, and the influence by chyle on second optical information; and obtaining influence by bilirubin on third optical information based on third optical information, the influence by hemoglobin on third optical information and the influence by chyle on third optical information; and the sample analyzer further comprises:

an output part for outputting the influence by chyle, the influence by hemoglobin, and the influence by bilirubin on the first, second, and third optical information.

20. The sample analyzer according to claim 14, wherein one of the first light emitting part and the second light emitting part is configured so as to emit light of a plurality of mutually different wavelengths at time divisions.

21. The sample analyzer according to claim 14, wherein the operations further comprise:

deciding whether or not to obtain optical information by the second light receiving part based on measurement result of content of the interference substance.

22. A sample analyzer comprising:

a sample preparing part configured for preparing a measurement sample by mixing a reagent for measuring coagulation time with a blood sample;

a light emitting part configured for emitting light to the prepared measurement sample;

a light receiving part configured for obtaining optical information at a plurality of time points by receiving light of a plurality of wavelengths over time from the measurement sample irradiated by the light; and a controller configured for executing operations comprising:

correcting optical information obtained by the light receiving part at a time point before the measurement sample indicates coagulation reaction by subtracting a reagent induced absorbance;

measuring content of an interference substance which interferes with optical measurement of the measurement sample based on optical information corrected by the correcting step; and measuring coagulation time of the measurement sample based on the optical information obtained by the light receiving part.

23. A sample analyzer comprising:

a measuring part configured for measuring first optical information of a sample at first light of first wavelength, second optical information of a sample at second light of second wavelength, and third optical information of a sample at third light of third wavelength, wherein the first light of the first wavelength and the second light of the second wavelength are absorbed by a first substance but substantially not absorbed by a second substance, and wherein the third light of the third wavelength is absorbed by the second substance; and a controller configured for executing operations comprising:
estimating influence by the first substance on the third optical information based on the first optical information and the second optical information;
correcting the optical information at the third wavelength based on the estimated influence by the first substance on the third optical information;
obtaining content of the first substance in the sample based on the first and second optical information; and
obtaining content of second substance, from which influence by the first substance is excluded, in the sample based on the corrected third optical information.

* * * * *

UNITED STATES PATENT AND TRADEMARK OFFICE
CERTIFICATE OF CORRECTION

PATENT NO. : 7,760,340 B2  
APPLICATION NO. : 11/724934  
DATED : July 20, 2010  
INVENTOR(S) : Susumu Hoshiko et al.

It is certified that error appears in the above-identified patent and that said Letters Patent is hereby corrected as shown below:

In column 35, claim 5, line 53, after "optical information" delete "at the".

In column 36, claim 8, line 18, after "the correcting" insert --is--.

In column 36, claim 10, line 31, before "estimating of the influence" delete "first".

In column 36, claim 10, line 45, before "estimating of the influence" delete "third".

In column 38, claim 18, line 1, after "the fourth wavelength" delete "being".

Signed and Sealed this

Twenty-third Day of November, 2010

David J. Kappos
*Director of the United States Patent and Trademark Office*